United States Patent
Koh et al.

(10) Patent No.: US 8,628,956 B2
(45) Date of Patent: *Jan. 14, 2014

(54) EXPRESSION VECTOR SUITABLE FOR EXPRESSION OF A CODING SEQUENCE FOR GENE THERAPY

(75) Inventors: Daekyung Koh, Yongin-si (KR); Kyuhyun Lee, Yongin-si (KR); Hyeon Lee, Yongin-si (KR); Seongtae Yun, Yongin-si (KR); Eui-Cheol Jo, Yongin-si (KR)

(73) Assignee: Mogam Biotechnology Research Institute, Yongin-Si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/423,474

(22) Filed: Mar. 19, 2012

(65) Prior Publication Data

US 2012/0282685 A1    Nov. 8, 2012

Related U.S. Application Data

(62) Division of application No. 12/867,716, filed as application No. PCT/KR2008/000870 on Feb. 14, 2008, now Pat. No. 8,309,698.

(51) Int. Cl.
*C12N 15/63* (2006.01)
*C12N 15/113* (2010.01)
*C07H 21/04* (2006.01)

(52) U.S. Cl.
USPC ..................... 435/320.1; 536/24.1

(58) Field of Classification Search
USPC ............... 435/320.1; 536/24.1, 23.1
See application file for complete search history.

(56) References Cited

U.S. PATENT DOCUMENTS

2002/0076798 A1    6/2002    Miao et al.

FOREIGN PATENT DOCUMENTS

CN    1250477 A    4/2000
WO    98/33903 A1    8/1998

OTHER PUBLICATIONS

Palmiter et al 1991, Proc. Natl. Acad. Sci. USA 88,478-482.*
Liu, K., et al, Proc. Natl. Acad. Sci., 92: 7724-7728.*
Moore et al. Cell, 108: 431-434, 2002.*
Lei et al., "Identification of Hepatic Nuclear Factor 1 Binding Sites in the 5' Flanking Region of the Human Phenylalanine Hydroxylase Gene: Implication of a Dual Function of Phenylalanine Hydroxylase Stimulator in the Phenylalanine Hydroxylation System," Proc. Natl. Acad. Sci., 1998, vol. 95, pp. 1500-1504.
Kolev et al., "Symplekin and Multiple Other Polyadenylation Factors Participate in 3'-end Maturation of Histone mRNAs," Genes Dev., 2005, vol. 19, pp. 2583-2592.
Olds et al., "Complete Nucleotide Sequence of the Antithrombin Gene: Evidence for Homologous Recombination Causing Thrombophilia," Biochemistry, 1993, vol. 32, pp. 4216-4224.
Holcik et al., "Four Highly Stable Eukaryotic mRNAs Assemble 3' Untranslated Region RNA-Protein Complexes Sharing Cis and Trans Components," Proc. Natl. Acad. Sci., 1997, vol. 94, pp. 2410-2414.
Greenberg et al., "Liver-Specific Expression of the Human Factor VII Gene," Proc. Natl. Acad. Sci., 1995, vol. 92, pp. 12347-12351.
NCBI Accession No. NM_000133.3, 1 page.
Chinese Patent Office, Chinese Office Action issued in corresponding CN Application No. 201210084499.X, dated Dec. 21, 2012.
Pollak et al., "Functional Characterization of the Human Factor VII 5'-Flanking Region," The Journal of Biological Chemistry, 1996, vol. 271, No. 3, pp. 1738-1747.
Kramer et al., "In Vitro and in Vivo Comparative Study of Chimeric Liver-Specific Promoters," Molecular Therapy, 2003, vol. 7, No. 3, pp. 375-385.

* cited by examiner

*Primary Examiner* — Anoop Singh
(74) *Attorney, Agent, or Firm* — Sughrue Mion, PLLC

(57) ABSTRACT

Provided is an expression vector for gene therapy having a novel combination of transcriptional regulatory elements, including a promoter, an enhancer, an intron, an untranslated region (UTR) and a locus control region (LCR). The expression vector enables sustained expression of a liver tissue-specific gene, and thus, can be effectively used for treating thrombosis, hemophilia, liver cancer, etc.

19 Claims, 44 Drawing Sheets

Factor VII
(Vitamin-K dependent glucoprotein)

OATP-C
(Organic Anion-Transporting Polypeptide)

FIG. 12A

| Label | Construct |
|---|---|
| HCR-PF | ApoEHCR*lcr*PAH*enh*FVIIΔ*pro* 5'UTR-Exon1  Syn1PLA*int*  Exon2-8-3'UTR |
| HCRm-PF | ApoEHCRm*lcr*PAH*enh*FVIIΔ*pro* 5'UTR-Exon1  Syn1PLA*int*  Exon2-8-3'UTR |
| AFP3800-PF | AAT108*lcr*  PAH*enh*FVIIΔ*pro* 5'UTR-Exon1  Syn1PLA*int*  Exon2-8-3'UTR |
| AAT7800-PF | AAT7800*lcr*  PAH*enh*FVIIΔ*pro* 5'UTR-Exon1  Syn1PLA*int*  Exon2-8-3'UTR |
| AAT108-PF | AFP3800*lcr*  PAH*enh*FVIIΔ*pro* 5'UTR-Exon1  Syn1PLA*int*  Exon2-8-3'UTR |
| E6-PF | E6*lcr*  PAH*enh*FVIIΔ*pro* 5'UTR-Exon1  Syn1PLA*int*  Exon2-8-3'UTR |

AAT108-PF-ΔNAL

AAT108-PAF-ΔNAL

HmA-ΔNAL

HA-1.4kbFIXint

SEQUENCE LISTING

```
<160> NUMBER OF SEQ ID NOS: 63

<210> SEQ ID NO 1
<211> LENGTH: 27
<212> TYPE: DNA
<213> ORGANISM: Artificial Sequence
<220> FEATURE:
<223> OTHER INFORMATION: Synthetic construct (Factor VII pro XhoI sense
      primer)

<400> SEQUENCE: 1
ccgctcgagc ccggcacttc tcagtga                                       27

<210> SEQ ID NO 2
<211> LENGTH: 26
<212> TYPE: DNA
<213> ORGANISM: Artificial Sequence
<220> FEATURE:
<223> OTHER INFORMATION: Synthetic construct (Factor VII pro BamHI
      antisense primer)

<400> SEQUENCE: 2
cgggatccgc tgccctgcc tgttga                                         26

<210> SEQ ID NO 3
<211> LENGTH: 27
<212> TYPE: DNA
<213> ORGANISM: Artificial Sequence
<220> FEATURE:
<223> OTHER INFORMATION: Synthetic construct (OATP-C pro XhoI sense
      primer)

<400> SEQUENCE: 3
ccgctcgaga taactgtggc acagaca                                       27

<210> SEQ ID NO 4
<211> LENGTH: 26
<212> TYPE: DNA
<213> ORGANISM: Artificial Sequence
<220> FEATURE:
<223> OTHER INFORMATION: Synthetic construct (OATP-C pro BamHI antisense
      primer)

<400> SEQUENCE: 4
cgggatccta gaatcctaca gcaact                                        26

<210> SEQ ID NO 5
<211> LENGTH: 27
<212> TYPE: DNA
<213> ORGANISM: Artificial Sequence
<220> FEATURE:
<223> OTHER INFORMATION: Synthetic construct (AAT pro sense primer)

<400> SEQUENCE: 5
ttccctggtc tgaatgtgtg tgctgga                                       27

<210> SEQ ID NO 6
<211> LENGTH: 27
<212> TYPE: DNA
<213> ORGANISM: Artificial Sequence
```

```
<220> FEATURE:
<223> OTHER INFORMATION: Synthetic construct (AAT pro antisense primer)

<400> SEQUENCE: 6
actgtcccag gtcagtggtg gtgcctg                                              27

<210> SEQ ID NO 7
<211> LENGTH: 25
<212> TYPE: DNA
<213> ORGANISM: Artificial Sequence
<220> FEATURE:
<223> OTHER INFORMATION: Synthetic construct (PAH enh EcoRI sense
      primer)

<400> SEQUENCE: 7
ggaattcaag agaagggtca tgtag                                                25

<210> SEQ ID NO 8
<211> LENGTH: 27
<212> TYPE: DNA
<213> ORGANISM: Artificial Sequence
<220> FEATURE:
<223> OTHER INFORMATION: Synthetic construct (PAH enh XhoI antisense
      primer)

<400> SEQUENCE: 8
ccgctcgaga ggtggggaac atgtcac                                              27

<210> SEQ ID NO 9
<211> LENGTH: 24
<212> TYPE: DNA
<213> ORGANISM: Artificial Sequence
<220> FEATURE:
<223> OTHER INFORMATION: Synthetic construct (AMBP enh EcoRI sense
      primer)

<400> SEQUENCE: 9
ggaattccaa ttcccatgga ctct                                                 24

<210> SEQ ID NO 10
<211> LENGTH: 27
<212> TYPE: DNA
<213> ORGANISM: Artificial Sequence
<220> FEATURE:
<223> OTHER INFORMATION: Synthetic construct (AMBP enh XhoI antisense
      primer)

<400> SEQUENCE: 10
ccgctcgagc aagggcatgg tccagat                                              27

<210> SEQ ID NO 11
<211> LENGTH: 25
<212> TYPE: DNA
<213> ORGANISM: Artificial Sequence
<220> FEATURE:
<223> OTHER INFORMATION: Synthetic construct (Not I linker human FIX
      5'UTR sense primer)

<400> SEQUENCE: 11
ccgcggccgc accactttca caatc                                                25

<210> SEQ ID NO 12
<211> LENGTH: 26
<212> TYPE: DNA
<213> ORGANISM: Artificial Sequence
<220> FEATURE:
<223> OTHER INFORMATION: Synthetic construct (Sal I linker human FIX
      3'UTR antisense primer)
```

<400> SEQUENCE: 12
tagtcgacaa aaagcaatga tcatac                                           26

<210> SEQ ID NO 13
<211> LENGTH: 25
<212> TYPE: DNA
<213> ORGANISM: Artificial Sequence
<220> FEATURE:
<223> OTHER INFORMATION: Synthetic construct (Human FIX sense primer)

<400> SEQUENCE: 13
ccgcggccgc cgcggatgca gcgcg                                            25

<210> SEQ ID NO 14
<211> LENGTH: 27
<212> TYPE: DNA
<213> ORGANISM: Artificial Sequence
<220> FEATURE:
<223> OTHER INFORMATION: Synthetic construct (Human FIX antisense
      primer)

<400> SEQUENCE: 14
tagtcgacat cgattaagtg agctttg                                          27

<210> SEQ ID NO 15
<211> LENGTH: 23
<212> TYPE: DNA
<213> ORGANISM: Artificial Sequence
<220> FEATURE:
<223> OTHER INFORMATION: Synthetic construct (Human Antithrombin intron
      1 sense primer)

<400> SEQUENCE: 15
ggtgagcttt ccccttgcct gcc                                              23

<210> SEQ ID NO 16
<211> LENGTH: 23
<212> TYPE: DNA
<213> ORGANISM: Artificial Sequence
<220> FEATURE:
<223> OTHER INFORMATION: Synthetic construct (Human Antithrombin intron
      1 antisense primer)

<400> SEQUENCE: 16
caaaggtcac tgggatttgg gtg                                              23

<210> SEQ ID NO 17
<211> LENGTH: 24
<212> TYPE: DNA
<213> ORGANISM: Artificial Sequence
<220> FEATURE:
<223> OTHER INFORMATION: Synthetic construct (Human Plasminogen intron 1
      sense primer)

<400> SEQUENCE: 17
tagttttttt aaattataag aatt                                             24

<210> SEQ ID NO 18
<211> LENGTH: 23
<212> TYPE: DNA
<213> ORGANISM: Artificial Sequence
<220> FEATURE:
<223> OTHER INFORMATION: Synthetic construct (Human Plasminogen intron 1
      antisense primer)

<400> SEQUENCE: 18
tggtgagaga acggaatata ttc                                              23

<210> SEQ ID NO 19
<211> LENGTH: 24
<212> TYPE: DNA
<213> ORGANISM: Artificial Sequence
<220> FEATURE:
<223> OTHER INFORMATION: Synthetic construct (Human Prothrombin intron 1
      sense primer)

<400> SEQUENCE: 19
gtgcttgcag gctggaacag gctg                                             24

<210> SEQ ID NO 20
<211> LENGTH: 24
<212> TYPE: DNA
<213> ORGANISM: Artificial Sequence
<220> FEATURE:
<223> OTHER INFORMATION: Synthetic construct (Human Prothrombin intron 1
      antisense primer)

<400> SEQUENCE: 20
gggtcatgga acagcgacct cagg                                             24

<210> SEQ ID NO 21
<211> LENGTH: 23
<212> TYPE: DNA
<213> ORGANISM: Artificial Sequence
<220> FEATURE:
<223> OTHER INFORMATION: Synthetic construct (Human FIX intron 1
      antisense primer)

<400> SEQUENCE: 21
gtttgtttcc tttttaaaa tac                                               23

<210> SEQ ID NO 22
<211> LENGTH: 22
<212> TYPE: DNA
<213> ORGANISM: Artificial Sequence
<220> FEATURE:
<223> OTHER INFORMATION: Synthetic construct (Human FIX intron 1
      antisense primer)

<400> SEQUENCE: 22
ctgaaatgta aaagaataat tc                                               22

<210> SEQ ID NO 23
<211> LENGTH: 40
<212> TYPE: DNA
<213> ORGANISM: Artificial Sequence
<220> FEATURE:
<223> OTHER INFORMATION: Synthetic construct (Xho I linker synthetic
      splicing donor antisense primer)

<400> SEQUENCE: 23
gtaagtttct cgagggccgg gagcgatctg ggtcgagggg                            40

<210> SEQ ID NO 24
<211> LENGTH: 53
<212> TYPE: DNA
<213> ORGANISM: Artificial Sequence
<220> FEATURE:
<223> OTHER INFORMATION: Synthetic construct (Aat II linker synthetic
      splicing acceptor sense primer)

<400> SEQUENCE: 24
ctgaaaggga aaagaatgac gtcgccaaga tagtcagtaa atcaatgtta gta             53

<210> SEQ ID NO 25
<211> LENGTH: 24
<212> TYPE: DNA
<213> ORGANISM: Artificial Sequence
<220> FEATURE:
<223> OTHER INFORMATION: Synthetic construct (Full-length human
      antithrombin intron 1 antisense primer)

<400> SEQUENCE: 25
gaattcgccc ttcaagacgt caag                                          24

<210> SEQ ID NO 26
<211> LENGTH: 24
<212> TYPE: DNA
<213> ORGANISM: Artificial Sequence
<220> FEATURE:
<223> OTHER INFORMATION: Synthetic construct (AAT108 sense primer)

<400> SEQUENCE: 26
cgactcagat cccagccagt ggac                                          24

<210> SEQ ID NO 27
<211> LENGTH: 24
<212> TYPE: DNA
<213> ORGANISM: Artificial Sequence
<220> FEATURE:
<223> OTHER INFORMATION: Synthetic construct (AAT108 antisense primer)

<400> SEQUENCE: 27
gtatttaagc agtggatcca gagg                                          24

<210> SEQ ID NO 28
<211> LENGTH: 24
<212> TYPE: DNA
<213> ORGANISM: Artificial Sequence
<220> FEATURE:
<223> OTHER INFORMATION: Synthetic construct (AAT7800 sense primer)

<400> SEQUENCE: 28
gggatgttag tgtgtgtatg caca                                          24

<210> SEQ ID NO 29
<211> LENGTH: 24
<212> TYPE: DNA
<213> ORGANISM: Artificial Sequence
<220> FEATURE:
<223> OTHER INFORMATION: Synthetic construct (AAT7800 antisense primer)

<400> SEQUENCE: 29
atgatttcca ttctacttaa actg                                          24

<210> SEQ ID NO 30
<211> LENGTH: 25
<212> TYPE: DNA
<213> ORGANISM: Artificial Sequence
<220> FEATURE:
<223> OTHER INFORMATION: Synthetic construct (AFP3800 sense primer)

<400> SEQUENCE: 30
taaccaacca cccaatccaa caaac                                         25

<210> SEQ ID NO 31
<211> LENGTH: 25
<212> TYPE: DNA
<213> ORGANISM: Artificial Sequence
<220> FEATURE:
<223> OTHER INFORMATION: Synthetic construct (AFP3800 antisense primer)

```
<400> SEQUENCE: 31
agacaagcaa taaagaggag ctttg                                         25

<210> SEQ ID NO 32
<211> LENGTH: 24
<212> TYPE: DNA
<213> ORGANISM: Artificial Sequence
<220> FEATURE:
<223> OTHER INFORMATION: Synthetic construct (E6 sense primer)

<400> SEQUENCE: 32
agctttctga acagccaaac agag                                          24

<210> SEQ ID NO 33
<211> LENGTH: 24
<212> TYPE: DNA
<213> ORGANISM: Artificial Sequence
<220> FEATURE:
<223> OTHER INFORMATION: Synthetic construct (E6 antisense primer)

<400> SEQUENCE: 33
aactgaccct tgtaaataac tgtt                                          24

<210> SEQ ID NO 34
<211> LENGTH: 24
<212> TYPE: DNA
<213> ORGANISM: Artificial Sequence
<220> FEATURE:
<223> OTHER INFORMATION: Synthetic construct (ApoE HCR, HCRm sense
      primer)

<400> SEQUENCE: 34
ccagggatgg agagaaagag atga                                          24

<210> SEQ ID NO 35
<211> LENGTH: 24
<212> TYPE: DNA
<213> ORGANISM: Artificial Sequence
<220> FEATURE:
<223> OTHER INFORMATION: Synthetic construct (ApoE HCR antisense primer)

<400> SEQUENCE: 35
cagctacttg ggaggctgag gcag                                          24

<210> SEQ ID NO 36
<211> LENGTH: 24
<212> TYPE: DNA
<213> ORGANISM: Artificial Sequence
<220> FEATURE:
<223> OTHER INFORMATION: Synthetic construct (ApoE HCRm antisense
      primer)

<400> SEQUENCE: 36
ccctctcaca ctacctaaac cacg                                          24

<210> SEQ ID NO 37
<211> LENGTH: 47
<212> TYPE: DNA
<213> ORGANISM: Artificial Sequence
<220> FEATURE:
<223> OTHER INFORMATION: Synthetic construct (Not I linker 5'FU-signal
      peptide sense primer)

<400> SEQUENCE: 37
gcggccgcac cactttcaca atctgctagc aaaggttatg gagacag                 47
```

<210> SEQ ID NO 38
<211> LENGTH: 35
<212> TYPE: DNA
<213> ORGANISM: Artificial Sequence
<220> FEATURE:
<223> OTHER INFORMATION: Synthetic construct (Xho I linker signal peptide-NAL antisense primer)

<400> SEQUENCE: 38

```
ctcgagaaac ttacgtcacc agtggaacct ggaac                         35
```

<210> SEQ ID NO 39
<211> LENGTH: 43
<212> TYPE: DNA
<213> ORGANISM: Artificial Sequence
<220> FEATURE:
<223> OTHER INFORMATION: Synthetic construct (NAL-LK sense primer)

<400> SEQUENCE: 39

```
gacgtcattc ttttcccttt caggcggccc agccggccaa aag                43
```

<210> SEQ ID NO 40
<211> LENGTH: 147
<212> TYPE: DNA
<213> ORGANISM: Artificial Sequence
<220> FEATURE:
<223> OTHER INFORMATION: Synthetic construct (LK-3'FU antisense primer)

<400> SEQUENCE: 40

```
gtcgacaaaa agcaatgatc atagaatgta tatattcaaa tctaacaaaa gatgggaaag    60
tgattagtta gtgagaggcc ctgttaattt tcaattccaa tgaattaacc ttggaaatcc   120
atctttcact cgagttactt gtcatcg                                       147
```

<210> SEQ ID NO 41
<211> LENGTH: 516
<212> TYPE: DNA
<213> ORGANISM: Artificial Sequence
<220> FEATURE:
<223> OTHER INFORMATION: Synthetic construct (Factor VII promoter)
<220> FEATURE:
<221> NAME/KEY: misc_feature
<222> LOCATION: (1)..(6)
<223> OTHER INFORMATION: XhoI site
<220> FEATURE:
<221> NAME/KEY: misc_feature
<222> LOCATION: (511)..(516)
<223> OTHER INFORMATION: BamHI site

<400> SEQUENCE: 41

```
ctcgagcccg gcacttctca gtgaggctct gtggctcacc taagaaacca gcctcccttg    60
caggcaacgc ctagctggcc tggtctggag gctctcttca aatatttaca tccacaccca   120
agatacggtc ttgagatttg actcgcatga ttgctatggg acaagttttc atctgcagtt   180
taaatctgtt tcccaactta cattagggt ttggaattct agatcgtatt tgaagtgttg    240
gtgccacaca caccttaaca cctgcacgct ggcaacaaaa ccgtccgctc tgcagcacag   300
ctggggtcac ctgacctttc tcctgtcccc ccacttgag ctcagtggct gggcagcagg    360
ggatgcatgg ccactggcgg ccaggtgcag ctctcagctg gggtgttcag aggacgcctg   420
tgtcctcccc tccccatcc ctctgtcacc cttggaggca gagaactttg cccgtcagtc   480
ccatggggaa tgtcaacagg caggggcagc ggatcc                             516
```

<210> SEQ ID NO 42
<211> LENGTH: 303

<212> TYPE: DNA
<213> ORGANISM: Artificial Sequence
<220> FEATURE:
<223> OTHER INFORMATION: Synthetic construct (Factor VII truncated promoter)
<220> FEATURE:
<221> NAME/KEY: misc_feature
<222> LOCATION: (1)..(6)
<223> OTHER INFORMATION: EcoRI site
<220> FEATURE:
<221> NAME/KEY: misc_feature
<222> LOCATION: (298)..(303)
<223> OTHER INFORMATION: BamHI site

<400> SEQUENCE: 42

```
gaattctaga tcgtatttga agtgttggtg ccacacacac cttaacacct gcacgctggc      60
aacaaaaccg tccgctctgc agcacagctg gggtcacctg acctttctcc tgtcccccc     120 acttgagctc agtggctggg cagcagggga tgcatggcca ctggcggcca ggtgcagctc    180
tcagctgggg tgttcagagg acgcctgtgt cctcccctcc cccatccctc tgtcacccTT    240
ggaggcagag aactttgccc gtcagtccca tggggaatgt caacaggcag gggcagcgga    300
tcc                                                                  303
```

<210> SEQ ID NO 43
<211> LENGTH: 989
<212> TYPE: DNA
<213> ORGANISM: Artificial Sequence
<220> FEATURE:
<223> OTHER INFORMATION: Synthetic construct (OATP-C promoter)
<220> FEATURE:
<221> NAME/KEY: misc_feature
<222> LOCATION: (1)..(6)
<223> OTHER INFORMATION: XhoI site
<220> FEATURE:
<221> NAME/KEY: misc_feature
<222> LOCATION: (984)..(989)
<223> OTHER INFORMATION: BamHI site

<400> SEQUENCE: 43

```
ctcgagataa ctgtggcaca gacatcaaat acattttgct gcaaccatat caacaaatgt      60
cccatgaatg ataaggggta accatattct catatatgca tcctcacatt accacatata    120
tatatgtgca tatgtgtata caggtaaaag tgtgtatata tgtatacatg tatgtttgtg    180
tgtatataca tacatatatc ttcacacttt tctgaaatat atatatttat gtgagagaag    240
ggtctgtact ttatttcaga agagagctta atgtccaagg tataattgag agtctaaaat    300
gtttgagtta ttgaattaat taaacttcat ctctactcaa gaaaacttt aactgagtta    360 agctcttcct ttctccacaa gtcaagtcaa taaaaggaaa ctgtgatatt ataattctt    420 tcctgttttg atgtaaagaa tctatcgcat aaagcagtct taattttcat cattcagaaa   480
aatggtcttg cagttaattg ggactctctt attccaggtg gtatctccag tctccataca    540
taccacgtta gaaccatact tatgtaccaa gcaagagggg tatattttaa ttttttaaatg   600 ccaatgtaac ctgtaggcat attttttatt tgtcttaaat tatttcctat ttggaagttt    660
taaatacctg gaataattta ttgtactcat attttttaaag aaaaaaatct tatgccacca   720
acttaattga ataaacaagt aaaagccatt cccaaaagta aggtttactt gttaagatta    780
acaaaaaata atgtgagaat tctgagaaat ataatcttta aatattggca actgagtga    840 actcttaaaa ctactaggtt ttatatgttt gactagagca atgacataat aaggtggtta    900
atcatcactg gacttgtttt caaaaagcca actactttaa gaggaataaa gggtggactt    960
gttgcagttg ctgtaggatt ctaggatcc                                      989
```

```
<210> SEQ ID NO 44
<211> LENGTH: 249
<212> TYPE: DNA
<213> ORGANISM: Artificial Sequence
<220> FEATURE:
<223> OTHER INFORMATION: Synthetic construct (PAH enhancer)
<220> FEATURE:
<221> NAME/KEY: misc_feature
<222> LOCATION: (1)..(6)
<223> OTHER INFORMATION: EcoRI site
<220> FEATURE:
<221> NAME/KEY: misc_feature
<222> LOCATION: (244)..(249)
<223> OTHER INFORMATION: XhoI site

<400> SEQUENCE: 44
gaattctgag gaattatgat aaagagaat gaataaaaaa acaagagaag ggtcatgtag      60
gttttgtttc tgtgccatga actcatggat tatgattaac tcaaccttct gcacatgaag     120
ataaacaaga aagaactgat aaacctgcaa tggttgggta atcttcaact tccaaatcag     180
caaaggtcag ctctaagttt gccaagtaca caacttctca tcttgtgaca tgttccccac     240
ctcctcgag                                                             249

<210> SEQ ID NO 45
<211> LENGTH: 416
<212> TYPE: DNA
<213> ORGANISM: Artificial Sequence
<220> FEATURE:
<223> OTHER INFORMATION: Synthetic construct (AMBP enhancer)
<220> FEATURE:
<221> NAME/KEY: misc_feature
<222> LOCATION: (1)..(6)
<223> OTHER INFORMATION: EcoRI site
<220> FEATURE:
<221> NAME/KEY: misc_feature
<222> LOCATION: (411)..(416)
<223> OTHER INFORMATION: XhoI site

<400> SEQUENCE: 45
gaattccaat tcccatggac tcttagaccc ctgggccccc taggagggca gggaccccag      60
agcctccatc ctcccacccc agcagccaga aggggaggag ggggcagcag ctgtctgacc     120
actgttggtc ttgcaacttg tgtccccagg ttaatttta aaaagcagtc aaaagtccaa      180
gtggcccttg gcagcattta ctctctctgt ttgctctggt taataatctc aggagcacaa     240
acattcctgg aggcaggaga agaaatcaac atcctggact tatcctctgg gcctctcccc     300 accccccagga gaggctgtgc aactgaatga acagccctgt ccaagagagg ctaggactgg    360
ggcttctcca cccctgcgcg tctcagcttc ccatctggac catgcccttg ctcgag         416

<210> SEQ ID NO 46
<211> LENGTH: 427
<212> TYPE: DNA
<213> ORGANISM: Artificial Sequence
<220> FEATURE:
<223> OTHER INFORMATION: Synthetic construct (Antithrombin truncated 1st
      intron)

<400> SEQUENCE: 46
ggtgagcttt cccccttgcct gcccctactg ggttttgtga cctccaaagg actcacagga     60
atgacctcca acacctttga gaagaccagg ccctctccct ggtagttaca gtcaaagacc     120
tgtttggaag acgtcatttc aagtgctctc cctcccaccc cacctcttgg ggtaaggcct     180
ttcctaagct accccttggg tcctagcct aagaaacaag gggatgtca tccctggtgt       240 aaagatgctg tgcaggaagt cagcactcac gggatccagg ggacgctcca agggaatcc     300
```

```
ccagggcctg ccatccatcc gggaagagag caaatgctac ccatgaggac ctcctcactc    360 ccttttgct  ctttcttcca ctcagatcca ccccactcca cccccaccca aatcccagtg    420
acctttg                                                              427
```

<210> SEQ ID NO 47
<211> LENGTH: 422
<212> TYPE: DNA
<213> ORGANISM: Artificial Sequence
<220> FEATURE:
<223> OTHER INFORMATION: Synthetic construct (Plasminogen truncated 1st
      intron)

<400> SEQUENCE: 47

```
tagttttttt aaattataag aattattttt tctcccacaa tgtagtaaaa atacatatgc     60
catggcttta tgtgcaattc atttaatttt tgattcatga aacttccagt tgaaaatctt    120
gtataagatt gaggaattct tcaagaaata agtttaagtt tcctgtgaag attgtcaggg    180
tgctggaatg aatgggcaga gaaaataatg ggtgattttt caaatctaaa tgagtgcacc    240
cacataatgg ccagtctaat tgaaaaagag ccaatgtagc taattatgca aaggacggct    300
aagctctttg cctggttctc agtttgacta atttatatca tctctgttac ggtgtcatgc    360 tccccctcact tgcaagttaa aacagtgaaa tatctctttg aatatattcc gttctctcac    420
ca                                                                   422
```

<210> SEQ ID NO 48
<211> LENGTH: 361
<212> TYPE: DNA
<213> ORGANISM: Artificial Sequence
<220> FEATURE:
<223> OTHER INFORMATION: Synthetic construct (Prothrombin truncated 1st
      intron)

<400> SEQUENCE: 48

```
gtgcttgcag gctggaacag gctggaggac tggggtgtgg gcccatgggc tggggtctcc     60
tggctggaca gagcacacag agctggcccc taagtaggtc tcagccccag gcggccagct    120
tagggaagaa gtcaggagct cagggctgga aagagaatgg ctgcttctct cttccaatat    180
agggagcagg ctgggggcaa ggggcagtgt aggaggggca caggggggcca catttagcag    240 ccttccaggc cttccaccag cccagactgc ctctctcaga agccagcagg ggagggtggg    300
cttgcttcat gcccccagat ggccaagact gcctgttcct gaggtcgctg ttccatgacc    360
c                                                                    361
```

<210> SEQ ID NO 49
<211> LENGTH: 524
<212> TYPE: DNA
<213> ORGANISM: Artificial Sequence
<220> FEATURE:
<223> OTHER INFORMATION: Synthetic construct (Syn1AT intron)
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (15)..(40)
<223> OTHER INFORMATION: G-triple motif
<220> FEATURE:
<221> NAME/KEY: misc_feature
<222> LOCATION: (468)..(489)
<223> OTHER INFORMATION: Branch sequence
<220> FEATURE:
<221> NAME/KEY: misc_feature

```
<222> LOCATION: (490)..(524)
<223> OTHER INFORMATION: Splicing acceptor sequence

<400> SEQUENCE: 49
gtaagtttct cgagggccgg gagcgatctg ggtcgagggg ggtgagcttt cccccttgcct     60 gccccctactg ggttttgtga cctccaaagg actcacagga atgacctcca acacctttga   120
gaagaccagg ccctctccct ggtagttaca gtcaaagacc tgtttggaag acgtcatttc    180
aagtgctctc cctcccaccc cacctcttgg ggtaaggcct ttcctaagct accccttggg    240
tccctagcct aagaaacaag ggggatgtca tccctggtgt aaagatgctg tgcaggaagt    300
cagcactcac gggatccagg ggacgctcca aggggaatcc ccagggcctg ccatccatcc    360
gggaagagag caaatgctac ccatgaggac ctcctcactc ccttttttgct ctttcttcca   420 ctcagatcca ccccactcca cccccaccca atcccagtg  acctttgtac taacattgat    480
ttactgactg actatcttgg cgacgtcatt cttttccctt tcag                     524

<210> SEQ ID NO 50
<211> LENGTH: 507
<212> TYPE: DNA
<213> ORGANISM: Artificial Sequence
<220> FEATURE:
<223> OTHER INFORMATION: Synthetic construct (Syn1PLA intron)
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (15)..(40)
<223> OTHER INFORMATION: G-triple motif
<220> FEATURE:
<221> NAME/KEY: misc_feature
<222> LOCATION: (463)..(484)
<223> OTHER INFORMATION: Branch sequence
<220> FEATURE:
<221> NAME/KEY: misc_feature
<222> LOCATION: (485)..(507)
<223> OTHER INFORMATION: Splicing acceptor sequence

<400> SEQUENCE: 50
gtaagtttct cgagggccgg gagcgatctg ggtcgagggg tagttttttt aaattataag     60
aattattttt tctcccacaa tgtagtaaaa atacatatgc catggcttta tgtgcaattc    120
atttaatttt tgattcatga aacttccagt tgaaaatctt gtataagatt gaggaattct    180
tcaagaaata agtttaagtt tcctgtgaag attgtcaggg tgctggaatg aatgggcaga    240
gaaaataatg ggtgattttt caaatctaaa tgagtgcacc cacataatgg ccagtctaat    300
tgaaaaagag ccaatgtagc taattatgca aaggacggct aagctctttg cctggttctc    360
agtttgacta atttatatca tctctgttac ggtgtcatgc tcccctcact tgcaagttaa    420
aacagtgaaa tatctctttg aatatattcc gttctctcac catactaaca ttgatttact    480
gactgacgtc attcttttcc ctttcag                                        507

<210> SEQ ID NO 51
<211> LENGTH: 458
<212> TYPE: DNA
<213> ORGANISM: Artificial Sequence
<220> FEATURE:
<223> OTHER INFORMATION: Syn1PT intron
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
```

```
<222> LOCATION: (15)..(40)
<223> OTHER INFORMATION: G-triple motif
<220> FEATURE:
<221> NAME/KEY: misc_feature
<222> LOCATION: (402)..(423)
<223> OTHER INFORMATION: Branch sequence
<220> FEATURE:
<221> NAME/KEY: misc_feature
<222> LOCATION: (424)..(458)
<223> OTHER INFORMATION: Splicing acceptor sequence

<400> SEQUENCE: 51
gtaagtttct cgagggccgg gagcgatctg ggtcgagggg gtgcttgcag gctggaacag      60
gctggaggac tggggtgtgg gcccatgggc tgggtctccc tggctggaca gagcacacag     120
agctggcccc taagtaggtc tcagcccag gcggccagct tagggaagaa gtcaggagct      180
cagggctgga aagagaatgg ctgcttctct cttccaatat agggagcagg ctgggggcaa     240
ggggcagtgt aggagggca caggggcca catttagcag ccttccaggc cttccaccag       300
cccagactgc ctctctcaga agccagcagg ggagggtggg cttgcttcat gccccagat     360 ggccaagact gcctgttcct gaggtcgctg ttccatgacc ctactaacat tgatttactg     420
actgactatc ttggcgacgt cattctttc cctttcag                             458

<210> SEQ ID NO 52
<211> LENGTH: 464
<212> TYPE: DNA
<213> ORGANISM: Artificial Sequence
<220> FEATURE:
<223> OTHER INFORMATION: Syn2AT intron
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (442)..(464)
<223> OTHER INFORMATION: Splicing acceptor sequence

<400> SEQUENCE: 52
gtaagtttct cgagggtgag ctttcccctt gcctgcccct actgggtttt gtgacctcca      60
aaggactcac aggaatgacc tccaacacct ttgagaagac caggccctct ccctggtagt     120
tacagtcaaa gacctgtttg gaagacgtca tttcaagtgc tctccctccc accccacctc     180
ttggggtaag gcctttccta agctaccct tgggtcccta gctaagaaa caaggggat        240 gtcatccctg gtgtaaagat gctgtgcagg aagtcagcac tcacgggatc caggggacgc     300
tccaagggga atccccaggg cctgccatcc atccgggaag agagcaaatg ctacccatga     360
ggacctcctc actcctttt tgctctttct tccactcaga tccacccac tccaccccca       420 cccaaatccc agtgaccttt ggacgtcatt cttttccctt tcag                     464

<210> SEQ ID NO 53
<211> LENGTH: 459
<212> TYPE: DNA
<213> ORGANISM: Artificial Sequence
<220> FEATURE:
<223> OTHER INFORMATION: Syn2PLA intron
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (437)..(459)
<223> OTHER INFORMATION: Splicing acceptor sequence

<400> SEQUENCE: 53
```

```
gtaagtttct cgagtagttt ttttaaatta taagaattat tttttctccc acaatgtagt    60
aaaaatacat atgccatggc tttatgtgca attcatttaa tttttgattc atgaaacttc   120
cagttgaaaa tcttgtataa gattgaggaa ttcttcaaga aataagttta agtttcctgt   180
gaagattgtc agggtgctgg aatgaatggg cagagaaaat aatgggtgat ttttcaaatc   240
taaatgagtg cacccacata atggccagtc taattgaaaa agagccaatg tagctaatta   300
tgcaaaggac ggctaagctc tttgcctggt tctcagtttg actaatttat atcatctctg   360
ttacggtgtc atgctcccct cacttgcaag ttaaaacagt gaaatatctc tttgaatata   420
ttccgttctc tcaccagacg tcattctttt ccctttcag                          459
```

<210> SEQ ID NO 54
<211> LENGTH: 398
<212> TYPE: DNA
<213> ORGANISM: Artificial Sequence
<220> FEATURE:
<223> OTHER INFORMATION: Synthetic construct (Syn2PT intron)
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (376)..(398)
<223> OTHER INFORMATION: Splicing acceptor sequence

<400> SEQUENCE: 54

```
gtaagtttct cgaggtgctt gcaggctgga acaggctgga ggactggggt gtgggcccat    60
gggctggggt ctcctggctg acagagcac acagagctgg cccctaagta ggtctcagcc   120
ccaggcggcc agcttaggga agaagtcagg agctcagggc tggaaagaga atggctgctt   180
ctctcttcca atatagggag caggctgggg gcaaggggca gtgtaggagg ggcacagggg   240
gccacattta gcagccttcc aggccttcca ccagcccaga ctgcctctct cagaagccag   300
caggggaggg tgggcttgct tcatgccccc agatggccaa gactgcctgt tcctgaggtc   360
gctgttccat gacccgacgt cattcttttc cctttcag                           398
```

<210> SEQ ID NO 55
<211> LENGTH: 2324
<212> TYPE: DNA
<213> ORGANISM: Artificial Sequence
<220> FEATURE:
<223> OTHER INFORMATION: Synthetic construct (NA intron)
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (2302)..(2324)
<223> OTHER INFORMATION: Splicing acceptor sequence

<400> SEQUENCE: 55

```
gtaagtttct cgagctttcc ccttgcctgc ccctactggg ttttgtgacc tccaaaggac    60
tcacaggaat gacctccaac acctttgaga agaccaggcc ctctccctgg tagttacagt   120
caaagacctg tttggaagac gtcatttcaa gtgctctccc tcccacccca cctcttgggg   180
taaggccttt cctaagctac cccttgggtc cctagcctaa gaaacaaggg ggatgtcatc   240
cctggtgtaa agatgctgtg caggaagtca gcactcacgg gatccagggg acgctccaag   300
gggaatcccc agggcctgcc atccatccgg gaagagagca aatgctaccc atgaggacct   360
cctcactccc ttttgctct ttcttccact cagatccacc ccactccacc cccacccaaa    420
```

```
tcccagtgac ctttgactaa agggccaaaa ctgcttcctt ttctcacaat gagagttgtc    480
cctccctcaa tgccacacac actcccttct tcatctgagt tgtcacagga ggctagaaac    540
ggggtggtgg cacaactgtc ttggttttaa tttgtgcttc atagccctcc cagggtcctc    600
tcagcctcaa attgcatttc caaatgtagt ttgaaggaca gagtgggcaa ccgaaggcag    660
tggagatggg aagatgaatg gcagggtcct ctcctctctc tctctgcttc ttcagcctgc    720
cttccacatc tcccttggtg ccgctgcttc tctccggctt gcacctctg  ttcttgaaag    780 ggctgcagaa ctggactcag accacgcaag aaggcaagtc ccctcagct  gcccagctt    840 ccagccagcc ccaggcttgc ccaacggacc acgtccgtga atctgcactg ggtgcctgtc    900
tttctctccc aggagaagat gggaagatcc agtacccaca cacagacccc cttgtgtaca    960
cgcaggaacc ataaaccagc tggaggcagc ccctgcccca ccctgtctta tctacaaaaa   1020
atattacaag agactttatc tcttgatttg cttcatcgag tgtcccaact acctcatttt   1080
tttaaaatgt gaaattagct tcatttacct tcattgaatc catgttggcg actattaaaa   1140
attccaggca ataaaaggg  atgagagcct gaactaaagc agtggcaata actggtgaaa   1200
gagtaaaaaa acagaactga ttgactctgg ggtgaactga ttgactctgg ggtttgacta   1260
aatgaggagg agagagggag gaatccaggg tgattctcag gtttctgtac gggattcact   1320
gagcccactc acaggagcag gcctgtgggg gagaattaat taccagttca gtttggtcct   1380
gtttccctga agaacttgta ggagttcctg gtggaactgt ccagcaaata gtcagtctgg   1440
agctcagtgg aagggttagg gctggagcta gagatgtagg aatcttcagc acacagatat   1500
tgccattgtt tttgtttgtt tgtttgtttg ttgttgctgt tttgagacac agtctcactt   1560
tgtcacccag gttggagtgc agtggcacaa tctcagctca ctgcaacctt cgcctcctgg   1620
gttcaagtga ttcttctgcc tcagcctccc tagtagcttg ggactacagg tgtgcgccac   1680
cacacccagc taattttttgt attttttagta gagacagggt ttcaccatgt tgtccaggct   1740
gatctcgaac acccaacctc aagtgatctg catgcctcag cctcccaaag tgctgggatt   1800
acaggcgtga gccaccgcac ccggccagat attgcctttg ctccatccat ttcttcttac   1860
ttctcttgtg ttgctgaaat ctctctgctg catctatcag agtccttccc caaacagttt   1920
ctgtagatgg ctcccctac  caccctgact cttcactggg cactaaagcc gattttttag   1980
gcatgcacat tccatgtcac aaacaggaag cttctcattc ttttttctcc cagcgtgggg   2040
aattgagcac ataatactcc aaataaccat cagatgattc taattccaac atgaccacgt   2100
ccaggcaact gaactgtccc ctggcaagaa gtctaggact gaacctgtcc cgggcccctg   2160
tacttggttc aaaggattta gcctttctct tggccacacc aggtgggctg gaatcctctg   2220
ctttactggg gcaaccctgt ggtgggcagt ggggctaggg gttgcagcct agcttaactt   2280
gacgtcttga agggcgaatt cgacgtcatt cttttccctt tcag                    2324
```

<210> SEQ ID NO 56
<211> LENGTH: 811
<212> TYPE: DNA
<213> ORGANISM: Artificial Sequence
<220> FEATURE:
<223> OTHER INFORMATION: Synthetic construct (Truncated NAL intron)
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (789)..(811)
<223> OTHER INFORMATION: Splicing acceptor sequence -continued

<400> SEQUENCE: 56

```
gtaagtttct cgagctttcc ccttgcctgc ccctactggg ttttgtgacc tccaaaggac    60
tcacaggaat gacctccaac acctttgaga agaccaggcc ctcctgggtt caagtgattc   120
ttctgcctca ccctccctag tagcttggga ctacaggtgt gcgccaccac acccagctaa   180
tttttgtatt tttagtagag acagggtttc accatgttgt ccaggctgat ctcgaacacc   240
caacctcaag tgatctgcat gcctcagcct cccaaagtgc tgggattaca ggcgtgagcc   300
accgcacccg gccagatatt gccttttgctc catccatttc ttcttacttc tcttgtgttg   360
ctgaaatctc tctgctgcat ctatcagagt ccttccccaa acagtttctg tagatggctc   420
cccctaccac cctgactctt cactgggcac taaagccgat ttttttaggca tgcacattcc   480 atgtcacaaa caggaagctt ctcattcttt tttctcccag cgtggggaat tgagcacata   540
atactccaaa taaccatcag atgattctaa ttccaacatg accacgtcca ggcaactgaa   600
ctgtcccctg gcaagaagtc taggactgaa cctgtcccgg gccctgtac ttggttcaaa   660 ggatttagcc tttctcttgg ccacaccagg tgggctggaa tcctctgctt tactggggca   720
accctgtggt gggcagtggg gctagggggtt gcagcctagc ttaacttgac gtcttgaagg   780
gcgaattcga cgtcattctt ttccctttca g                                  811
```

<210> SEQ ID NO 57
<211> LENGTH: 640
<212> TYPE: DNA
<213> ORGANISM: Artificial Sequence
<220> FEATURE:
<223> OTHER INFORMATION: Synthetic construct (Truncated NAS intron)
<220> FEATURE:
<221> NAME/KEY: misc_feature
<222> LOCATION: (1)..(14)
<223> OTHER INFORMATION: Splicing donor sequence
<220> FEATURE:
<221> NAME/KEY: misc_feature
<222> LOCATION: (618)..(640)
<223> OTHER INFORMATION: Splicing acceptor sequence

<400> SEQUENCE: 57

```
gtaagtttct cgagctttcc ccttgcctgc ccctactggg ttttgtgacc tccaaaggac    60
tcgaacaccc aacctcaagt gatctgcatg cctcagcctc ccaaagtgct gggattacag   120
gcgtgagcca ccgcacccgg ccagatattg cctttgctcc atccatttct tcttacttct   180
cttgtgttgc tgaaatctct ctgctgcatc tatcagagtc cttccccaaa cagtttctgt   240
agatggctcc ccctaccacc ctgactcttc actgggcact aaagccgatt ttttaggcat   300
gcacattcca tgtcacaaac aggaagcttc tcattctttt ttctcccagc gtggggaatt   360
gagcacataa tactccaaat aaccatcaga tgattctaat tccaacatga ccacgtccag   420
gcaactgaac tgtcccctgg caagaagtct aggactgaac ctgtcccggg ccctgtact   480 tggttcaaag gatttagcct ttctcttggc cacaccaggt gggctggaat cctctgcttt   540
actggggcaa ccctgtggtg ggcagtgggg ctaggggttg cagcctagct taacttgacg   600
tcttgaaggg cgaattcgac gtcattcttt tccctttcag                         640
```

<210> SEQ ID NO 58
<211> LENGTH: 120
<212> TYPE: DNA
<213> ORGANISM: Artificial Sequence
<220> FEATURE:
<223> OTHER INFORMATION: Synthetic construct (AAT1081cr)

<400> SEQUENCE: 58

```
cgactcagat cccagccagt ggacttagcc cctgtttgct cctccgataa ctggggtgac    60
cttggttaat attcaccagc agcctccccc gttgcccctc tggatccact gcttaaatac   120
```

<210> SEQ ID NO 59
<211> LENGTH: 410
<212> TYPE: DNA
<213> ORGANISM: Artificial Sequence
<220> FEATURE:
<223> OTHER INFORMATION: Synthetic construct (AAT7800lcr)

<400> SEQUENCE: 59

```
ggggatgtta gtgtgtgtat gcacatgtgt gcaaactgtt tgtcttcagc accctaagtg    60
ccttgtcctg ccctccctgg taaacctgag ggctccatcc caagagagca gggcacttct   120
ccaagtgtgt cctcagctcc ctgaatccca tccacacagc ttccagtacc tgagcctaag   180
tcgcttcaca gagtcttccc tatctgcttc ccacgtagcc ccgctggaga acagaggtag   240
agggaagagg gcagagaagt ccagaacaca cacgtcctca ttgttttgcta ggagggctga   300 tgttgaccca gcttgtgttt gcccttcttg cccaatgctc tctgaggggg agagccaaac   360
accaggtcct gagaaccagt ttaagtagaa tggaaatcat tgattttca               410
```

<210> SEQ ID NO 60
<211> LENGTH: 569
<212> TYPE: DNA
<213> ORGANISM: Artificial Sequence
<220> FEATURE:
<223> OTHER INFORMATION: Synthetic construct (AFP3800lcr)

<400> SEQUENCE: 60

```
taaccaacca cccaatccaa caaacaaaaa atgaaaagaa tctcagaaac agtgagataa    60
gagaaggaat tttctcacaa cccacacgta tagctcaact gctctgaaga agtatatatc   120
taatatttaa cactaacatc atgctaataa tgataataat tactgtcatt ttttaatgtc   180
tataagtacc aggcatttag aagatattat tccatttata tatcaaaata aacttgaggg   240
gatagatcat tttcatgata tatgagaaaa attaaaaatc agattgaatt atttgcctgt   300
catacagcta ataattgacc ataagacaat tacatttaaa ttagtttgaa tctttctaat   360
accaaagttc agtttactgt tccatgttgc ttctgagtgg cttcacagac ttatgaaaaa   420
gtaaacggaa tcagaattac atcaatgcaa aagcattgct gtgaactctg tacttaggac   480
taaactttga gcaataacac atatagattg aggattgttt gctgttagta tacaaactct   540
ggttcaaagc tcctctttat tgcttgtct                                     569
```

<210> SEQ ID NO 61
<211> LENGTH: 79
<212> TYPE: DNA
<213> ORGANISM: Artificial Sequence
<220> FEATURE:
<223> OTHER INFORMATION: Synthetic construct (Albumin E6lcr)

<400> SEQUENCE: 61

```
agctttctga acagccaaac agagattcca aagttcaggc accaaagttc agaccctaac    60
aattatttac aagggtcag                                                 79
```

<210> SEQ ID NO 62
<211> LENGTH: 29
<212> TYPE: DNA
<213> ORGANISM: Artificial Sequence
<220> FEATURE:
<223> OTHER INFORMATION: Synthetic construct (hFIX-5'UTR)

```
<400> SEQUENCE: 62
accactttca caatctgcta gcaaaggtt                                           29

<210> SEQ ID NO 63
<211> LENGTH: 122
<212> TYPE: DNA
<213> ORGANISM: Artificial Sequence
<220> FEATURE:
<223> OTHER INFORMATION: Synthetic construct (hFIX-3'UTR)

<400> SEQUENCE: 63
tgaaagatgg atttccaagg ttaattcatt ggaattgaaa attaacaggg cctctcacta         60
actaatcact ttcccatctt ttgttagatt tgaatatata cattctatga tcattgcttt        120
tt                                                                      122
```

EXPRESSION VECTOR SUITABLE FOR EXPRESSION OF A CODING SEQUENCE FOR GENE THERAPY

CROSS-REFERENCE TO RELATED APPLICATIONS

This application is a Divisional application of U.S. patent application No. 12/867,716 (issued as U.S. Pat. No. 8,309, 698) filed Aug. 13, 2010, which is a National Stage of International Application No. PCT/KR2008/000870 filed Feb. 14, 2008, the contents of all of which are incorporated herein by reference in their entirety.

FIELD OF THE INVENTION

The present invention relates to an expression vector for gene therapy, and more particularly, to an expression vector for gene therapy including a novel combination of transcriptional regulatory elements (cis-regulatory elements or cis-acting elements) which include a promoter, an enhancer, an intron, an untranslated region (UTR) and a locus control region (LCR), said vector being capable of sustaining the expression of a target gene at a high level in the liver.

BACKGROUND OF THE INVENTION

The functions of the liver include blood storage, sugar conversion and the secretion of various cytokines, as well as the expression of genes that affect many diseases such as genetic, cardiovascular, metabolic, hematologic and cancerous disorders. Various liver-specific diseases, such as infectious hepatitis, have been studied as targets for gene therapy.

A liver cell maintains a long lifespan after its formation, has receptors of most viral gene transporters, and is directly connected to the bloodstream, enabling an easy approach of a drug, and thus, the liver is recognized as an important candidate organ for gene therapy.

Hemophilia is a degenerative hemorrhagic disease caused by the deficiency of factor VIII (FVIII, f8) or factor IX (FIX, f9) gene located on the X chromosome, and is classified into Hemophilia A (FVIII deficiency) or B (FIX deficiency) depending on the mutated or deleted gene. As for drugs for treating Hemophilia A or B, the therapeutic effect can be expected only when FVIII or FIX is continuously expressed at a level of 1-5% or more of the normal blood concentration thereof (100-200 ng/ml and 500 ng/ml, respectively).

In recent gene therapy studies of hemophilia B, it has been reported that the introduction of adeno-associated virus (AAV) carrying human FIX (hFIX) gene into a hemophilia B mouse model led to the expression of hFIX protein at a level of up to 1,500-1,800 ng/ml (Snyder, R. O., *Nat. Med.,* 5: 64-70 (1999); Manno, C. S., *Nat. Med.,* 12: 342-347 (2006)), while hFIX protein was expressed at the level of up to 730 ng/ml in a hemophilia B dog model (Arruda, V. R., *Blood,* 105: 3458-3464 (2005)). However, when such highly efficient expression vector for an animal model was clinically applied to a human patient, the blood concentration of FIX was only 185 ng/ml or less, which is less than 500 ng/ml, the threshold value for an effective clinical treatment, and besides, the problem was that the hFIX expression level in a human subject was not sustained but transient (Kay, M. A., *Nat. Genet.,* 24: 257-261 (2000); Manno, C. S., *Nat. Med.,* 12: 342-347 (2006)). A trend similar to the above has been found in the treatment models for hemophilia A.

The results of clinical tests for the treatment of a genetic disease such as hemophilia show that it is prerequisite to develop an efficient tissue-specific expression vector capable of keeping a high and sustained level of expression of a therapeutic gene in a specific tissue such as a liver tissue. Further, the escaping from humoral and cellular immune response against a vector and the induction of immune tolerance to an expressed protein have been recognized as critical factors for the successful gene therapy. For example, in order to raise the expression level of normal FVIII or FIX to a threshold value effective for successful clinical treatment, the injection of a high dose of virus carrying FVIII or FIX gene as well as the suppression of in vivo immune response also have to be considered. For such approaches to success, however, it is prerequisite to enhance the gene expression efficiency by the improvement of an expression vector.

Lipoprotein (a) produced only in the liver is another important target for the development of a liver tissue-specific expression vector. Lipoprotein (a) is formed through the binding of apolipoprotein (a), a glycoprotein, with apo B-100, a major protein component of low-density lipoprotein (LDL) (Fless, G. M., *J. Biol. Chem.,* 261: 8712-8717 (1986)). Apolipoprotein (a) is responsible for cholesterol transportation in vivo, and the increase of the lipoprotein (a) concentration in the plasma has been reported to be a major risk factor of arteriosclerosis and cardiac diseases (Armstrong, V. W. et al, *Arteriosclerosis,* 62: 249-257 (1986); Assmann, G., Am. J. Cardiol., 77: 1179-1184 (1996)). Apolipoprotein (a) contains two types of kringle domains similar to plasminogen kringles IV and V, together with an inactive protease-like domain. It is well known that proteins having a kringle structure may inhibit tumor neovascularization and metastasis (Folkman J., N Eng J Med, 285: 1182-1186 (1971); Falkman J, Klagsbrun M., Science, 235: 442-447 (1987); Scapaticci F A., J Clin Oncol., 20: 3906-3927 (2002)). Recently, the present inventors as well as other researchers have found that the kringle domains of apolipoprotein (a) have anti-cancer and anti-metastasis activities owing to their significant anti-angiogenesis activity (Sculter V et al, Arterioscler Thromb Vasc Biol, 21: 433-438 (2001); Trieu U N and Uckun F M., Biochem Biophys Res Commun., 257: 714-718 (1999); Kim J S et al, J. Biol Chem., 278: 29000-29008 (2003); Yu H K et al, Cancer Res., 64: 7092-7098 (2004); Kim J S et al, Biochem Biophys Res Commun., 313: 534-540 (2004); Lee K et al, Hepatology, 43: 1063-1073 (2006)).

In anti-metastasis and anti-cancer therapy, it has been widely recognized that a mode of therapy which selectively acts on an affected site would be most effective. Therefore, it is very important to develop a vector having the ability of tissue-specific and continuous gene expression for anticancer therapy, e.g., for effective gene therapy for liver cancer or metastatic liver tumors.

As described above, tissue-specific and sustained gene expression is the key for efficient gene therapy, which requires the development of a novel, improved expression vector. This may be achieved by the improvement of the transcriptional regulatory elements (cis-regulatory elements or cis-acting elements) of such an expression vector.

Examples of common transcriptional regulatory elements include a promoter, an enhancer, an intron, an untranslated region, a locus control region, and others.

Used for such an expression vector for liver tissue-specific expression are promoters of phosphoenolpyruvate carboxykinase (PEPCK), a gluconeogenesis enzyme (Yang, Y. W., J. et al, *Gene Med.,* 5(5): 417-424 (2003)), α1-antitrypsin protease, albumin, FVII, organic anion-transporting polypeptide-C(OATP-C), hepatitis B virus core (Kramer, M. G., et al, *Mol. Ther.,* 7(3): 375-385 (2003)), and thyroxin-binding globulin (Wang, L., et al, *Proc. Natl. Acad. Sci.,* 96: 3906-

3910 (1999)); and enhancers of albumin (Kang, Y., et al, *Blood*, 106(5): 1552-1558 (2005)), phenylalanine hydroxylase (PAH) and α1-microglobulin/bikunin precursor (AMBP) (Wang, L., et al., *Mol. Ther.*, 1(2): 154-158 (2000)).

The FVII promoter having a size of about 500 bp is transcriptionally activated in the liver at a level 10-fold or more higher than in other tissues, due to the binding of liver-enriched HNF-4 (hepatocyte nuclear factor-4). It has been reported that most transcription factors are mostly bound to a 300-bp fragment of the 3'-end of the FVII promoter (Greenberg, D., et al, *Proc. Natl. Acad. Sci.*, 92: 12347-12351 (1995)). When a 315-bp fragment of the 5'-end of a FVII promoter with a size of 501 bp is truncated, the liver-specific activity of the promoter increases by about 30%, but it decreases by about 20-30% when a 210-bp fragment is truncated (Pollak, W. S., et al, *J. Biol. Chem.*, 271(3): 1738-1747 (1996)).

An organic anion-transporting polypeptide-C (OATP-C) promoter having a size of about 900 bp is transcriptionally activated in the liver at a level 3-fold or more higher than in other tissues, due to liver-enriched HNF-1α binding. It has been reported that most transcription factors are bound to a 440-bp fragment of the 3'-end of the promoter (Jung, D., et al, *J. Biol. Chem.*, 276: 37206-37214 (2001)).

The activity of a promoter can be raised by the action of an enhancer. Phenylalanine hydroxylase (PAH) enhancer, which has a size of about 230 bp and HNF-1 binding sites, is located −3.5 kb upstream of the 5'-end of the PAH gene. It has been reported that the PAH enhancer increases the activity of the promoter bound thereto by 4-fold or more, due to the presence of liver-enriched HNF-1 binding sites (Lei, X. D., et al, *Proc. Natl. Acad. Sci.*, 95: 1500-1504 (1998)).

AMBP (α1-microglobulin/bikunin precursor) enhancer has a size of about 400 bp, which extends from −2945 to −2539 bp upstream of the 5'-end of the AMBP gene. It is mainly composed of HNF-1, 2, 3 and 4 binding sites, and its major active region corresponds to the −2802 to −2659 bp segment thereof (Route, P., et al, *Biochem. J.*, 334: 577-584 (1998)). Generally, it has been reported that the AMBP enhancer increases the promoter activity by about two or three times.

Untranslated regions (UTRs) located at the 5'- and 3'-ends of a gene are responsible for the structural stabilization of gene mRNA (Holcik, M., Liebhaber S. A., *Proc Natl Acad Sci USA.*, 94: 2410-2414 (1997); Chkheidze, A. N., et al, *Mol Cell Biol.*, 19: 4572-4581 (1999)). It has been reported that the polyadenylation signal sequence in 3' UTR also significantly contributes to the structural stabilization of the mRNA (Kolev, N. G., et al, *Genes Dev.*, 19: 2583-2592 (2005)).

A eukaryotic gene is composed of exons which are translated to proteins, and introns which are untranslated sequences between the exons. An mRNA precursor primarily transcribed from DNA is converted to a mature mRNA by the removal of such introns through splicing. Such introns include a splicing donor starting with GT(U) and a splicing acceptor ending with AG. Further, present in the 3'-end of an intron are, among others, a polypyrimidine tract, a splicing factor, an snRNP-binding branch sequence, a triple guanine repeat sequence (G-triple motif), which play critical roles in forming a spliceosome which is a complex of RNA and intron splicing enzyme (Pagani, F., et al, *Nat. Rev. Genet.*, 5: 389-396 (2004)).

An intron can be applied as a transcriptional regulatory element for sustained, efficient gene expression, when combined with a promoter and an enhancer. The intron is involved in enhancing the gene expression efficiency and transcription efficiency by its binding with transcription factors (Liu, K., et al, *Proc. Natl. Acad. Sci.*, 92: 7724-7728 (1995); LeBlanc, S. E., et al, *J. Biol. Chem.*, (2005)), and also in the enhancement of the post-transcriptional protein translation efficiency (Moore, M. J., *Cell*, 108: 431-434 (2002)). It has been reported that intron 1 of hFIX causes an increase in the expression of hFIX protein (Kurachi, S., et al, *J. Biol. Chem.*, 270: 5276-5281 (1995)).

Anti-coagulation proteins such as antithrombin and plasminogen, as well as coagulation factors such as prothrombin are expressed in the liver. On analyzing the introns of the gene of a thrombosis or hemophilia patient deficient of such proteins, various missense and/or nonsense mutations have been observed, which suggests that the introns of these proteins play critical roles in the gene expression in the liver (Jochmans, K., et al, *Blood*, 84: 3742-3748 (1994)).

Locus control regions (LCRs) have been found to be present in at least 36 types of mammals including human, rat, rabbit, goat and the like. LCRs are nucleotide sequences having a DNase I-sensitive region which is tissue-specific for transcription factors. The functions of human beta globin LCRs are well known (Harju S. et al, *Exp. Biol. Med.* 227: 683-700 (2002)).

A hepatocyte control region (HCR) is known for its ability to enhance the liver-specific gene expression, and found downstream of apolipoprotein E (ApoE) gene. HCR has a DNase I-sensitive region which binds with liver-specific transcription factors. The HCR acts as an LCR for liver-specific expression of ApoE gene. The ApoE HCR has sites that are activated when it binds with various factors such as HNF3α, HNF4, GATA-1, C/EBP, TF-LF2 and Alu-family. Among these sites, the HNF3α binding site showing hypersensitivity to DNase I has a TGTTTGC motif, and the link between the first G and the second T is cleaved by DNase I (Dang Q., et al, *J. Biol. Chem.* 270: 22577-22585 (1995)). Actually, it has been reported that the introduction of ApoE HCR into an expression vector leads to enhanced expression of hFIX in an animal model (Miao C. H., et al., *Mol. Ther.* 1: 522-532 (2000)).

Proteins having sequences similar to HCR of human ApoE gene including the TGTTTGC motif, apolipoprotein A-I, apolipoprotein B, transferin, α-fetoprotein, α1-antitrypsin and the like in human, and α-fetoprotein, albumin and the like in mouse have been reported (Dang Q., et al., *J. Biol. Chem.* 270: 22577-22585 (1995)).

SUMMARY OF THE INVENTION

Accordingly, it is an object of the present invention to provide a polynucleotide which can be used as a transcriptional regulatory element for sustained expression of a liver tissue-specific gene at a high level.

It is another object of the present invention to provide an expression vector for sustained expression of a liver tissue-specific gene at a high level.

In accordance with an aspect of the present invention, there is provided a polynucleotide having the nucleotide sequence of SEQ ID NO: 42.

In accordance with another aspect of the present invention, there is provided a polynucleotide including a polynucleotide having the nucleotide sequence of SEQ ID NO: 42 and at least one polynucleotide selected from the group consisting of polynucleotides having the nucleotide sequences of SEQ ID NOS: 44 and 45 operably linked to the polynucleotide of SEQ ID NO: 42.

In accordance with another aspect of the present invention, there is provided a polynucleotide selected from the group consisting of polynucleotides having the nucleotide sequences of SEQ ID NOS: 46 to 57.

In accordance with another aspect of the present invention, there is provided a polynucleotide selected from the group consisting of polynucleotides having the nucleotide sequences of SEQ ID NOS: 58 to 61.

In accordance with another aspect of the present invention, there is provided an expression vector including a transcriptional regulatory element and a coding sequence operably linked to and under control of the transcriptional regulatory element, wherein the transcriptional regulatory element includes:

1) a polynucleotide having the nucleotide sequence of SEQ ID NO: 42;

2) a polynucleotide having the nucleotide sequence of SEQ ID NO: 42 and at least one polynucleotide selected from the group consisting of polynucleotides having the nucleotide sequences of SEQ ID NOS: 44 and 45 operably linked to the polynucleotide of SEQ ID NO: 42;

3) a polynucleotide having the nucleotide sequence of SEQ ID NO: 42 and at least one polynucleotide selected from the group consisting of polynucleotides having the nucleotide sequences of SEQ ID NOS: 46 to 57 operably linked to the polynucleotide of SEQ ID NO: 42;

4) a polynucleotide having the nucleotide sequence of SEQ ID NO: 42 and at least one polynucleotide selected from the group consisting of polynucleotides having the nucleotide sequences of SEQ ID NOS: 58 to 61 operably linked to the polynucleotide of SEQ ID NO: 42;

5) a polynucleotide having the nucleotide sequence of SEQ ID NO: 42; at least one polynucleotide selected from the group consisting of polynucleotides having the nucleotide sequences of SEQ ID NOS: 44 and 45; and at least one polynucleotide selected from the group consisting of polynucleotides having the nucleotide sequences of SEQ ID NOS: 46 to 57, said polynucleotides being operably linked to each other;

6) a polynucleotide having the nucleotide sequence of SEQ ID NO: 42; at least one polynucleotide selected from the group consisting of polynucleotides having the nucleotide sequences of SEQ ID NOS: 44 and 45; and at least one polynucleotide selected from the group consisting of polynucleotides having the nucleotide sequences of SEQ ID NOS: 58 to 61, said polynucleotides being operably linked to each other;

7) a polynucleotide having the nucleotide of SEQ ID NO: 42; at least one polynucleotide selected from the group consisting of polynucleotides having the nucleotide sequences of SEQ ID NOS: 46 to 57; and at least one polynucleotide selected from the group consisting of polynucleotides having the nucleotide sequences of SEQ ID NOS: 58 to 61, said polynucleotides being operably linked to each other; or 8) a polynucleotide having the nucleotide of SEQ ID NO: 42; at least one polynucleotide selected from the group consisting of polynucleotides having the nucleotide sequences of SEQ ID NOS: 44 and 45; at least one polynucleotide selected from the group consisting of polynucleotides having the nucleotide sequences of SEQ ID NOS: 46 to 57; and at least one polynucleotide selected from the group consisting of polynucleotides having the nucleotide sequences of SEQ ID NOS: 58 to 61, said polynucleotides being operably linked to each other.

In accordance with a further aspect of the present invention, there is provided an expression vector including a transcriptional regulatory element and a coding sequence operably linked to and under control of the transcriptional regulatory element, the transcriptional regulatory element including a promoter and a polynucleotide which is operably linked to the promoter and selected from the group consisting of: at least one polynucleotide selected from the group consisting of polynucleotides having the nucleotide sequences of SEQ ID NOS: 46 to 57; at least one polynucleotide selected from the group consisting of polynucleotides having the nucleotide sequences of SEQ ID NOS: 58 to 61; and at least one polynucleotide selected from the group consisting of polynucleotides having the nucleotide sequences of SEQ ID NOS: 46 to 57 operably linked to at least one polynucleotide selected from the group consisting of polynucleotides having the nucleotide sequences of SEQ ID NOS: 58 to 61.

BRIEF DESCRIPTION OF DRAWINGS

The above and other objects and features of the present invention will become apparent from the following description of the invention taken in conjunction with the following accompanying drawings, which respectively show:

FIG. 12A: schematic diagrams showing expression cassettes obtained by introducing various LCRs (HCR, HCRm, AFP3800, AAT7800, AAT108 and E6) into hFIX expression cassettes containing PAH enhancer, FVIIΔ promoter and intron Syn1PLA;

DETAILED DESCRIPTION OF THE INVENTION

Figure 1A:
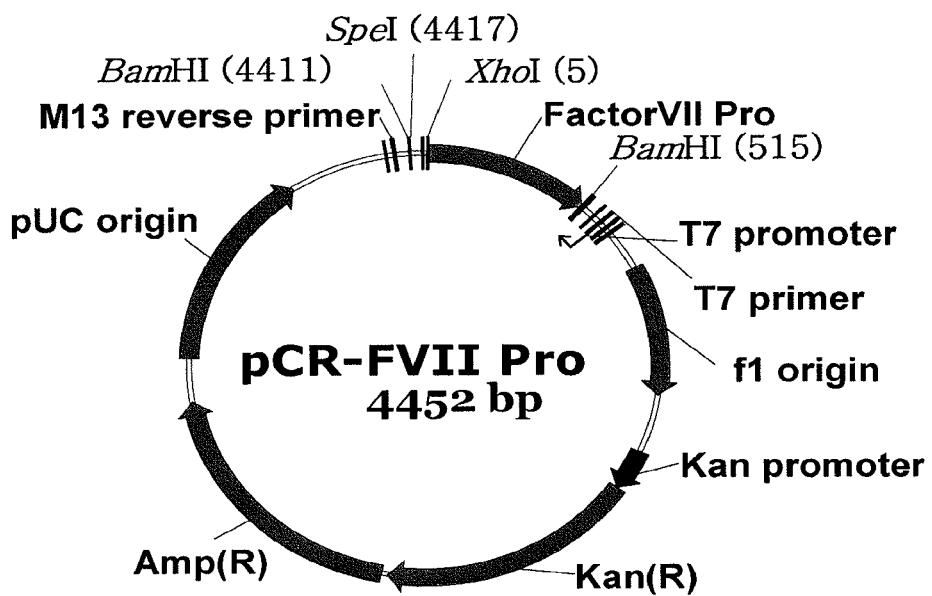
FIG. 1A: schematic diagrams of pCR-FVII Pro plasmid containing FVII promoter, pCR-OATP-C Pro plasmid containing organic anion-transporting polypeptide-C (OATP-C) promoter, and pCR-AAT Enh/Pro plasmid containing α-antitrypsin (AAT) promoter/enhancer.
Figure 1A:
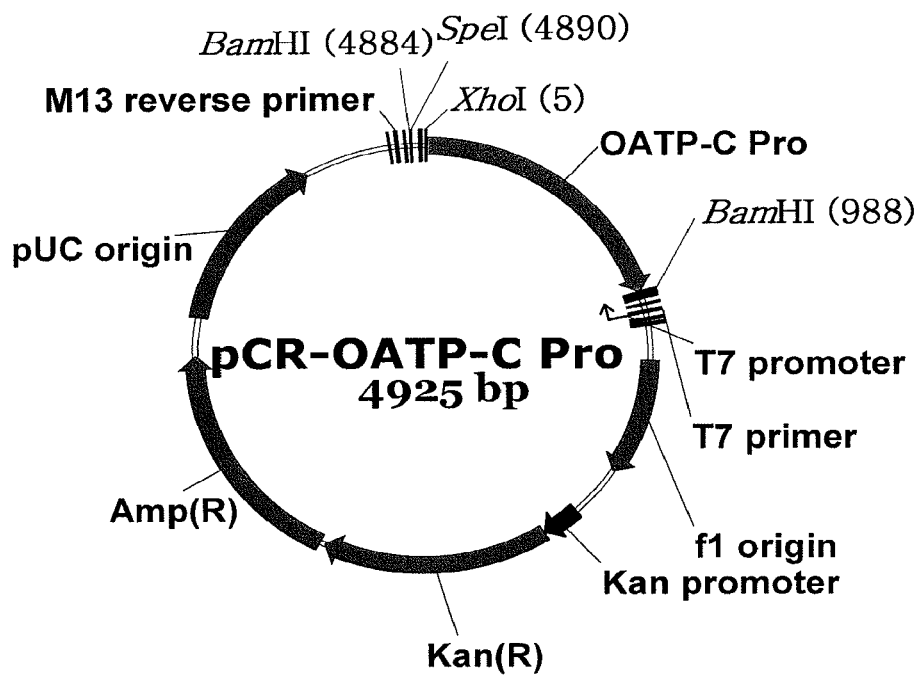
Figure 1A:
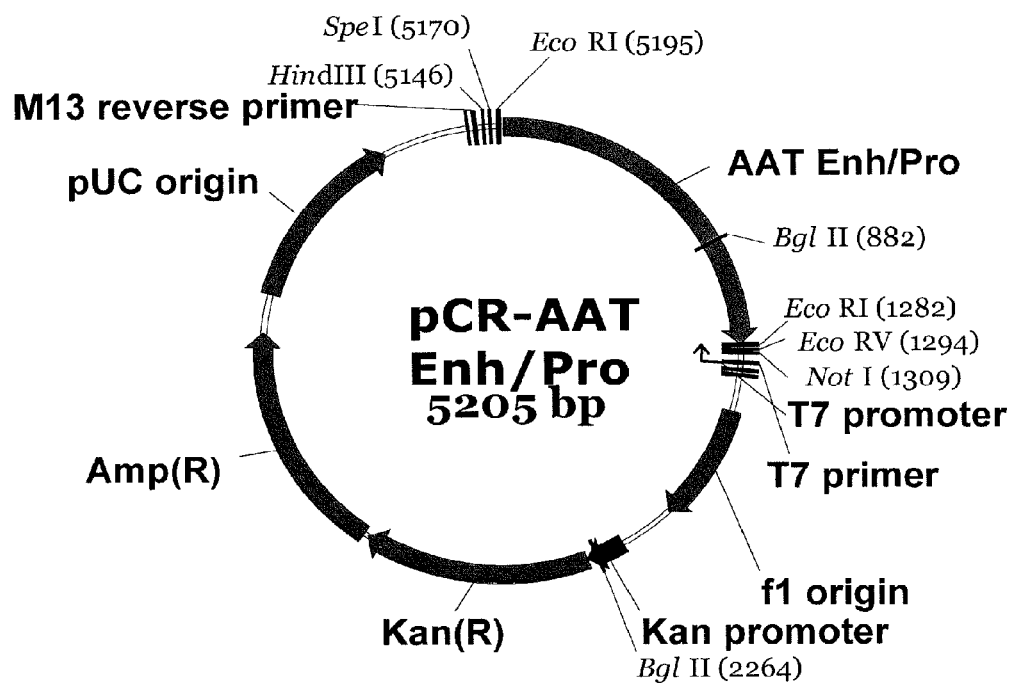

Unless defined otherwise, technical and scientific terms used herein have the same meaning as commonly understood by one of ordinary skill in the art to which the invention belongs. Further, all documents mentioned herein are incorporated by reference in their entireties.

The term "expression vector" as used herein, is intended to comprehend an aggregation (expression cassette or construct) including a coding sequence, a promoter, and optionally one or more transcriptional regulatory elements operably linked to the coding sequence, or a vector including the aggregation.

The term "coding sequence" as used herein means a DNA sequence encoding an amino acid or a functional RNA.

The term "transcriptional regulatory element (cis-regulatory element or cis-acting element)" as used herein means a nucleotide sequence located upstream, within, or downstream the coding sequence, which controls the RNA transcription, the processing, the stability and the subsequent translation of the transcribed RNA. The transcriptional regulatory element includes a promoter, an enhancer, an intron, 5'- and 3'-untranslated regions (UTRs), and a locus control region (LCR).

The terms "promoter" and "enhancer" as used herein are DNA sequences representing fragments that are needed to transcript the coding sequence to RNA. Typically, the promoter refers to a DNA segment which binds with a polymerase and transcription factors, and the enhancer refers to a DNA segment which binds with activation domains of the polymerase.

The term "untranslated region (UTR)" as used herein is a sequence located at the 3'- and 5'-ends of the coding sequence, and it contains a polyadenylation signal as a transcription termination region, and the like.

The term "intron" as used herein is an untranslated nucleotide sequence located between exons translated to a protein after transcription. The transcribed mRNA precursor is converted into a mature mRNA after the introns are removed through splicing. The term "intron" as used herein is also intended to comprehend a splicing donor, a splicing acceptor, a triple guanine repeat sequence (G-triple motif), and/or a branch sequence.

The term "locus control region (LCR)" as used herein is a nucleotide sequence having a DNase I-sensitive site. Tissue-specific transcription factors are bound to LCRs.

The term "operably linked" as used herein means the association of one or more nucleic acid sequences coupled to a single nucleic acid fragment such that the function of the single fragment is affected. For example, a promoter is operably linked with a coding sequence to enhance the expression of the coding sequence.

The present invention is described in detail hereinafter.

As described above, for effective gene therapy, a target gene should be specifically expressed in a specific tissue or cell in a sustained manner so that a pathogenic gene is replaced by the target gene. For tissue-specific and sustained gene expression, such an expression vector is required to include improved transcriptional regulatory elements.

Accordingly, the present invention provides a truncated FVII (FVIIΔ) promoter having the nucleotide sequence as set forth in SEQ ID NO: 42 which results from the truncation of a 207 bp fragment upstream of the 5'-end of a 504 bp FVII promoter by deleting XhoI (5'-end) and BamHI (3'-end) restriction sites from the nucleotide sequence of SEQ ID NO: 41. The following examples show that the FVIIΔ promoter has an activity which is 2.5-fold or more higher than that of the untruncated FVII promoter.

The FVIIΔ promoter may be combined with a suitable enhancer, e.g., at least one selected from the group consisting of a PAH enhancer having the nucleotide sequence as set forth in SEQ ID NO: 44 and an AMBP enhancer having the nucleotide sequence as set forth in SEQ ID NO: 45.

The present invention also provides an intron selected from the group consisting of polynucleotides having the nucleotide sequences as set forth in SEQ ID NOS: 46 to 57.

The introns of SEQ ID NOS: 46, 47 and 48 result from the truncation of introns 1 of human antithrombin, plasminogen and prothrombin, respectively. The introns of SEQ ID NOS: 49, 50 and 51 are synthetic introns that include the nucleotide sequences of SEQ ID NOS: 46, 47 and 48, respectively, and share a splicing donor sequence, a triple guanine repeat sequence (G-triple motif) derived from intron 2 of human α-globin, a branch sequence of human plasminogen, and a consensus splicing acceptor sequence. The introns of SEQ ID NOS: 52, 53 and 54 are synthetic introns lacking the G-triple motif and the branch sequence of the nucleotide sequences of SEQ ID NOS: 49, 50 and 51, respectively. The intron of SEQ ID NO: 55 is a synthetic intron that includes the full-length intron 1 of antithrombin, a splicing donor sequence and a consensus splicing acceptor sequence, and the introns of SEQ ID NOS: 56 and 57 are synthetic introns that result from the truncation of the nucleotide sequence of SEQ ID NO: 55. Among the above, the intron of SEQ ID NO: 57 is more preferred.

The present invention also provides a locus control region (LCR) selected from the group consisting of polynucleotides having the nucleotide sequences as set forth in SEQ ID NOS: 58 to 61.

The LCRs of SEQ ID NOS: 58, 59, 60 and 61 are located at −108 bp and −7.8 kb sites upstream of human α1-antitrypsin gene, −3.8 kb site upstream of human α-fetoprotein, and −6 kb site upstream of human albumin gene, respectively, among which the LCR of SEQ ID NO: 58 is preferred.

Polynucleotides which are substantially the same as, and functionally similar to, the sequences mentioned in the present invention are also within the scope of the present invention. The term "substantially the same and functionally similar polynucleotide" means that one polynucleotide has a nucleotide sequence which is at least 70%, preferably 80%, more preferably 90% and the most preferably 95% identical to the other polynucleotide, wherein the identity is determined by computerized algorithm or software.

The present invention also provides an expression vector including a transcriptional regulatory element and a coding sequence operably linked to and under control of the transcriptional regulatory element, wherein the transcriptional regulatory element includes:

1) a polynucleotide having the nucleotide sequence of SEQ ID NO: 42;

2) a polynucleotide having the nucleotide sequence of SEQ ID NO: 42 and at least one polynucleotide selected from the group consisting of polynucleotides having the nucleotide sequences of SEQ ID NOS: 44 and 45 operably linked to the polynucleotide of SEQ ID NO: 42;

3) a polynucleotide having the nucleotide sequence of SEQ ID NO: 42 and at least one polynucleotide selected from the group consisting of polynucleotides having the nucleotide sequences of SEQ ID NOS: 46 to 57 operably linked to the polynucleotide of SEQ ID NO: 42;

4) a polynucleotide having the nucleotide sequence of SEQ ID NO: 42 and at least one polynucleotide selected from the group consisting of polynucleotides having the nucleotide sequences of SEQ ID NOS: 58 to 61 operably linked to the polynucleotide of SEQ ID NO: 42;

5) a polynucleotide having the nucleotide sequence of SEQ ID NO: 42; at least one polynucleotide selected from the group consisting of polynucleotides having the nucleotide sequences of SEQ ID NOS: 44 and 45; and at least one polynucleotide selected from the group consisting of polynucleotides having the nucleotide sequences of SEQ ID NOS: 46 to 57, said polynucleotides being operably linked to each other;

6) a polynucleotide having the nucleotide sequence of SEQ ID NO: 42; at least one polynucleotide selected from the group consisting of polynucleotides having the nucleotide sequences of SEQ ID NOS: 44 and 45; and at least one polynucleotide selected from the group consisting of polynucleotides having the nucleotide sequences of SEQ ID NOS: 58 to 61, said polynucleotides being operably linked to each other;

7) a polynucleotide having the nucleotide sequence of SEQ ID NO: 42; at least one polynucleotide selected from the group consisting of polynucleotides having the nucleotide sequences of SEQ ID NOS: 46 to 57; and at least one polynucleotide selected from the group consisting of polynucleotides having the nucleotide sequences of SEQ ID NOS: 58 to 61, said polynucleotides being operably linked to each other; or 8) a polynucleotide having the nucleotide sequence of SEQ ID NO: 42; at least one polynucleotide selected from the group consisting of polynucleotides having the nucleotide sequences of SEQ ID NOS: 44 and 45; at least one polynucleotide selected from the group consisting of polynucleotides having the nucleotide sequences of SEQ ID NOS: 46 to 57; and at least one polynucleotide selected from the group consisting of polynucleotides having the nucleotide sequences of SEQ ID NOS: 58 to 61, said polynucleotides being operably linked to each other.

The present invention also provides an expression vector including a transcriptional regulatory element and a coding sequence operably linked to and under control of the transcriptional regulatory element, the transcriptional regulatory element including a promoter and a polynucleotide which is operably linked to the promoter and selected from the group consisting of: at least one polynucleotide selected from the group consisting of polynucleotides having the nucleotide sequences of SEQ ID NOS: 46 to 57; at least one polynucleotide selected from the group consisting of polynucleotides having the nucleotide sequences of SEQ ID NOS: 58 to 61; and at least one polynucleotide selected from the group consisting of polynucleotides having the nucleotide sequences of SEQ ID NOS: 46 to 57 operably linked to at least one polynucleotide selected from the group consisting of polynucleotides having the nucleotide sequences of SEQ ID NOS: 58 to 61.

Preferably, the expression vector may further include polynucleotides having the nucleotide sequences of SEQ ID NOS: 62 and 63 at the 5'- and 3'-ends of the coding sequence. The nucleotide sequences of SEQ ID NOS: 62 and 63 may be derived from 5' and 3' UTRs of FIX gene.

The coding sequence may be selected from the nucleotide sequences encoding liver-specific proteins including, but not limited to, albumin, α-fetoprotein, α-glucosidase, α1-antitrypsin, antithrombin, lipoproteins, ceruloplasmin, FVII, FVIII, FIX, erythropoietin, fibrinogen, glucocerebrosidase, haptoglobin, IGF-1, insulin, plasminogen, prothrombin, and transferrin.

The coding sequence is operably and controllably linked to a promoter, an enhancer, an intron, a UTR and an LCR.

As described above, an appropriate combination of the transcriptional regulatory elements of the present invention enables the liver tissue-specific expression of a target coding sequence, and contributes to mRNA stabilization, thereby resulting in improved expression of the coding sequence. An expression cassette or vector including various combinations of such transcriptional regulatory elements enables sustained expression of a target coding sequence in a liver tissue at a high level, and thus, can be broadly applied for the treatment of thrombosis, hemophilia, liver cancer, etc.

The following Examples are intended to illustrate the present invention without limiting its scope.

EXAMPLE 1

Isolation and Activity Analysis of Liver Tissue-specific Expression Promoters and Enhancers <Step 1> Isolation and Activity Analysis of Liver Tissue-specific Expression Promoters Genomic DNA was extracted from a cell lysate of human liver cell line (Chang cells) by using a DNeasy Tissue Kit (Qiagen). In order to isolate a FVII promoter, PCR was performed using the genomic DNA as a template, a primer set of SEQ ID NOS: 1 and 2, and DNA polymerase (Ex-Taq, Takara) to obtain a DNA fragment having the nucleotide sequence of SEQ ID NO: 41. Specifically, PCR was carried out under the following conditions: initial denaturation at 94° C. for five minutes; 30 cycles of denaturation at 94° C. for 30 seconds, annealing at 56° C. for 30 seconds and extension at 72° C. for one minute; and final extension at 72° C. for three minutes. The PCR products were purified by gel extraction and inserted into a pCR2.1-TOPO plasmid vector. The FVII promoter having the nucleotide sequence of SEQ ID NO: 41 was identified by a restriction enzyme cleavage map and sequence analysis. The plasmid containing the FVII promoter was designated "pCR-FVII pro." Further, PCR was carried out as described above except for using a primer set (SEQ ID NOS: 3 and 4) for an OATP-C promoter and a primer set (SEQ ID NOS: 5 and 6) for an AAT promoter, and the PCR products were inserted into pCR2.1-TOPO plasmid vectors. The OATP-C promoter having the nucleotide sequence of SEQ ID NO: 43 and the AAT promoter were identified by a restriction enzyme cleavage map and sequence analysis. The plasmids containing the OATP-C promoter and the AAT promoter were designated "pCR-OATP-C pro" and "pCR-AAT enh/pro," respectively. Schematic diagrams of pCR-FVII pro, pCR-OATP-C pro and pCR-AAT enh/pro are shown in FIG. 1A.

SV40 late poly(A) of a phRL-null vector (Promega) expressing *Renilla* luciferase was replaced with poly(A) of human growth hormone, and a T7 promoter and introns were removed therefrom to construct a pmRL-null vector. The pmRL-null vector was digested with BglII restriction enzyme and treated with a shrimp alkaline phosphatase.

The pCR-FVII pro and pCR-OATP-C pro plasmids were digested with BamHI. The obtained DNA fragments were purified by gel extraction and inserted into the previously prepared pmRL-null vectors. The desired DNA fragment was identified in each plasmid vector by a restriction enzyme cleavage map. The plasmid vectors were designated "pmRL-FVII Pro" and "pmRL-OATP-C Pro."

Meanwhile, an about 200 bp fragment of the 5'-end of the FVII promoter within the pmRL-FVII Pro was truncated using EcoRI restriction enzyme, followed by ligation to construct a pmRL-FVIIΔ Pro plasmid carrying a truncated FVII (FVIIΔ) promoter having the nucleotide sequence of SEQ ID NO: 42.

Figure 1B:
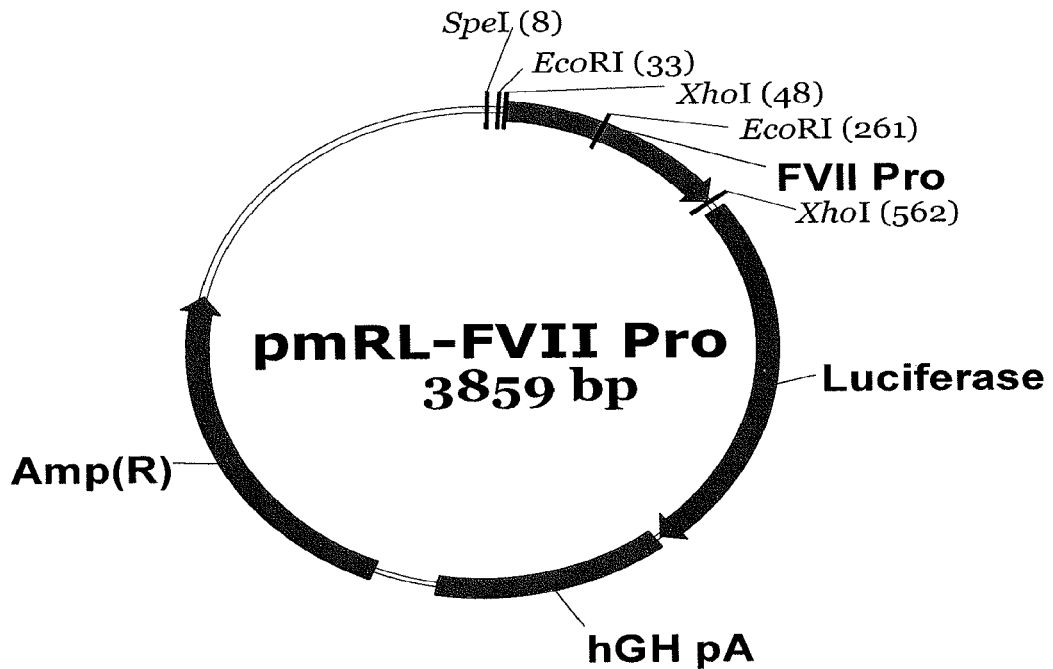
FIG. 1B: schematic diagrams of mRLuc luciferase expression vectors pmRL-FVII Pro, pmRL-FVIIΔ Pro and pmRL-OATP-C Pro containing FVII promoter, truncated FVII (FVIIΔ) promoter and OATP-C promoter, respectively.
Figure 1B:
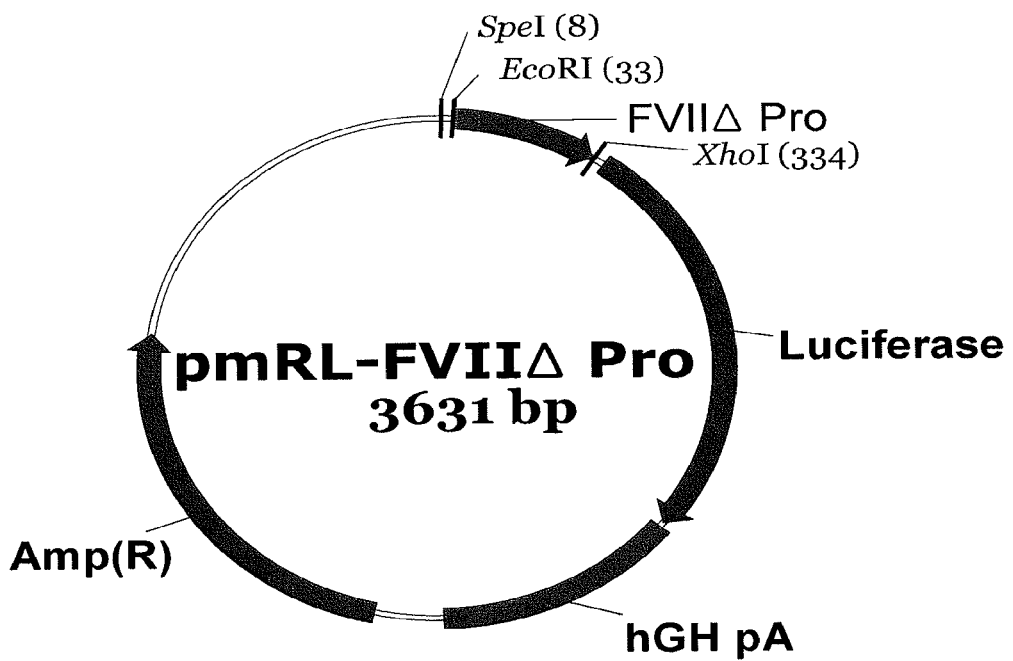
Figure 1B:
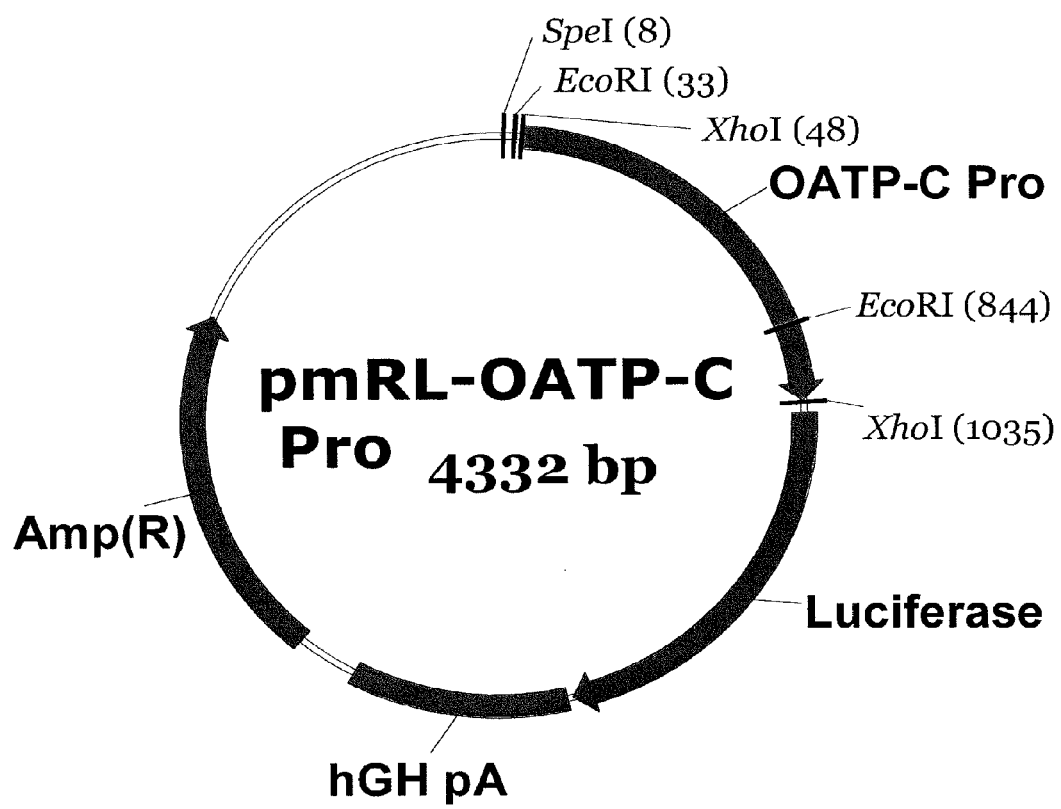

Schematic diagrams of pmRL-FVII Pro, pmRL-OATP-C Pro and pmRL-FVIIΔ Pro are shown in FIG. 1B.

Luciferase expression levels of the pmRL-FVII Pro, pmRL-FVIIΔ Pro and pmRL-OATP-C Pro were measured in human liver cell lines (Huh-7, HepG2, Hep3B), kidney cell line (HEK293), lung cancer cell line (A549) and cervical cancer cell line (HeLa). In detail, the cells were cultured in each well of a six-well plate using a polyethyleneimine (PEI) reagent (Polyplus, Illkirch, France) to reach 70 to 80% confluency. The cultured cells were transfected with each 2 µg of the pmRL-FVII Pro, pmRL-FVIIΔ Pro and pmRL-OATP-C Pro plasmids and 1 µg of a pcDNA-lacZ plasmid and cultured at 37° C. for 24 hours. The cells were harvested and centrifuged at 3,000 rpm for five minutes to separate cells and media. The cells were resuspended in 100 µl of a lysis buffer (25 mM Tris-phosphate, pH 7.8, 2 mM DTT (Dithiothreitol), 2 mM 1,2-diaminocyclohexane N,N,N,N'-tetra acetic acid, 10% glycerol, 1% Triton® X-100) followed by freezing and thawing (×3) to completely lyse the cells. The cell lysates were centrifuged at 10,000 rpm for one minute. The resultant supernatants were subjected to galactosidase assay and Bradford assay to normalize for transfection efficiency, and promoter activity was measured by luciferase activity assay. The results are shown in FIG. 2A.

Figure 2A:
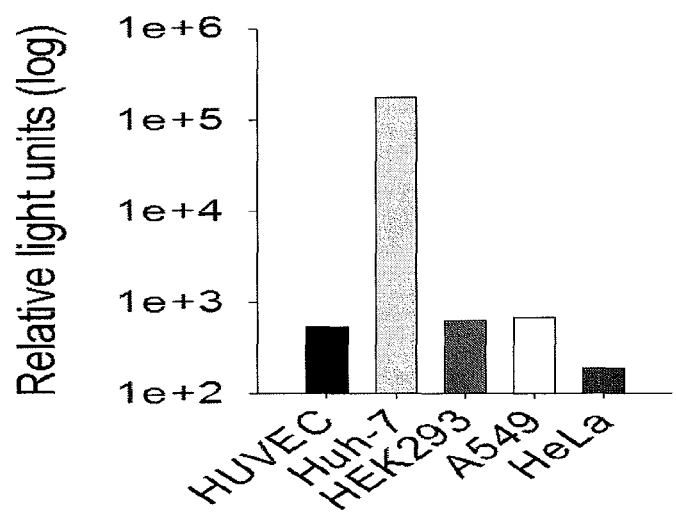
FIG. 2A: a histogram showing the expression efficiencies of FVII promoter and OATP-C promoter in: a human umbilical vein endothelial cell line (HUVEC); a human hepatocellular carcinoma cell line (Huh-7); a human kidney cell line (HEK293); a human lung adenocarcinoma epithelial cell line (A549); and a human cervical carcinoma cell line (HeLa)
Figure 2A:
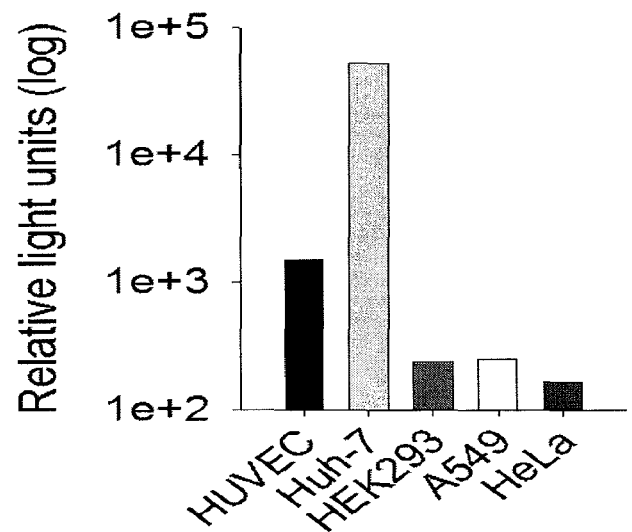

As shown in FIG. 2A, the FVII promoter and OATP-C promoter induced a higher luciferase expression specifically in the liver cell line Huh-7.

Figure 2B:
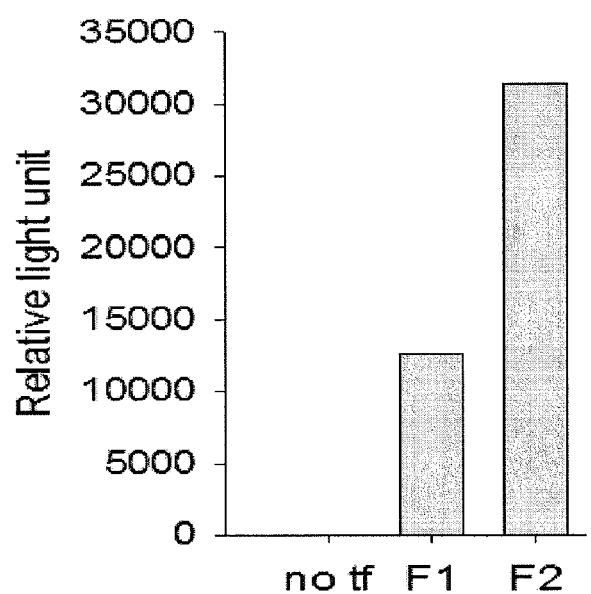
FIG. 2B: schematic diagrams of luciferase expression cassettes containing FVII promoter and FVIIΔ promoter, and a histogram comparing the expression efficiencies of the promoters.
Figure 2B:
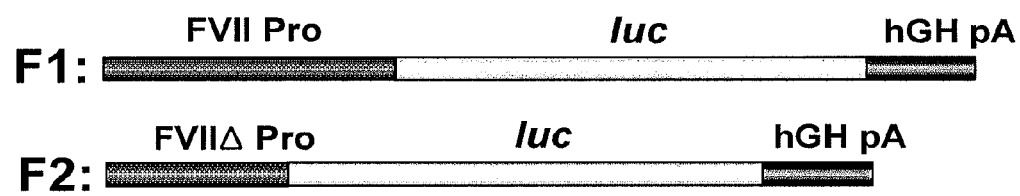

The FVIIΔ promoter showed a 2.5-fold higher activity than the FVII promoter in the Huh-7 cells (see FIG. 2B).

Figure 2C:
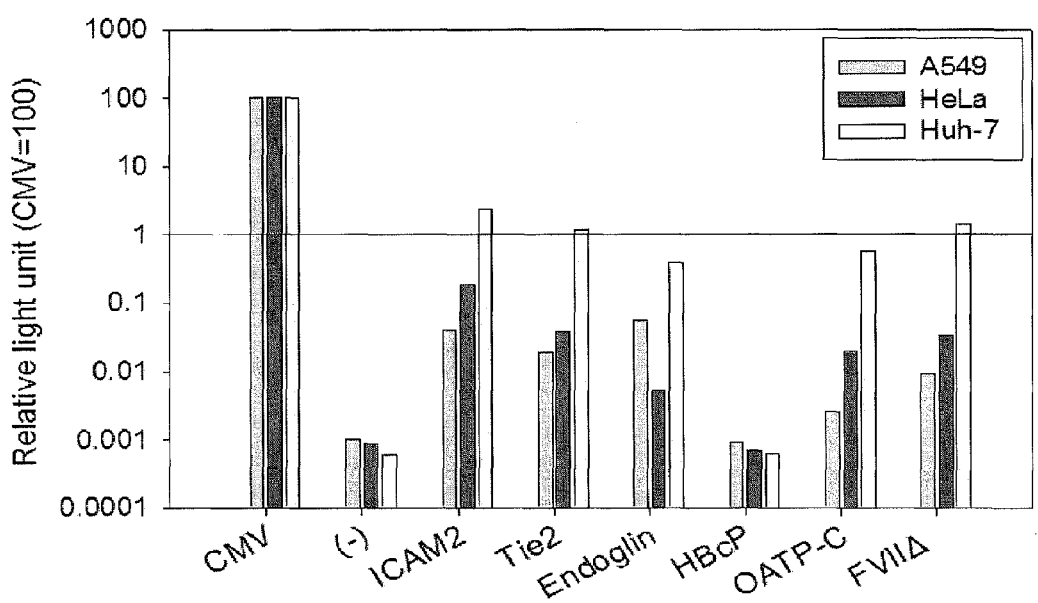
FIG. 2C: a histogram showing the expression efficiencies of FVIIΔ promoter, OATP-C promoter, hepatitis B virus core protein (HBcP) promoter, endoglin (Endoglin) promoter, cell adhesion molecule (ICAM2) promoter and tyrosine kinase receptor (Tie2) promoter, in a manner comparative with CMV promoter.

The FVIIΔ promoter showed 1.4% of the expression efficiency of a CMV promoter in the Huh-7 cells, and average 0.07% of the expression efficiency of the CMV promoter in the cell lines derived from other tissues than a liver tissue. However, unlike the CMV promoter, the specificity of the FVIIΔ promoter to the liver tissue was 20-fold higher than other tissues (see FIG. 2C). This result shows that the FVIIΔ promoter increases the expression efficiency of a target gene without adversely affecting the liver tissue specificity, and thus, is suitable for an expression vector which can be selectively operated in the liver tissue. In FIG. 2C, (−) represents a negative control (absence of a promoter), ICAM2 represents a promoter of an intracellular adhesion molecule, Tie2 represents a promoter of a tyrosine kinase receptor, Endoglin represents a promoter of endoglin, and HBcP represent a promoter of a hepatitis B virus core protein.

<Step 2> Isolation of Enhancers

Figure 3A:
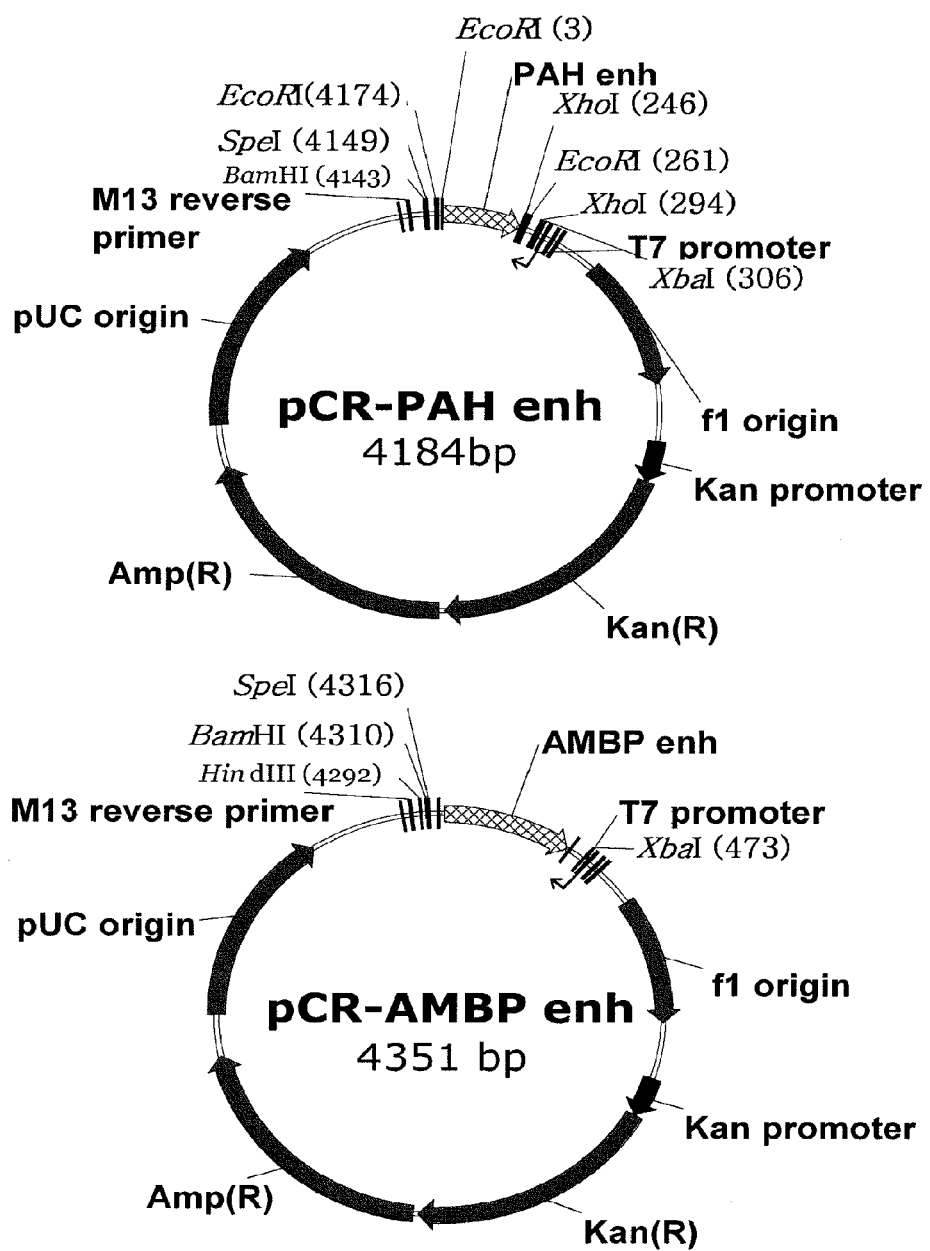
FIG. 3A: schematic diagrams of pCR-PAH enh and pCR-AMBP enh plasmids containing phenylalanine hydroxylase (PAH) enhancer and α1-microglobulin/bikunin precursor (AMBP) enhancer, respectively.

In order to isolate a PAH enhancer, PCR was performed as described in <step 1> except for using a primer set (SEQ ID NOS: 7 and 8) for the PAH enhancer. The PCR product was purified by gel extraction and inserted into a pCR2.1-TOPO plasmid vector. The PAH enhancer having the nucleotide sequence of SEQ ID NO: 44 was identified by a restriction enzyme cleavage map and sequence analysis. The plasmid was designated "pCR-PAHenh." Further, the above procedure was repeated except for using a primer set (SEQ ID NOS: 9 and 10) for an AMBP enhancer to construct a pCR-AMBPenh plasmid carrying the AMBP enhancer having the nucleotide sequence of SEQ ID NO: 45. Schematic diagrams of the pCR-PAHenh and pCR-AMBPenh plasmids are shown in FIG. 3A.

The PAH and AMBP enhancers were isolated by digesting the plasmids pCR-PAHenh and pCR-AMBPenh with SpeI and XbaI, purified by gel extraction, and inserted into the SpeI sites of the pmRL-FVIIΔPro and pmRL-OATP-C Pro vectors prepared in <step 1>. The pmRL-FVIIΔ Pro and pmRL-OATP-C Pro combined with the PAH enhancer were designated "pmRL-PF" and "pmRL-PO," respectively. The pmRL-FVIIΔ Pro and pmRL-OATP-C Pro combined with the AMBP enhancer were designated "pmRL-AF" and "pmRL-AO," respectively. The PAH enhancer was extracted from the pmRL-PF by using SpeI and XbaI, and inserted into the SpeI sites of the pmRL-AF and pmRL-AO. The resultant vectors were designated "pmRL-PAF" and "pmRL-PAO."

Figure 3B:
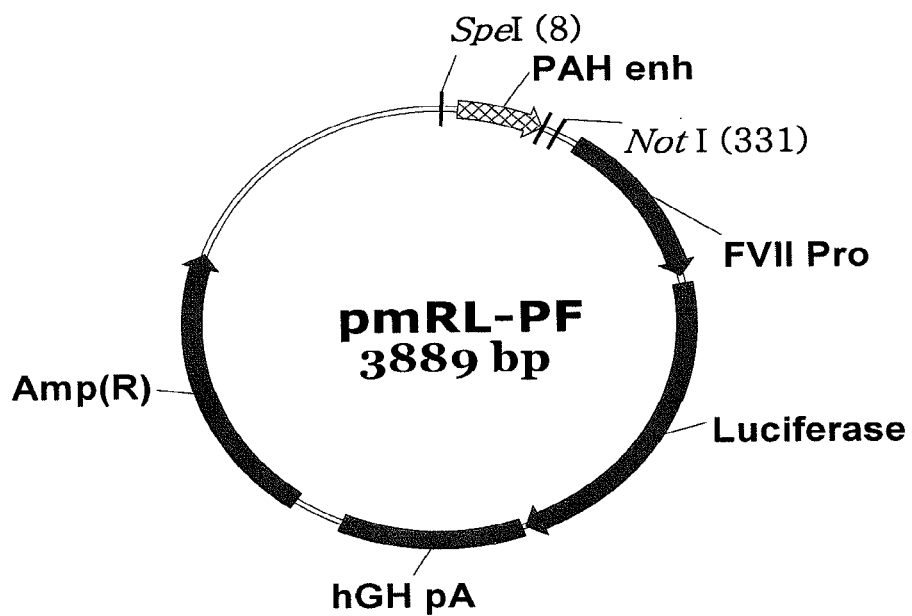
FIG. 3B: schematic diagrams of pmRL-PF, pmRL-AF, pmRL-PAF, pmRL-PO, pmRL-AO and pmRL-PAO expression vectors, which are constructed by inserting at least one selected from PAH enhancer and AMBP enhancer into pmRL-FVIIΔ Pro expression vector containing FVIIΔ promoter or pmRL-OATP-C Pro expression vector containing OATP-C promoter.
Figure 3B:
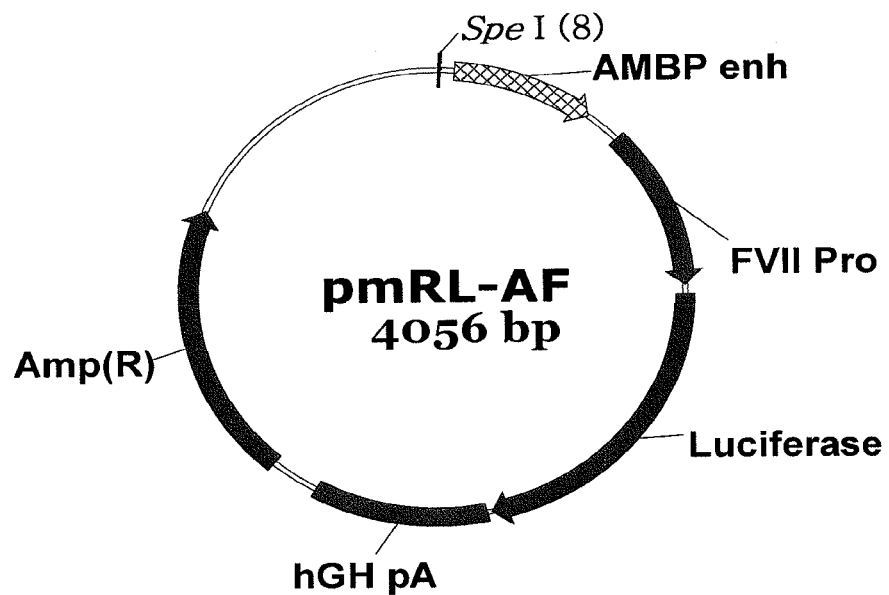
Figure 3B:
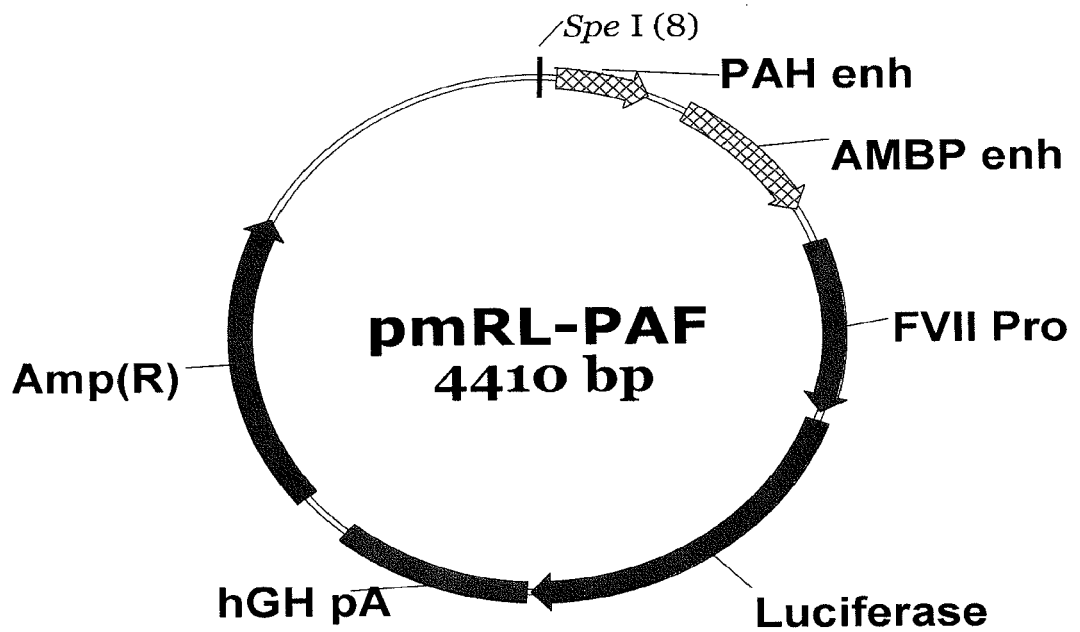
Figure 3B:
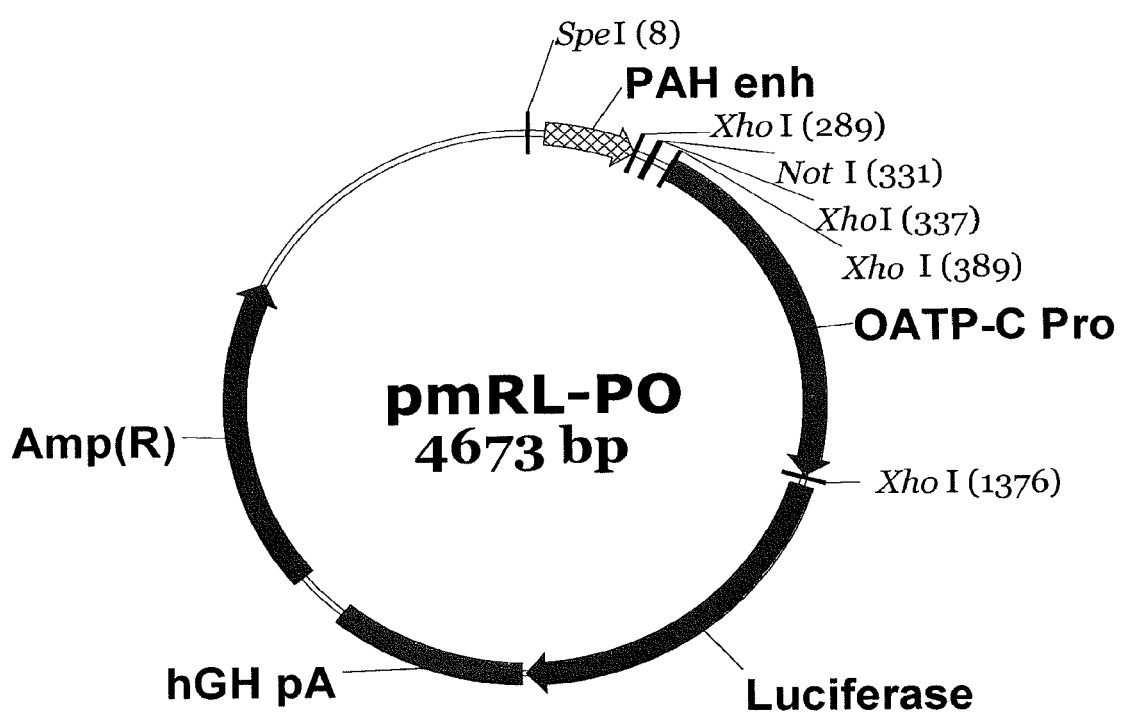
Figure 3B:
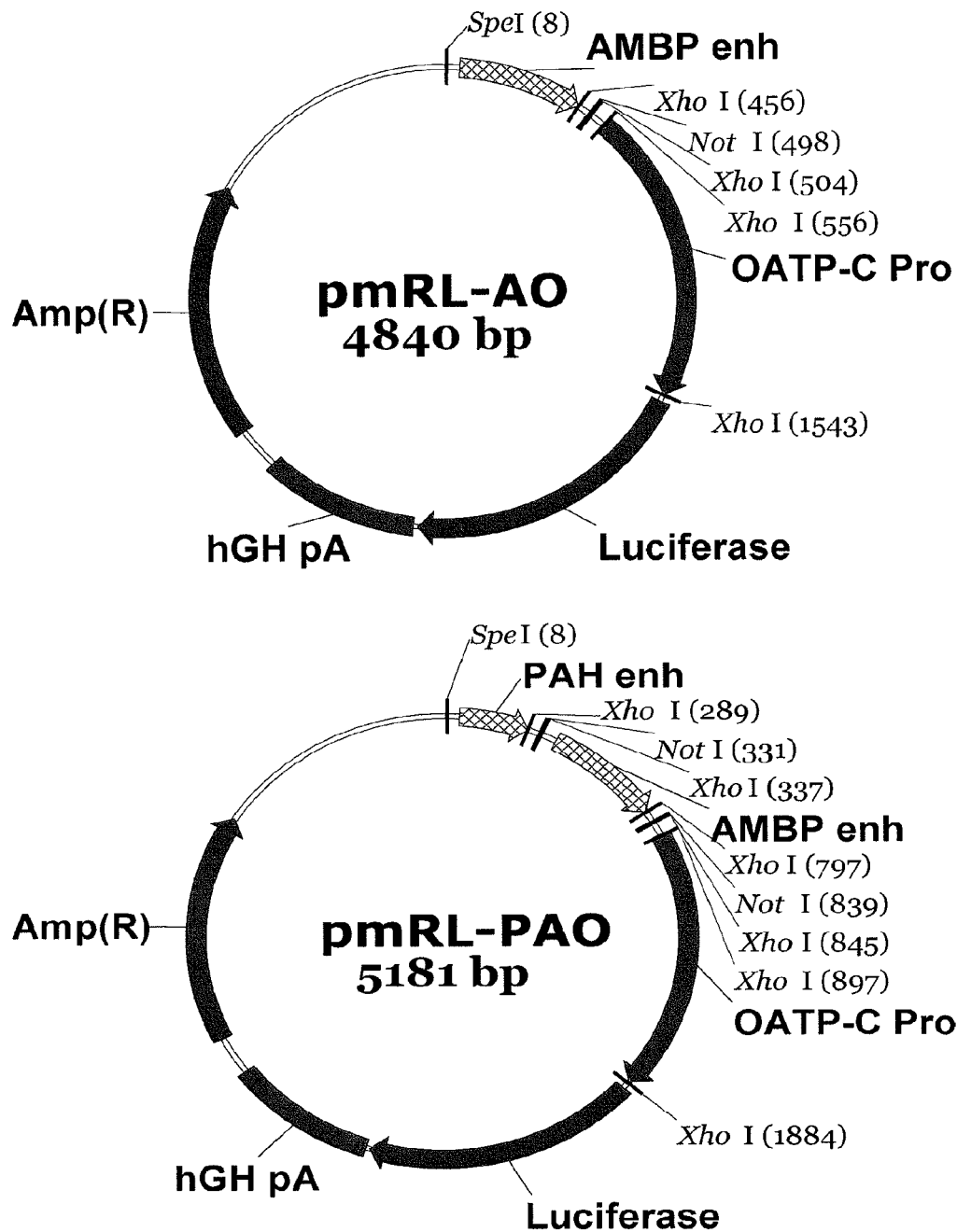

Schematic diagrams of the pmRL-PF, pmRL-PO, pmRL-AF, pmRL-AO, pmRL-PAF and pmRL-PAO vectors are shown in FIG. 3B.

CMV and SV40 enhancers, which can improve promoter activity in a tissue-nonspecific manner, were inserted into upstream of the OATP-C and FVII promoters according to the above-described procedure.

<Step 3> Analysis of Expression Efficiency of Target Gene According to Combination of Promoter and Enhancer
<3-1> In Vitro Test The gene expression efficiencies for the vectors constructed in <step 2> were measured in a human liver cell line (Huh-7) and control cell lines, i.e., a human lung cell line (A549) and a human cervical cancer cell line (HeLa), in the same manner as in <step 1>. The results are shown in FIG. 4A.

Figure 4A:
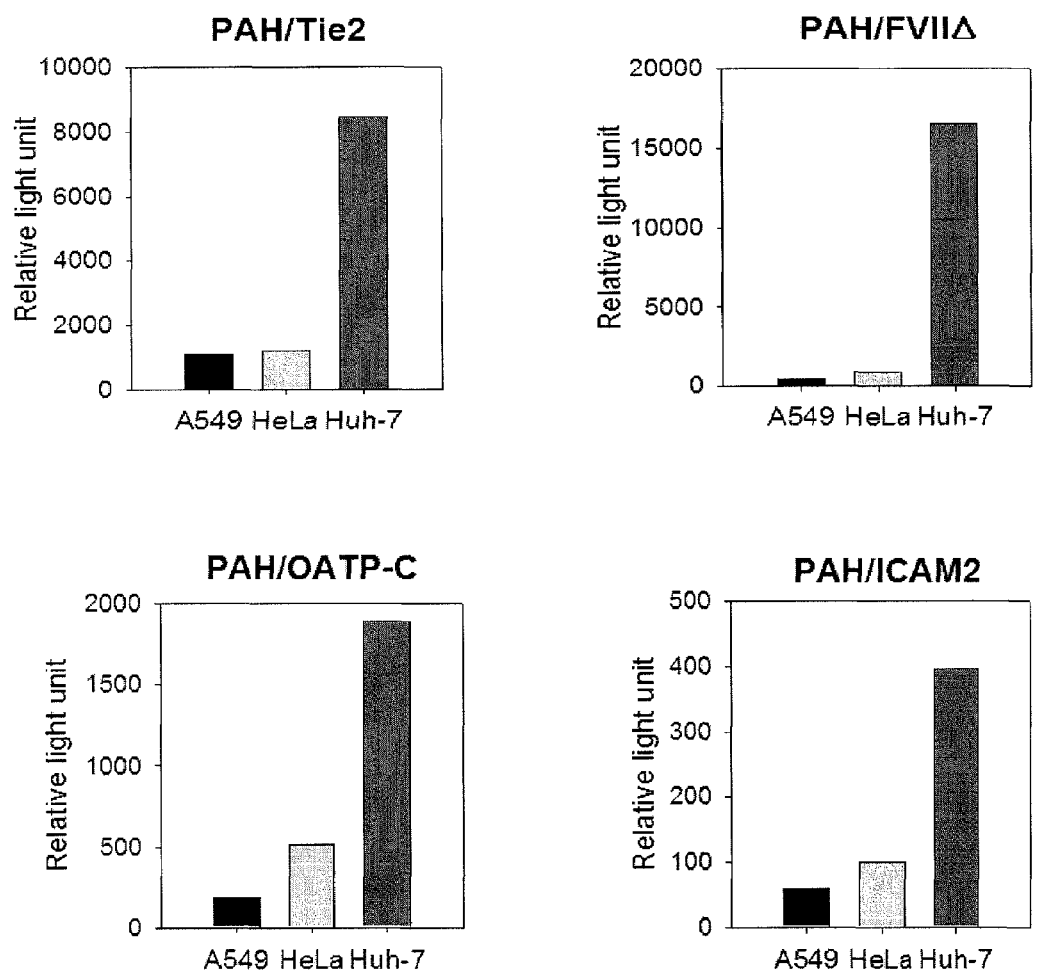
FIG. 4A: histograms showing the in vitro luciferase expression levels in A549, HeLa and Huh-7 depending on the variation in the mode of combination of PAH enhancer and AMBP enhancer with FVIIΔ, OATP-C, Tie-2 and ICAM2 promoters.
Figure 4A:
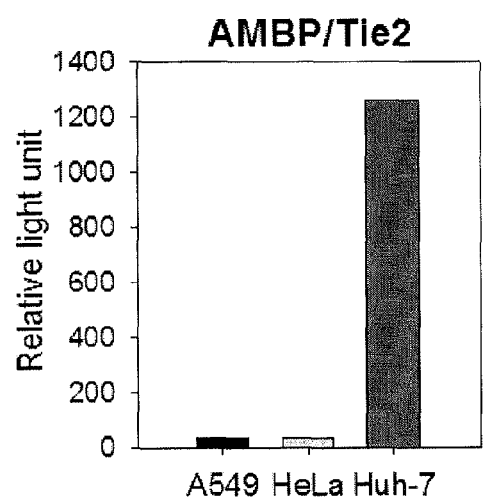
Figure 4A:
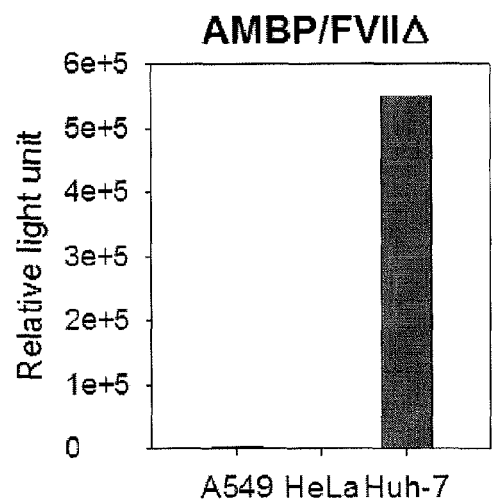
Figure 4A:
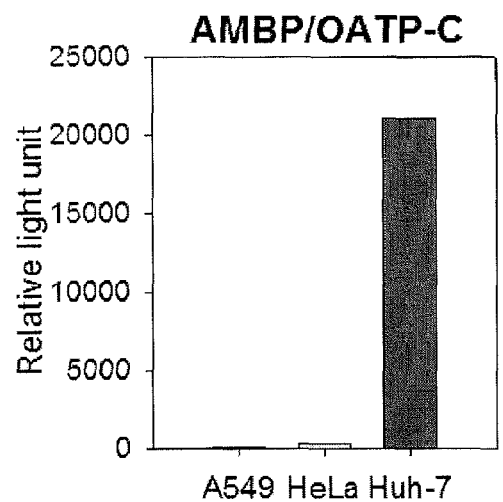
Figure 4A:
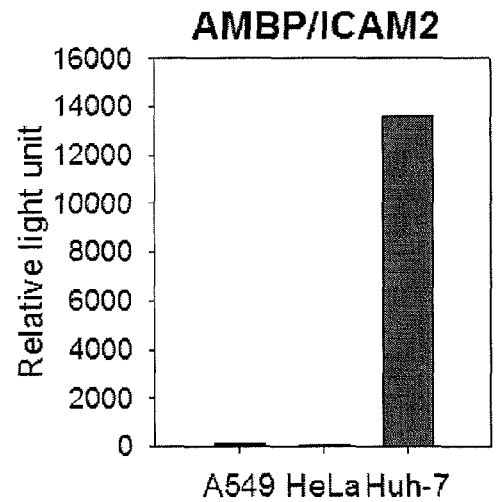

As shown in FIG. 4A, the specificity of the vector carrying the PAH enhancer and FVIIΔ promoter in the liver cell line Huh-7 was average 28.4-fold higher than that in the other cell lines. This shows that the tissue-specificity of the FVIIΔ promoter was increased 1.42-fold by the PAH enhancer. The tissue-specificity of the FVIIΔ promoter was increased 213.7-fold or more by the AMBP enhancer, which is about 3-fold higher than an increase (65.6-fold) of the tissue-specificity of the OATP-C promoter by the AMBP enhancer. The results show that liver-selectivity of the FVIIΔ promoter can be significantly enhanced by an enhancer.

In order to measure the activity of the expression vector controlled under the AMBP enhancer and the FVIIΔ promoter relative to that of the expression vector controlled under the CMV promoter, a luciferase expression level was measured in human liver cell lines (Huh-7, Hep3B) and control cell lines, i.e., a kidney cell line (HEK293), a lung cancer cell line (A549), a cervical cancer cell line (HeLa) and a vascular endothelial cell line (HUVEC). The results are shown in FIG. 4B.

Figure 4B:
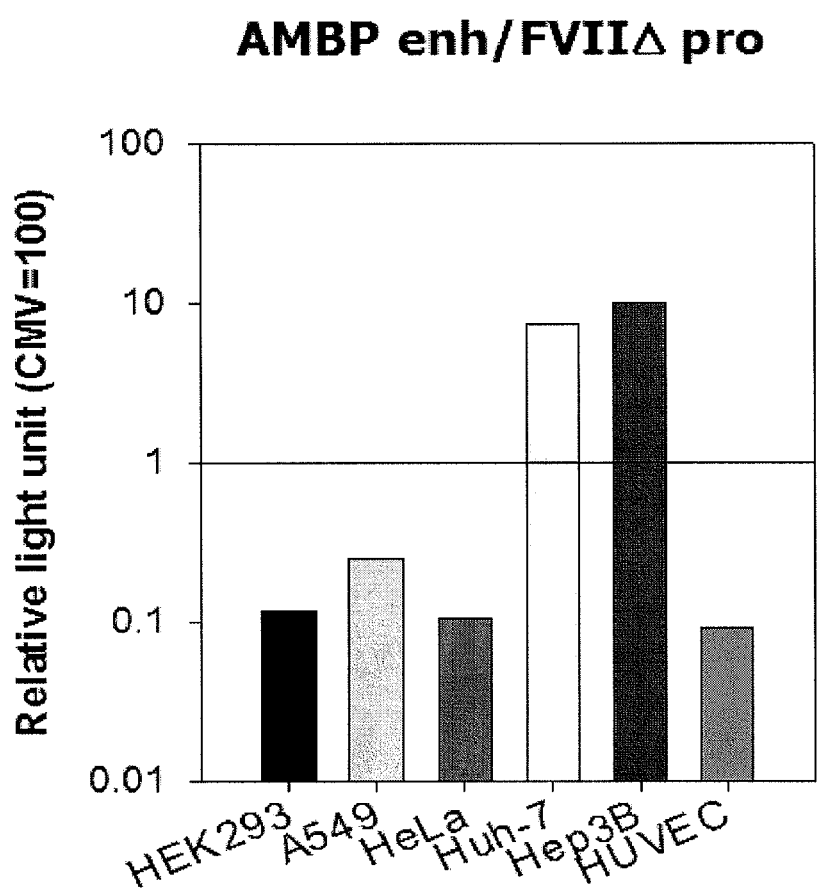
FIG. 4B: a histogram showing the luciferase expression efficiencies and liver specificities in HEK293, A549, HeLa, Huh-7, human hepatoma cell line (Hep3B) and HUVEC when AMBP enhancer was combined with FVII promoter, in a manner comparative with a CMV promoter.

As shown in FIG. 4B, in the liver cell lines, the expression vector containing the AMBP enhancer and the FVIIΔ promoter showed 8.7% of the luciferase expression efficiency of the expression vector containing the CMV promoter, and in the other cell lines, average 0.14% of the luciferase expression efficiency of the expression vector containing the CMV promoter. This shows that the liver tissue-specificity of the expression vector containing the AMBP enhancer and the FVIIΔ promoter is about 62-fold higher than the other tissues.

<3-2> In Vivo Test

In order to measure the in vivo gene expression efficiency in the liver, each complex of the pmRL plasmids of <step 2> with polyethyleneimine (PEI) (Polyplus, Illkirch, France) or in vivo jetPEI (Polyplus, Illkirch, France) was injected into a mouse tail vein. Two days later, the liver was extracted from the mouse, and a luciferase expression level was measured.

In detail, each 40 µg of the pmRL-PO, -PF, -AO and -AF plasmids and 10 µg of a pcDNA-LacZ plasmid were injected into the tail veins of mice (six weeks old) in the form of a complex with PEI or In vivo jetPEI in a 5% glucose solution. Two days later, the liver, kidney, heart, spleen and lung tissues were extracted from the mice and homogenized in a PBS solution with a homogenizer. Then, 500 µl of the resultant tissue solution was mixed with 500 µl of a 2× lysis buffer (50 mM Tris-phosphate, pH 7.8, 4 mM DTT (Dithiothreitol), 4 mM 1,2-diaminocyclohexane N,N,N,N'-tetra acetic acid, 20% glycerol, 2% Triton® X-100) followed by freezing and thawing (×3) to completely lyse the cells. The cell lysates were centrifuged at 10,000 rpm for one minute. The resultant supernatants were subjected to galactosidase assay and Bradford assay to normalize for transfection efficiency, and gene expression efficiency was measured by luciferase activity assay. The results are shown in FIG. 4C.

Figure 4C:
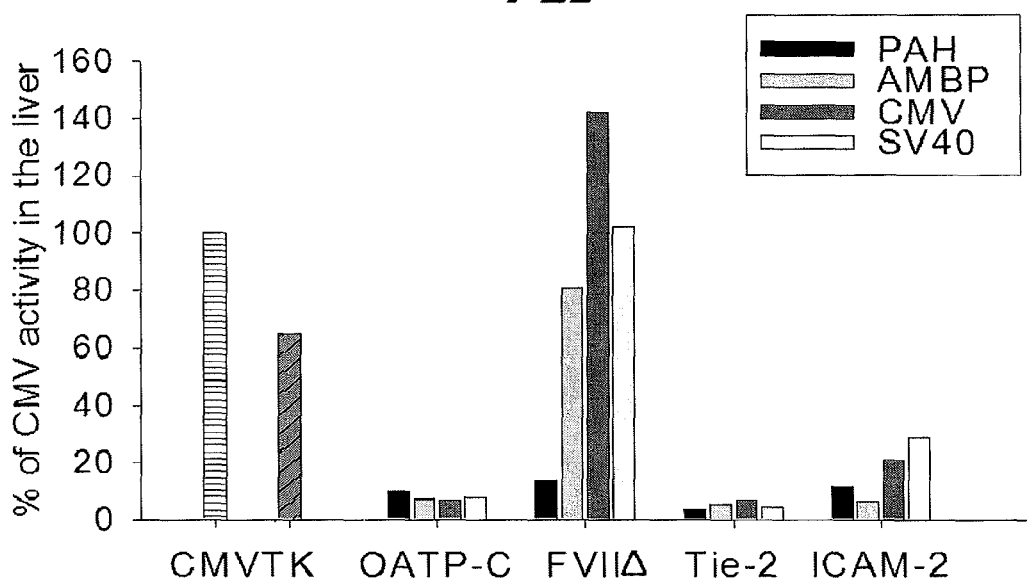
FIG. 4C: histograms showing the luciferase expression efficiencies in liver tissues for expression vectors carrying expression cassettes containing PAH enhancer, AMBP enhancer, CMV enhancer and SV40 enhancer together with the promoters shown in FIG. 4A after a mixture of each expression vector with polyethyleneimine (PEI) or in vivo jetPEI was injected into a mouse tail vein.
Figure 4C:
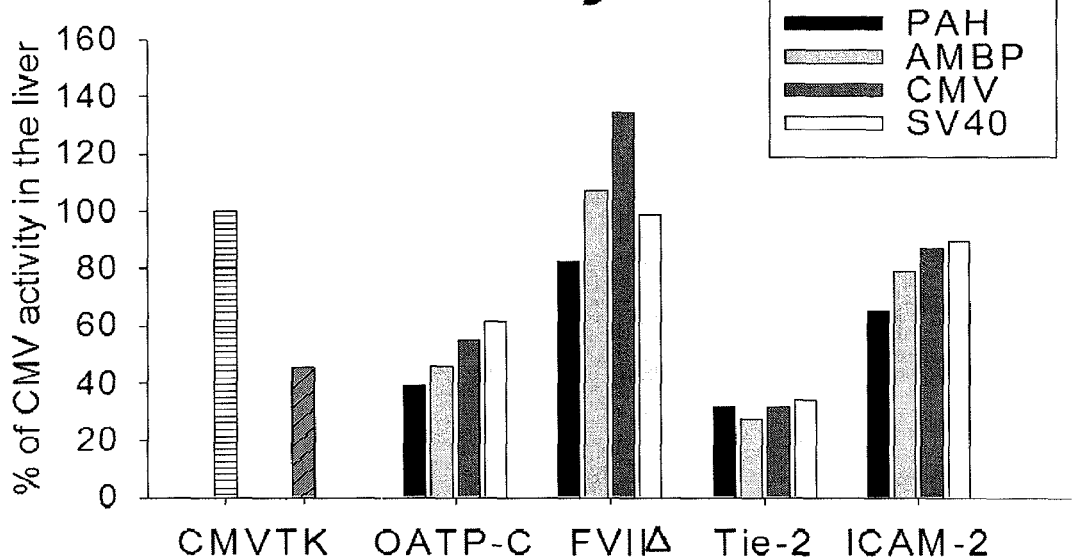

As shown in FIG. 4C, in the liver tissue, a luciferase expression level induced by the complex of the expression vector containing FVIIΔ promoter/PAH enhancer and PEI was equal to 14% of that induced by the CMV promoter, which is 14-fold or more higher than that of in vitro assay of luciferase expression. A liver-specific luciferase expression level induced by FVIIΔ promoter/AMBP enhancer was equal to 80% of that induced by the CMV promoter, which is 10-fold or more higher than that of in vitro assay of luciferase expression.

Using in vivo jetPEI instead of PEI increased the gene expression efficiency in the liver. Specifically, a liver-specific luciferase expression level induced by the complex of the expression vector containing OATP-C promoter/PAH enhancer and in vivo jetPEI was equal to about 38% of that induced by the CMV promoter, and a luciferase expression level induced by FVIIΔ promoter/PAH enhancer was equal to about 80% of that induced by the CMV promoter. The liver-specific luciferase expression level induced by the complex of FVIIΔ promoter/AMBP enhancer and in vivo jetPEI was similar to that induced by the CMV promoter. These results show that the activities of the inventive promoters and enhancers are better in vivo than in vitro.

EXAMPLE 2

Isolation of UTRs of hFIX and Introns of Liver-specific Genes, and Analysis of Gene Expression Efficiency by UTRs and Introns <Step 1> Identification of UTRs of hFIX, and Construction of Expression Vectors Including UTRs 1.2 mg of total RNA was extracted from 1 g of a human liver tissue, which was previously homogenized with a homogenizer, using a RNA extraction kit (Pharmacia Biotech). A single-stranded DNA was synthesized using the extracted RNA as a template, an M-MuLV reverse transcriptase (Takara) and oligo-dT17 primers (Takara), and a double-stranded cDNA was synthesized from the single-stranded DNA using DNA polymerase I (Takara).

In order to evaluate the effect of FIX UTR on gene expression efficiency, PCR was performed using the cDNA as a template, a primer set (SEQ ID NOS: 11 and 12) designed from a nucleotide sequence of FIX (Genbank accession No: NM000133) and Ex-Taq to obtain FIX cDNA including 5'UTR (SEQ ID NO: 62) and 3'UTR (SEQ ID NO: 63). The PCR condition was as follows: initial denaturation at 94° C. for five minutes; 30 cycles of denaturation at 94° C. for one minute, annealing at 56° C. for one minute and extension at 72° C. for one minute and 30 seconds; and final extension at 72° C. for three minutes.

The above procedure was repeated except for using a primer set of SEQ ID NOS: 13 and 14 to obtain FIX cDNA including no UTR as a control.

The amplified DNA fragments were digested with restriction enzymes NotI and SalI, purified by gel extraction, and inserted into NotI and SalI restriction sites of pBluescript SK(+) vectors. The FIX including the desired UTRs and the FIX including no UTR were identified by a restriction enzyme cleavage map and sequence analysis. The vectors were designated "pBS-hFIXUTR" and "pBS-hFIX," respectively (see FIG. 5(a)).

<Step 2> Isolation of Introns of Liver-specific Genes and Construction of Expression Vectors Including the Introns <2-1> Construction of pCR-int First, PCR was performed to obtain fragments including about 300 bp of 5'-ends of introns 1 of human antithrombin, plasminogen and prothrombin.

In detail, PCR was performed using the genomic DNA described in <step 1> of Example 1 as a template, and primer sets for human antithrombin intron (SEQ ID NOS: 15 and 16), human plasminogen intron (SEQ ID NOS: 17 and 18) and human prothrombin intron (SEQ ID NOS: 19 and 20) under the following conditions: initial denaturation at 94° C. for five minutes; 30 cycles of denaturation at 94° C. for one minute, annealing at 60° C. for one minute and extension at 72° C. for two minutes and 30 seconds; and final extension at 72° C. for three minutes. The PCR products were purified by gel extraction and inserted into pCR2.1-TOPO vectors. The introns of SEQ ID NOS: 46, 47 and 48 were identified by a restriction enzyme cleavage map and sequence analysis. The plasmids were designated "pCR-ATint," "pCR-PLAint" and "pCR-PTint," respectively.

Further, in order to isolate the intron 1 of FIX reported by Kurachi S, the above PCR procedure was repeated except for using a primer set (SEQ ID NOS: 21 and 22) for the intron 1 of FIX, and the obtained PCR product was inserted into a pCR2.1-TOPO vector. The resulting plasmid vector was digested with restriction enzyme PvuI or ScaI, and self-ligated. The FIX introns having different sizes were identified by a restriction enzyme cleavage map and sequence analysis. The plasmids were designated "pCR-1.4kbFIXint" and "pCR-0.3kbFIXint," respectively.

<2-2> Construction of pBS-FIX-Syn1int

The intron fragments of the pCR-ATint, pCR-PLAint and pCR-PTint prepared in <2-1> were inserted between exons 1 and 2 of FIX.

In detail, PCR of <2-1> was repeated except for using a sense primer (SEQ ID NO: 11) for FIX 5'UTR and an antisense primer (SEQ ID NO: 23) for consensus splicing donor sequence GTAA and G-triple motif derived from intron 2 of human α-globin to obtain a DNA fragment including FIX 5'UTR and exon 1, splicing donor and human α-globin G-triple motif. Further, the above PCR was repeated except for using a sense primer (SEQ ID NO: 24) for the branch sequence of human plasminogen and consensus splicing acceptor sequence TCGA and an antisense primer (SEQ ID NO: 12) for FIX 3'UTR to obtain a DNA fragment including the branch sequence, splicing acceptor, exons 2 to 8 and 3'UTR of FIX. The PCR products were purified by gel extraction and inserted into pCR2.1-TOPO vectors. The desired DNA fragments were identified by a restriction enzyme cleavage map and sequence analysis. The plasmids were designated 'pCR-5'hFIX" and "pCR-3' hFIX," respectively.

Figure 5:
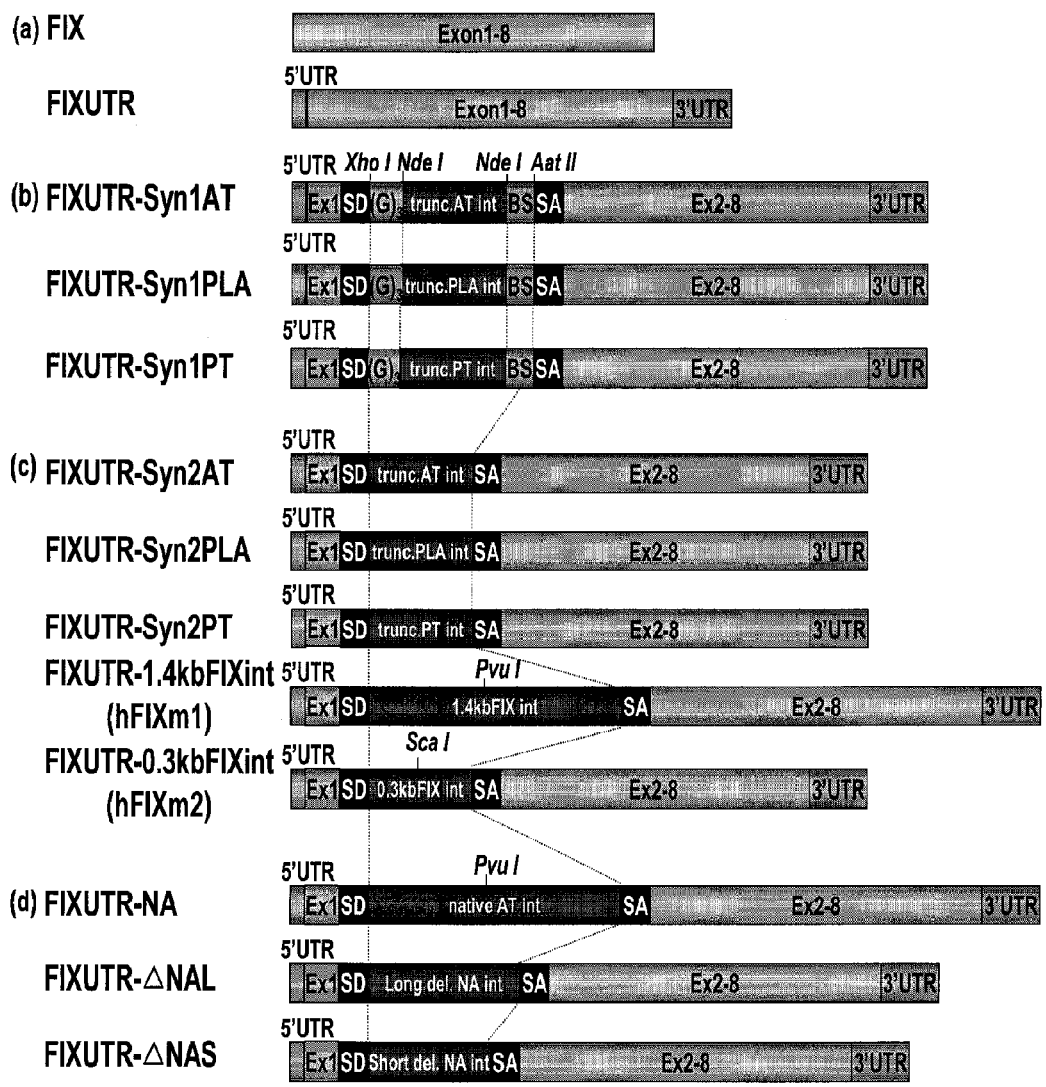
FIG. 5: schematic diagrams of hFIX expression plasmid including no UTR (FIX) and hFIX expression plasmid containing UTRs (FIXUTR)((a)), and FIXUTR plasmids containing various introns ((b), (c) and (d)) (SD, splicing donor; SA, splicing accepter; (G)$_3$, triple guanine motif; BS, branch sequence)

The pCR-5' hFIX and pCR-3' hFIX were digested with restriction enzymes NotI and NdeI, and NdeI and SalI, respectively, and both were simultaneously inserted into NotI and SalI restriction sites of pBluescript. The resulting plasmids were digested with NdeI, and the pCR-ATint, pCR-PLAint and pCR-PTint of <2-1> pretreated with the same enzyme, NdeI were inserted thereto. The desired introns of SEQ ID NOS: 49, 50 and 51 were identified by a restriction enzyme cleavage map and sequence analysis. The plasmids were designated "pBS-hFIXUTR-Syn1AT," "pBS-hFIXUTR-Syn1PLA" and "pBS-hFIXUTR-Syn1PT," respectively. Schematic diagrams of the plasmids are shown in FIG. 5 (b).

<2-3> Construction of pBS-FIX-Syn2int

The pBS-FIXUTR-Syn1PLA plasmid of <2-2> was digested with XhoI and AatII for the XhoI and AatII restriction sites adjacent to the splicing donor and acceptor, and the pCR-ATint, pCR-PLAint, pCR-PTint, pCR-1.4kbFIXint and pCR-0.3kbFIXint of <2-1> pretreated with the same enzymes, XhoI and AatII were inserted thereto. The introns of Syn2AT, Syn2PLA and Syn2PT (SEQ ID NOS: 52, 53 and 54) and introns of 1.4kbFIXint and 0.3kbFIXint were identified by a restriction enzyme cleavage map. The plasmids were designated "pBS-hFIXUTR-Syn2AT," "pBS-hFIXUTR-Syn2PLA," "pBS-hFIXUTR-Syn2PT," "pBS-hFIXUTR-1.4kbFIXint (hFIXm1)" and "pBS-hFIXUTR-0.3kbFIXint (hFIXm2)," respectively. Schematic diagrams of the plasmids are shown in FIG. 5 (c).

<2-4> Isolation of Full-length Intron 1 of Antithrombin and Construction of Shortened Antithrombin Introns The PCR of <2-1> was repeated except for using a primer set of SEQ ID NOS: 15 and 25 to amplify a fragment including full-length intron 1 of antithrombin. About 2.3 kb PCR products were inserted into pCR2.1-TOPO vectors, which were designated "pCR-NAint." The resulting plasmids were digested with XhoI and AatII, and inserted into pBS-hFIX-UTR according to the procedure of <2-3> to obtain pBS-hFIXUTR-NA including the intron of SEQ ID NO: 55.

The intron inserted into pBS-hFIXUTR-NA was truncated from PvuII site using a Kilo-Sequence Deletion Kit (Takara). Specifically, pBS-FIXUTR-NA was digested with PvuII, degraded with exonuclease III for 15 sec, 30 sec, 45 sec and 1 min at 25° C., end-blunted with Mung Bean nuclease and klenow enzyme, and self-ligated. The resultant constructs were transformed into E. coli. The obtained transformants were cultured in an ampicilin plate, single colonies were selected therefrom, and the sizes of the introns of the plasmids derived from the colonies were determined by electrophoresis using restriction enzymes. The plasmids carrying proper-sized introns were purified and sequenced to obtain the plasmids pBS-hFIXUTR-ΔNAL including a 811 bp intron of SEQ ID NO: 56 and pBS-hFIXUTR-ΔNAS including a 640 bp intron of SEQ ID NO: 57. Schematic diagrams of the plasmids pBS-hFIXUTR-NA, pBS-hFIXUTR-ΔNAL and pBS-hFIXUTR-ΔNAS are shown in FIG. 5 (d).

<Step 3> Analysis of Effects of UTRs and Introns on FIX Expression

The pBS-hFIX, pBS-hFIXUTR, pBS-hFIXUTR-Syn1int (AT, PLA, PT) and pBS-hFIXUTR-Syn2int (AT, PLA, PT, 1.4kbFIXint, 0.3kbFIXint) plasmids prepared in <step 1> and <step 2> were digested with NotI and SalI, and inserted into pTRUF6 adeno-associated virus vectors containing a CMV promoter and bovine poly(A) to obtain hFIX expression vectors, CMV-hFIX, CMV-hFIXUTR, CMV-hFIXUTR-Syn1int (AT, PLA, PT) and CMV-hFIXUTR-Syn2int (AT, PLA, PT, 1.4kbFIXint, 0.3kbFIXint).

25 μg of the plasmid DNAs of the above expression vectors were injected into C57BL/6 mouse tail veins. The next day, blood samples were collected and used in the following ELISA.

The obtained blood samples were diluted 100 times in a HBS-BSA-EDTA-T20 buffer (0.1M HEPES-0.1M NaCl-1% BSA-10 mM EDTA-0.1% Tween-20). The diluted blood samples were added to a 96-well plate coated with human FIX (hFIX) antibody (Affinity Biologicals), cultured at room temperature for 90 minutes, washed with PBS-0.1% Tween-20, and incubated with a secondary antibody labeled with peroxidase. The plate was washed again with PBS-0.1% Tween-20, and a substrate buffer containing dissolved O-phenyldiamine and $H_2O_2$ was added thereto. The plate was incubated for five minutes, and the reaction was stopped with 2.5M $H_2SO_4$. The absorbance was measured at 490 nm with a spectrophotometer (Spectra Shell Microplate Reader, STL Spectra, Milan, Italy), and hFIX concentrations of the samples were calculated according to a standard curve of a standard absorbance versus a standard concentration. The results are shown in FIG. 6A.

Figure 6A:
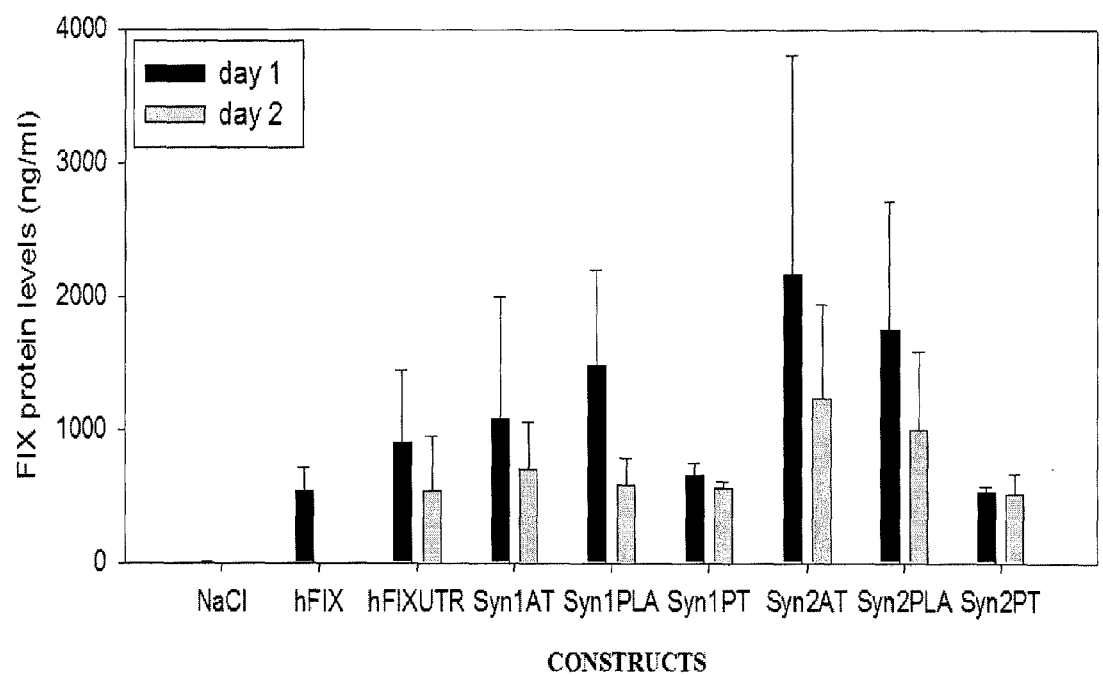
FIG. 6A: ELISA results showing the expression level of hFIX protein in the plasma samples obtained from the mice injected through tail vein with the expression vectors carrying CMV-hFIXUTR-Syn1int, CMV-hFIXUTR-Syn2int, CMV-hFIX and CMV-hFIXUTR expression cassettes.

As shown in FIG. 6A, the day after injection, blood concentration of hFIX protein induced by CMV-hFIXUTR was about 910 ng/ml that is about 1.7-fold higher than that (540 ng/ml) of the protein induced by CMV-hFIX including no UTR. This shows that the UTR contributes to the expression of hFIX.

The hFIX expression level (1,480 ng/ml) of CMV-hFIX-UTR-Syn1PLA was up to 1.6-fold of that (910 ng/ml) of CMV-hFIXUTR, and the hFIX expression level (2,170 ng/ml) of CMV-hFIXUTR-Syn2AT was up to 2.4-fold of that (910 ng/ml)) of CMV-hFIXUTR. This shows that the intron is involved in hFIX gene expression and initial hFIX protein induction.

Meanwhile, recombinant adeno-associated viruses rAAV-CMV-hFIX, rAAV-CMV-hFIXUTR and rAAV-CMV-hFIX-UTR-Syn1int (AT, PLA, PT) were produced using the expression vectors CMV-hFIX, CMV-hFIXUTR and CMV-hFIXUTR-Syn1int (AT, PLA, PT). Specifically, 200 ml of HEK293T cells, which were adapted to a concentration of $1 \times 10^6$ cells/ml using low calcium DMEM medium (0.1 mM $Ca^{++}$, 0.1% PL-68, 1% FBS), were prepared in a 500 ml Spinner flask. A DNA-PEI mixture including 33 μg of each expression vector, 167 μg of adenovirus helper plasmid pDG and 650 μl of 10 μM PEI was loaded on the cells, and the cells were suspension-cultured in a 5% $CO_2$ incubator at 30 rpm for six hours. Then, the culture medium was replaced with 100 μg dextran sulfate-low calcium DMEM. After 48-hour culture, the cells were harvested, subjected to freezing and thawing (×3) and centrifuged at 2000 rpm for 5 minutes. The resultant supernatants were purified by iodixanol gradient ultracentrifugation (Zolotukhin, S. et al, Gene Ther., 6: 973-985 (1999)). $1 \times 10^9$ infectious particles (IP) were injected into tail veins of immunodeficient nude mice (Japan SLC Inc). After two weeks, blood samples were collected every week and subjected to ELISA according to the above-described method. The results are shown in FIG. 6B.

Figure 6B:
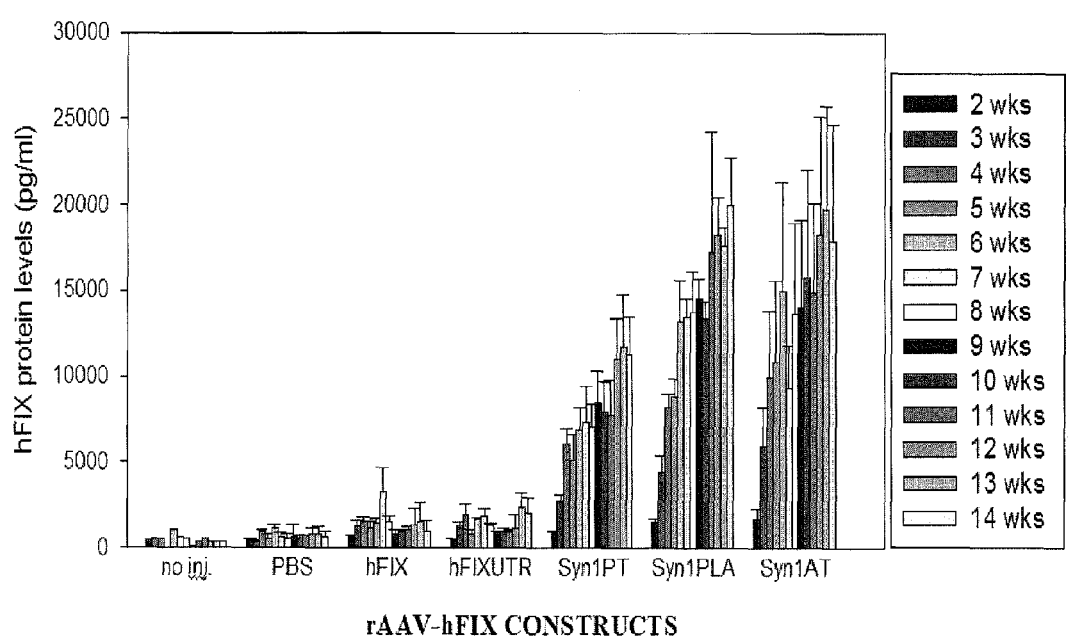
FIG. 6B: ELISA results showing the expression level of hFIX protein in the plasma samples obtained every week from immunodeficient mice in which $1 \times 10^9$ infectious particles (IP) of recombinant adeno-associated viruses carrying CMV-hFIXUTR-Syn1int expression cassettes are injected.

As shown in FIG. 6B, at 14 weeks after virus injection, the hFIX expression levels of the viruses including the inventive introns were 10 to 20-fold higher than that of the virus including no intron. Specifically, the hFIX protein concentration of the virus carrying CMV-hFIXUTR-Syn1AT was 19,996 pg/ml, while the hFIX protein concentration of the virus carrying CMV-hFIXUTR was 2,024 pg/ml. This shows that the inventive introns play critical roles in enhanced gene expression.

<Step 4> Analysis of Luciferase Expression Efficiency and mRNA Stability by Introns <4-1> Introduction of Intron into Luciferase Expression Vector Controlled by TK Promoter A pRL-TK expression vector (promega) was digested with HindIII/NheI to remove a SV40 intron, blunt-ended and self-ligated. The intron-truncated pRL-TK vector was designated "pRL-Δint" and the SV40 intron-containing pRL-TK vector was designated "pRL-SV40."

Figure 7A:
FIG. 7A: a schematic diagram showing a luciferase expression cassette containing an intron into RLuc luciferase gene controlled under TK promoter.

The pBS-hFIXUTR-Syn1AT, pBS-hFIXUTR-Syn1PLA and pBS-hFIXUTR-0.3kbFIXint obtained in <2-2> and <2-3> were digested with XhoI/AatII and blunt-ended. The resultant fragments were inserted into the above expression vector pRL-Δint. The resulting vectors were designated "pRL-Syn1AT," "pRL-Syn1PLA" and "pRL-hFIXm2," respectively (see FIG. 7A).

<4-2> Analysis of Luciferase Expression Efficiency

A complex of 2 μg of the luciferase expression vectors of <4-1>, 1 μg of a β-galactosidase expression vector and 6 μg of PEI (polyplus) was injected into liver cell line (Hep3B), kidney cell line (HEK293) and lung cell line (A549) as described in <step 1> of Example 11. After 48 hours, the cells were harvested and luciferase expression efficiency was measured according to the same method as in <step 1> of Example 1. The results are shown in FIG. 7B.

Figure 7B:
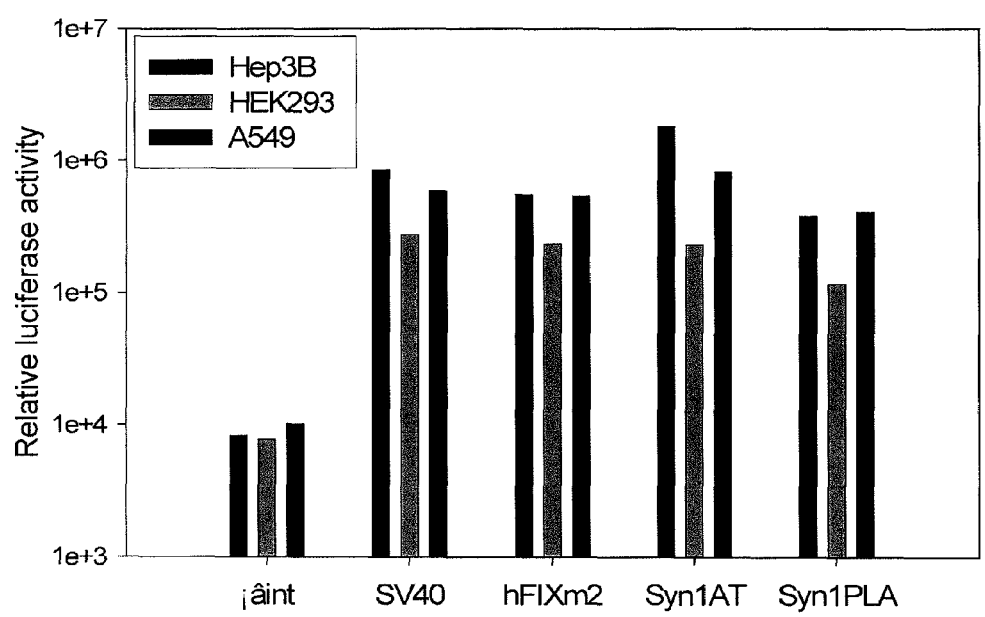
FIG. 7B: a histogram showing luciferase expression levels in Hep3B, HEK293 and A549 cells transfected with expression vectors carrying the expression cassettes containing various introns of FIG. 7A.

As shown in FIG. 7B, the luciferase expression induced by the intron-containing expression vectors was up to 200-fold higher than that induced by the intron-free expression vectors (in case of Syn1AT in Hep3B liver cell line). Particularly, the Syn1AT expression vector significantly contributed to the induction of luciferase activity as well as the induction of FIX expression as described in <step 3>.

<4-3> Analysis of mRNA Expression Stability

The luciferase expression vectors of <4-1> were transfected into A549 lung cell line according to the same method as in <4-2>, and the cells were harvested after 48 hours. Total RNA was extracted from the cells using a FastPure RNA kit (Takara). Single-stranded. DNAs were prepared using 500 ng of each total RNA as a template and AMV RTase (Takara). Then, PCR was performed using the above single-stranded DNAs as a template, and primer sets for detecting luciferase and β-actin. The results are shown in FIGS. 8A and 8B.

Figure 8A:
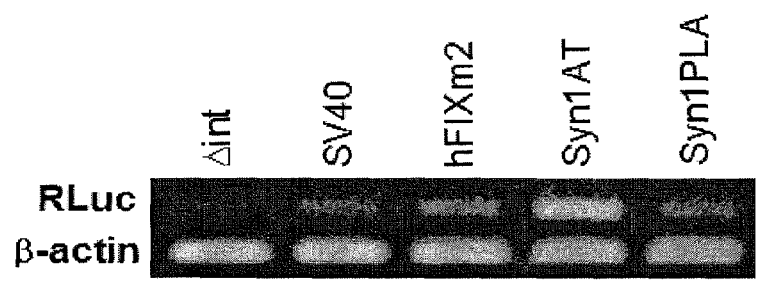
FIG. 8A: reverse-transcription PCR (RT-PCR) results showing mRNA expression levels of RLuc and β-actin in total RNA extracted from A549 cells transfected with the expression vectors of FIG. 7B.
Figure 8B:
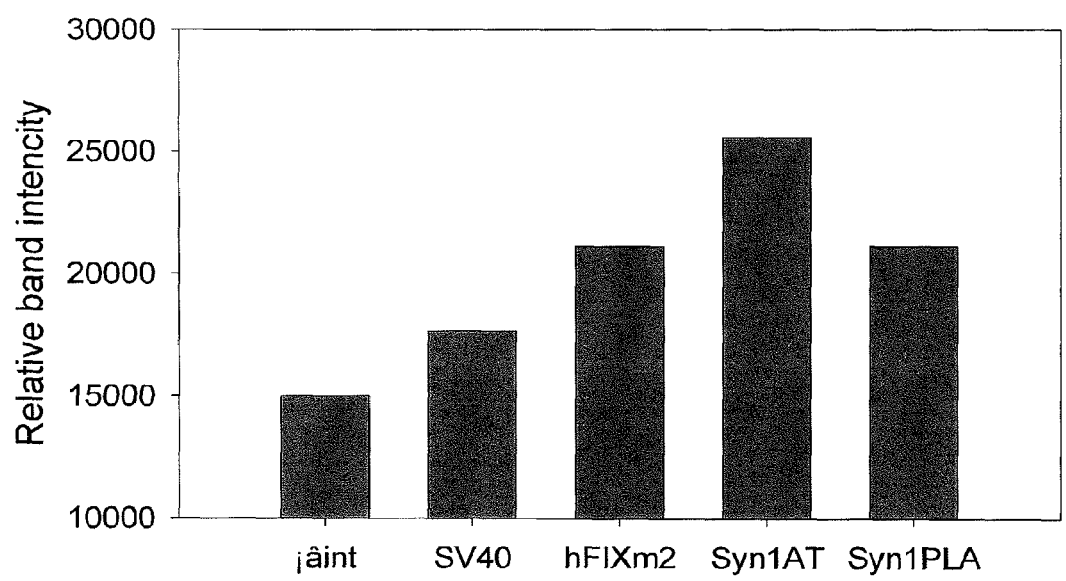
FIG. 8B: a histogram showing mRNA expression levels of RLuc normalized with β-actin for the mRNA band intensities of RLuc and β-actin obtained in FIG. 8A.

As shown in FIGS. 8A and 8B, the relative amount of RLuc mRNA induced by the pRL-Syn1AT vector was 1.7-fold higher than that of RLuc mRNA induced by the pRL-Δint vector. It shows that the inventive introns are responsible for higher stability of mRNA, which leads to enhanced gene expression.

<Step 5> Analysis of Effects of Antithrombin Introns on FIX Expression

In order to determine the effects of antithrombin introns on hFIX protein expression, the pBS-hFIXUTR-NA, pBS-hFIXUTR-ΔNAL and pBS-hFIXUTR-NAS plasmids prepared in <2-4> were inserted into pTRUF6 adeno-associated virus vectors according to the same method as in <step 3> to obtain expression vectors CMV-hFIXUTR-NA, CMV-hFIXUTR-ΔNAL and CMV-hFIXUTR-ΔNAS. Plasmid DNAs of the expression vectors CMV-hFIX, CMV-hFIXUTR, CMV-hFIXUTR-0.3kbFIXint (CMV-hFIXm2), CMV-hFIXUTR-Syn1AT, CMV-hFIXUTR-Syn2AT, CMV-hFIXUTR-ΔNA, CMV-hFIXUTR-ΔNAL and CMV-hFIXUTR-ΔNAS were injected into mouse tail veins according to the same method as in <step 3>, and blood hFIX concentrations in subjects were measured by ELISA. The results are shown in FIG. 9A.

Figure 9A:
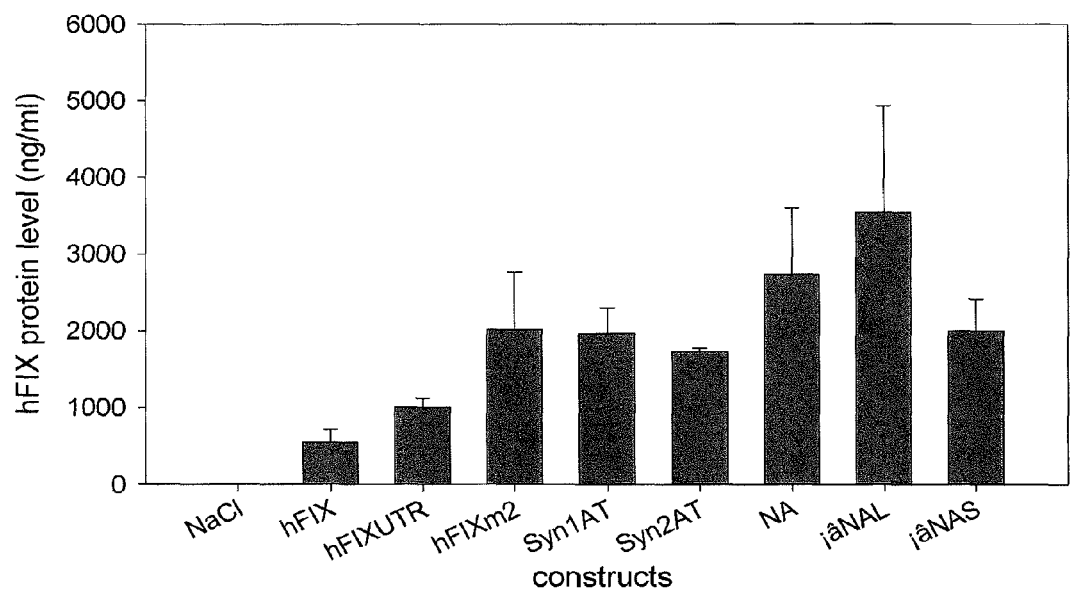
FIG. 9A: ELISA results showing the expression level of hFIX protein in the plasma samples obtained from mice injected through tail vein with the expression vectors carrying CMV-hFIXUTR-Syn1AT, CMV-hFIXUTR-Syn2AT, CMV-hFIXUTR-NA, CMV-hFIXUTR-ΔNAL, CMV-hFIXUTR-ΔNAS expression cassettes, and a CMV-hFIXUTR-0.3 kbFIXint (CMV-hFIXm2) expression cassette containing a 0.3 kb FIX intron as a control.

As shown in FIG. 9A, hFIX protein concentrations of expression vectors containing the synthetic or native antithrombin intron were 1.7 to 3.5-fold higher than that of CMV-hFIXUTR (1,730 to 3,540 ng/ml versus 1,000 ng/ml). Particularly, the CMV-hFIXUTR-ΔNAL expression vector showed about 1.7-fold higher expression efficiency than the previously established CMV-hFIXm2 expression vector (2,010 ng/ml versus 1,000 ng/ml). This result shows that the ΔNAL intron is very suitable for hFIX overexpression.

Meanwhile, in order to evaluate the effect of the intron ΔNAL on hFIX expression in vitro, the expression vectors CMV-hFIX, CMV-hFIXUTR and CMV-hFIXUTR-ΔNAL were transfected into HEK293T kidney cell line. At two days after the transfection, the cells together with media were collected and lysed. The hFIX protein level in the lysates was measured by electrophoresis using an hFIX antibody and the results are shown in FIG. 9B.

Figure 9B:
FIG. 9B: the results of Western blot analysis showing a hFIX protein expression level in HEK293T transfected with expression vectors carrying CMV-hFIX, CMV-hFIXUTR and CMV-hFIXUTR-ΔNAL expression cassettes.

As shown in FIG. 9B, the CMV-hFIXUTR-ΔNAL expression vector induced 1.55-fold higher hFIX expression level than the CMV-hFIX and CMV-hFIXUTR expression vectors. This result shows that the ΔNAL intron is efficient for hFIX overexpression.

EXAMPLE 3

Isolation of Liver-specific LCRs and Analysis of Gene Expression Efficiency by LCRs <Step 1> Isolation of Liver-specific LCRs and Construction of Plasmid Vectors Including LCRs The positions of the TGTTTGC motif was analyzed in the downstream of α1-antitrypsin, α-fetoprotein and albumin genes expressed only in the liver tissues. The results are shown in FIG. 10.

Figure 10:
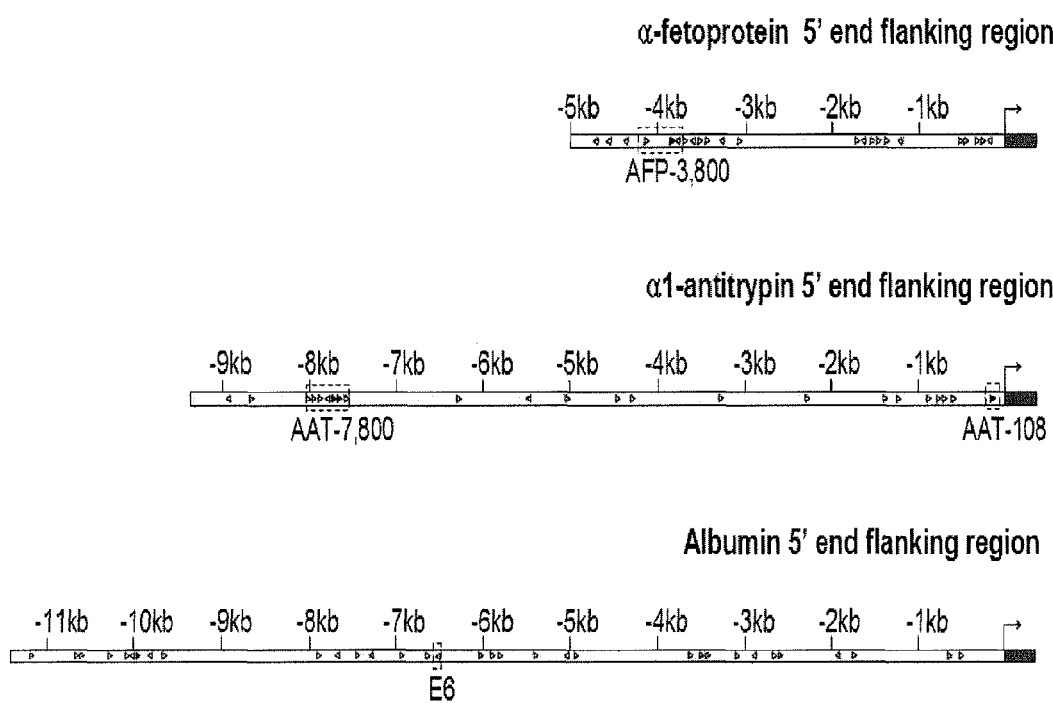
FIG. 10: a schematic diagram showing distribution of motifs identical or similar to the TGTTTGC motif found in LCR of Apo E gene, at 5'-end flanking regions of α-fetoprotein, AAT and albumin gene.

As shown in FIG. 10, seven TGTTTGC motifs are distributed at −7.8 kb site of α1-antitrypsin gene, six motifs being in a forward orientation and one motif being in a reverse orientation, and one motif is located in a forward orientation at −108 bp site of α1-antitrypsin gene. At −3.8 kb site of α-fetoprotein, two TGTTTGC motifs are distributed in a forward orientation and one motif is in a reverse orientation and at −6 kb site of albumin gene, one motif is located in a reverse orientation. In addition, TGTTTGC motifs are clustered at −800 bp site of the α1-antitrypsin gene, −1.5 kb and −500 bp sites of the α-fetoprotein gene, and −10 kb, −3.5 kb and −2.6 kb sites of the albumin gene. Among these sites, −7.8 kb and −108 bp sites of the α1-antitrypsin gene, −3.8 kb site of the α-fetoprotein gene and −6 kb site of the albumin gene were isolated.

In detail, in order to isolate LCR located at −108 bp site of the α1-antitrypsin gene, PCR was performed using the genomic DNA of <step 1> of Example 1 as a template, a primer set of SEQ ID NOS: 26 and 27, and DNA polymerase (Ex-Taq, Takara) according to the same method as in <step 1> of Example 1. The PCR products were purified by gel extraction, and inserted into pCR2.1-TOPO vectors. The desired α1-antitrypsin LCR having the nucleotide sequence of SEQ ID NO: 58 was identified by a restriction enzyme cleavage map and sequence analysis. The plasmid was designated "pCR-AAT108lcr."

Similarly, the above PCR procedure was repeated except for using primer sets of SEQ ID NOS: 28 and 29, SEQ ID NOS: 30 and 31, and SEQ ID NOS: 32 and 33 to amplify LCRs located at −7.8 kb site of the human α1-antitrypsin, −3.8 kb site of the human α-fetoprotein and −6 kb site of the human albumin gene, respectively. The PCR products were inserted into pCR2.1-TOPO vectors. The desired LCRs having the nucleotide sequences of SEQ ID NOS: 59, 60 and 61 were identified by a restriction enzyme cleavage map and sequence analysis. The plasmids were designated "pCR-AAT7800lcr," "pCR-AFP3800lcr" and "pCR-E6lcr," respectively.

Figure 11A:
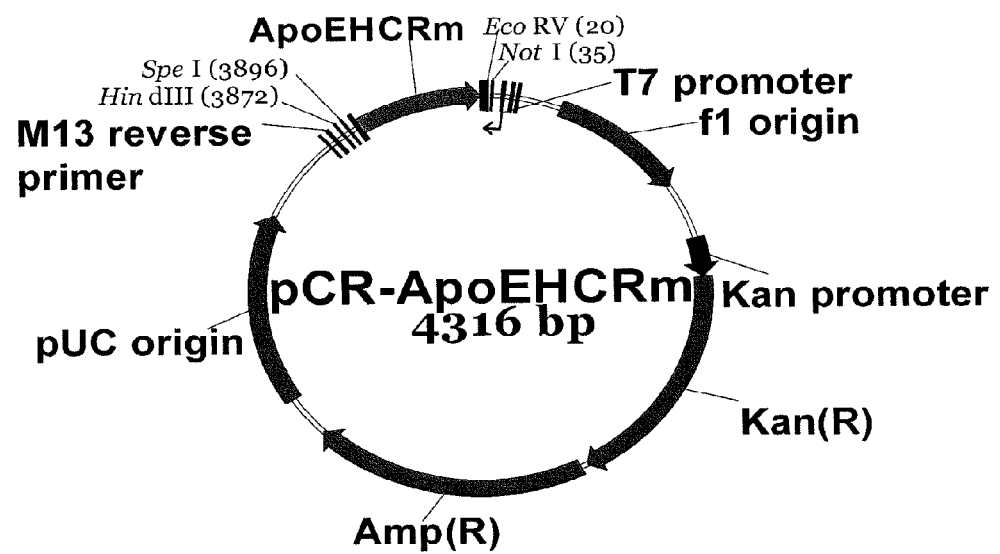
FIG. 11A: schematic diagrams of pCR-HCR and pCR-HCRm plasmids containing HCR (known as a hepatocyte control region of Apo E gene) and HCRm (known as a minimum structure HCR truncated with the TGTTTGC motif), respectively, and pCR-AAT7800lcr/pCR-AAT108lcr, pCR-AFP3800lcr and pCR-E6lcr plasmids containing the respective TGTTTGC motifs of α-fetoprotein, AAT and albumin.
Figure 11A:
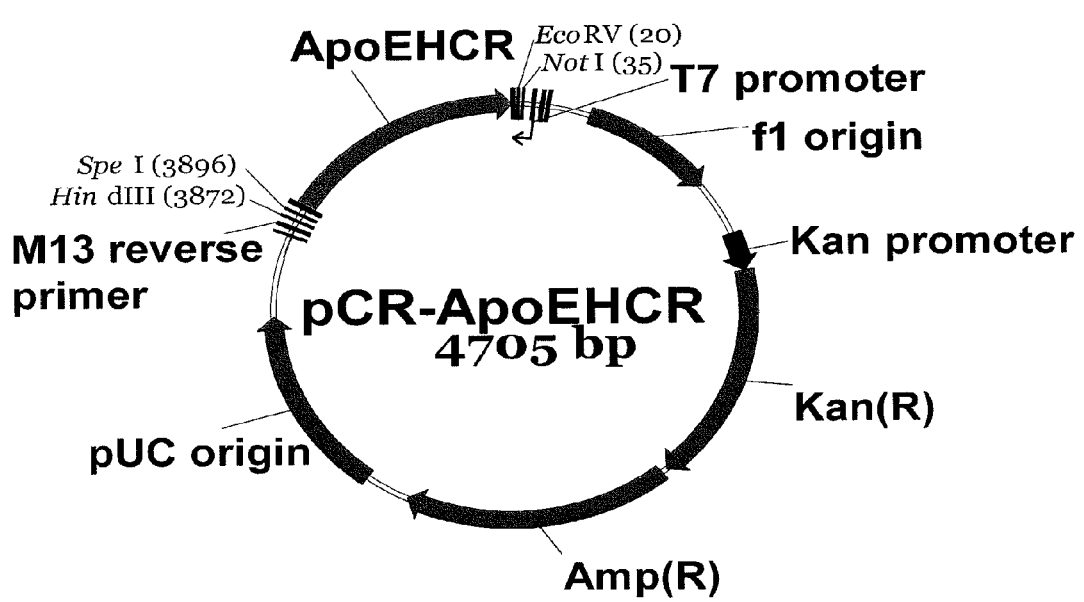
Figure 11A:
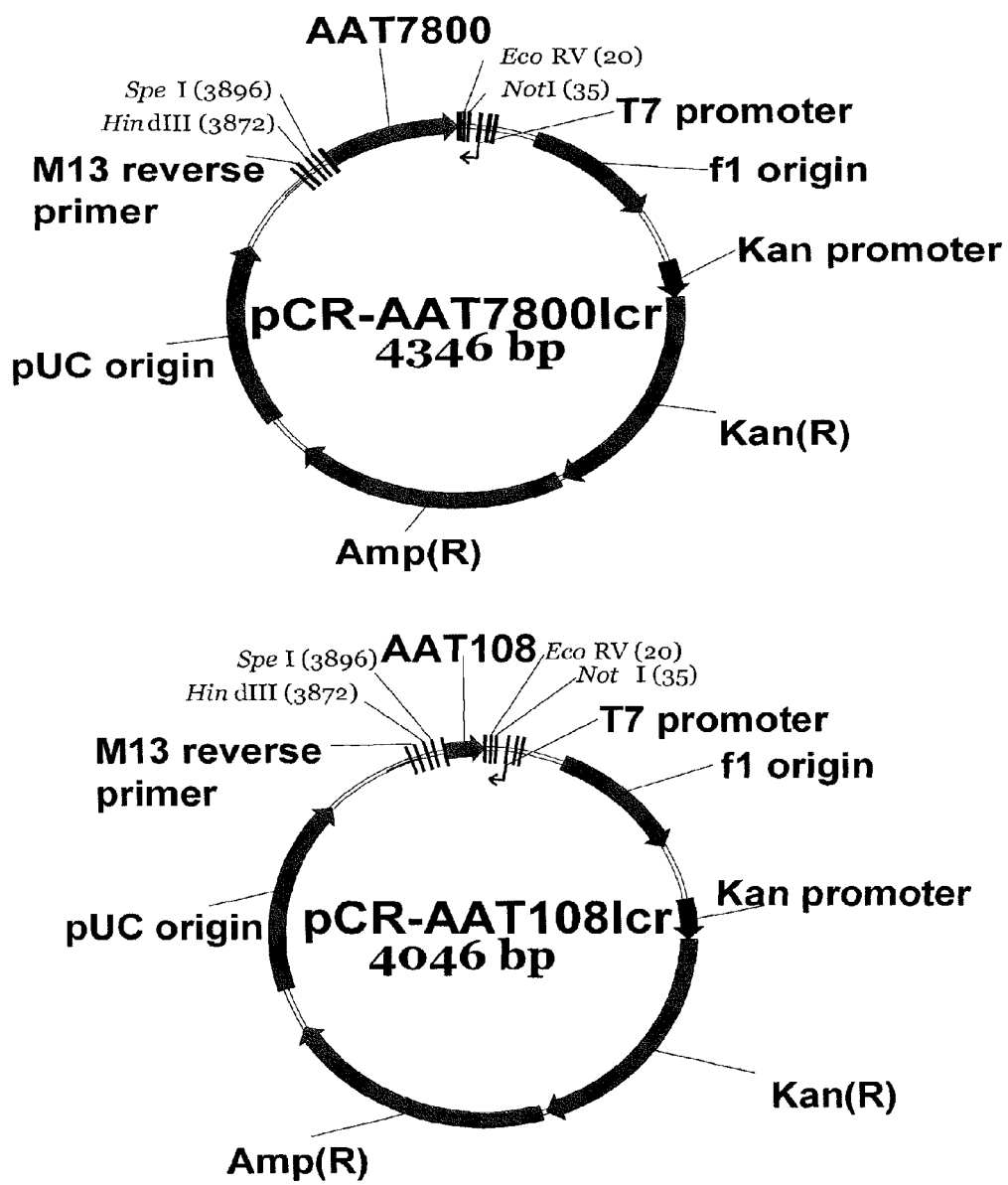
Figure 11A:
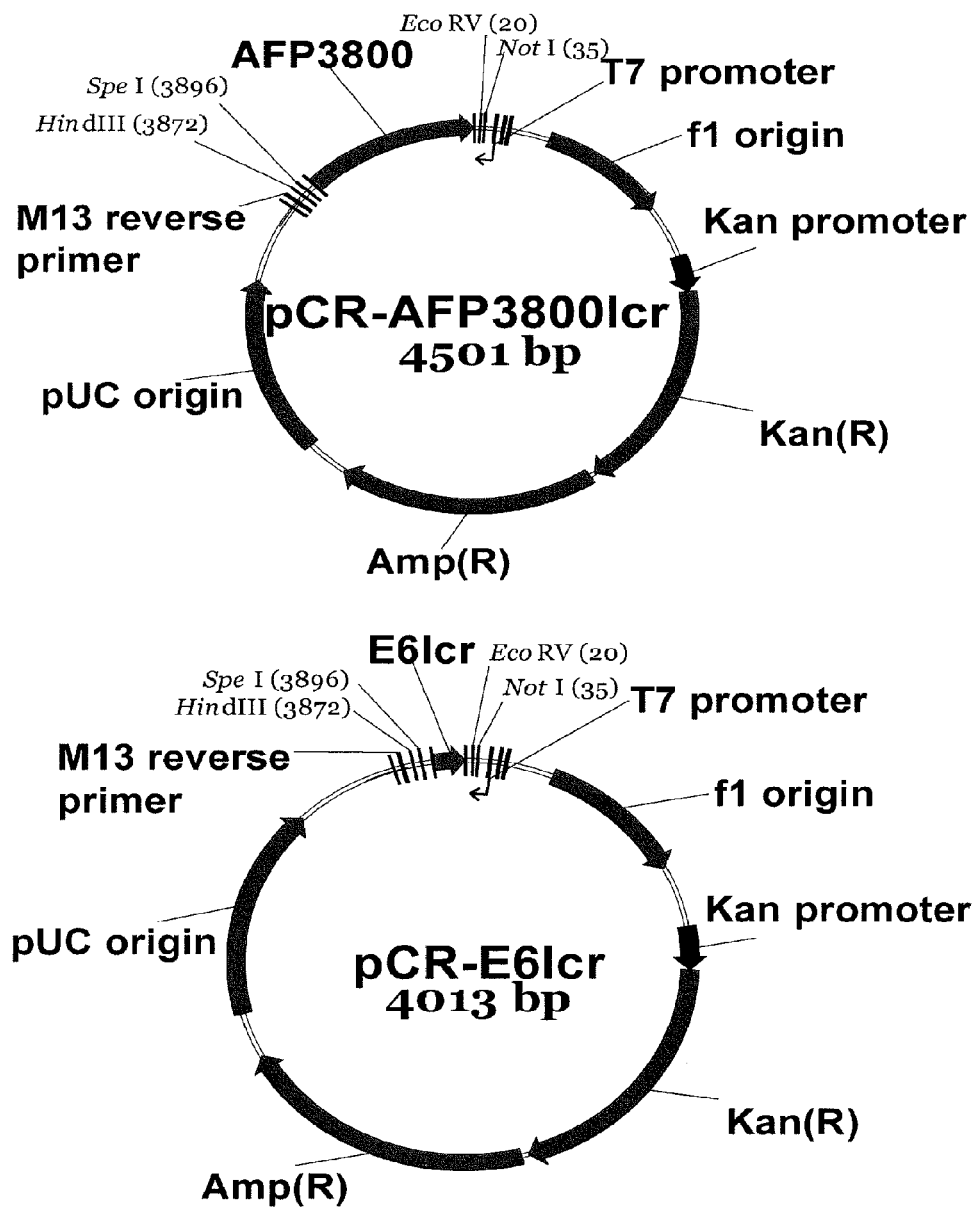
Figure 11B:
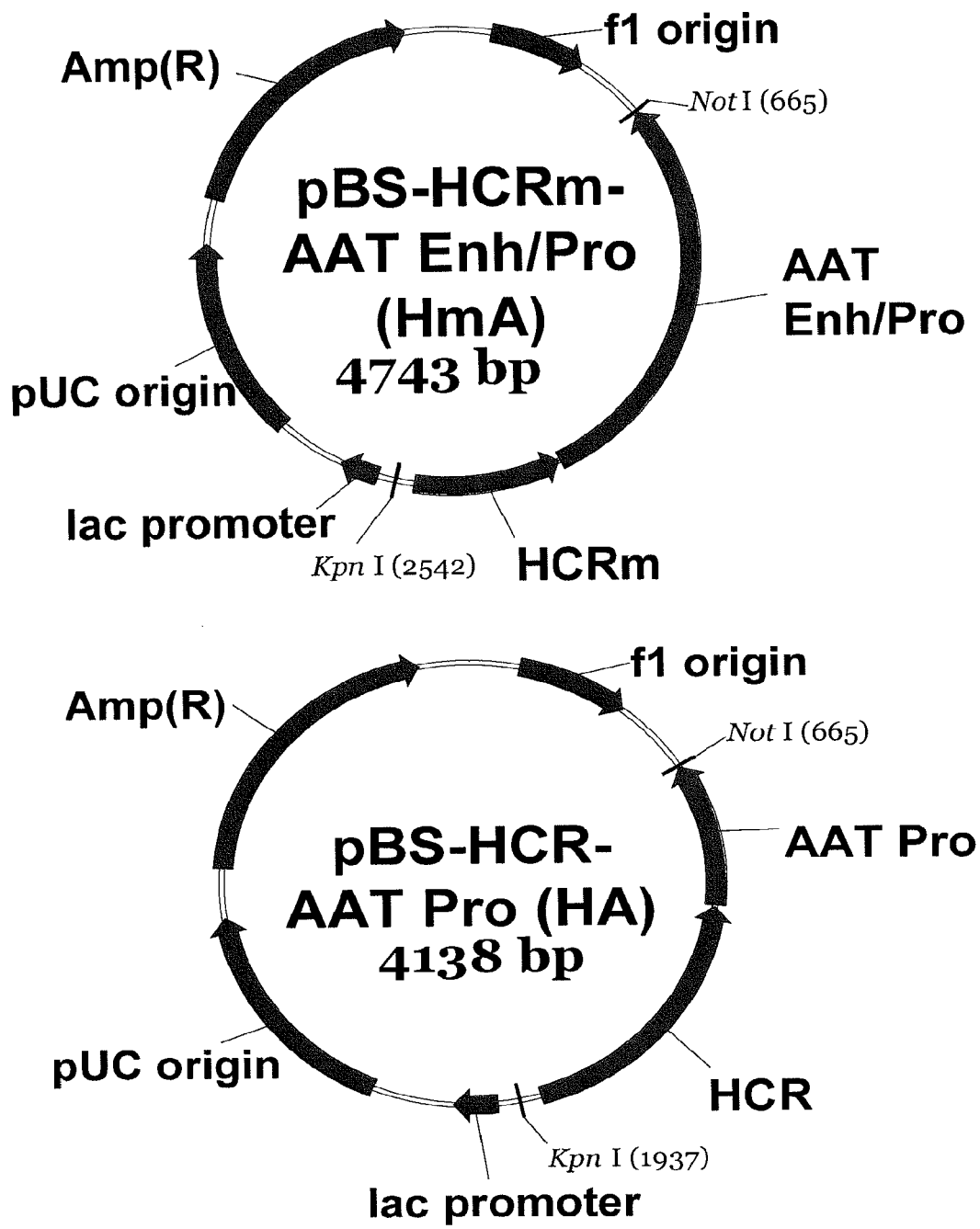
FIG. 11B: schematic diagrams of a pBS-HCRm-AATenh/pro (HmA) plasmid constructed by inserting HCRm, AAT enhancer and AAT promoter into a pBluescript II vector, and a pBS-HCR-AATpro (HA) plasmid constructed by inserting HCR and AAT promoter into a pBluescript II vector.

Meanwhile, in order to isolate the hepatocyte control region (HCR) and minimum structure HCR(HCRm) of human apolipoprotein E (ApoE) gene reported by Dang Q., PCR was performed using primer sets of SEQ ID NOS: 34 and 35 and SEQ ID NOS: 34 and 36, and the resulting PCR products were inserted into pCR2.1-TOPO vectors. The HCR and HCRm of the human ApoE gene were identified by a restriction enzyme cleavage map and sequence analysis. The plasmids were designated "pCR-ApoEHCR" and "pCR-ApoEHCRm," respectively. Schematic diagrams of these plasmids are shown in FIG. 11A. Further, a combination of HCRm with the enhancer and promoter of the AAT gene was inserted into a pBluescript II vector to construct pBS-HCRm-AATenh/pro (HmA), and a combination of HCR with the promoter of the AAT gene was inserted into a pBluescript II vector to construct pBS-HCR-AATpro (HA). Schematic diagrams of these plasmids are shown in FIG. 11B.

<Step 2> Analysis of Gene Expression Efficiency by LCRs

The effects of the combination of the LCRs isolated in <step 1> with a promoter, an enhancer and an intron on FIX expression efficiency were evaluated.

In detail, the pCR-AAT108lcr, pCR-AAT7800cr, pCR-AFP3800lcr, pCR-E6lcr, pCR-HCR and pCR-HCRm plasmids prepared in <step 1> were digested with HindIII/EcoRV, and inserted into HindIII/EcoRI (blunt-ended later) restriction sites of the pBS-PF prepared in <step 2> of Example 1 to obtain pBS-AAT108-PF, pBS-AAT7800-PF, pBS-AFP3800-PF, pBS-E6-PF, pBS-HCR-PF and pBS-HCRm-PF, respectively. These plasmids were digested again with KpnI and NotI, and inserted into KpnI/NotI restriction sites of the pBS-CMV-hFIXUTR-Syn1PLA prepared in <step 5> of Example 2 to obtain pBS-AAT108-PF-hFIXUTR-Syn1PLA, pBS-AAT7800-PF-hFIXUTR-Syn1PLA, pBS-AFP3800-PF-hFIXUTR-Syn1PLA, pBS-E6-PF-hFIXUTR-Syn1PLA, pBS-HCR-PF-hFIXUTR-Syn1PLA and pBS-HCRm-PF-hFIXUTR-Syn1PLA. Schematic diagrams of these plasmids are shown in FIG. 12A.

The plasmids were digested with KpnI and SalI, and inserted into KpnI/SalI restriction sites of pTRUF6 adeno-associated virus vectors to obtain expression vectors AAT108-PF-hFIXUTR-Syn1PLA, AAT7800-PF-hFIXUTR-Syn1PLA, AFP3800-PF-hFIXUTR-Syn1PLA, E6-PF-hFIXUTR-Syn1PLA, HCR-PF-hFIXUTR-Syn1PLA and HCRm-PF-hFIXUTR-Syn1PLA. The plasmid DNAs of the expression vectors were injected into mouse tail veins according to the same method as in <step 3> of Example 2, and the hFIX protein expression level was measured by ELISA. The results are shown in FIG. 12B.

Figure 12B:
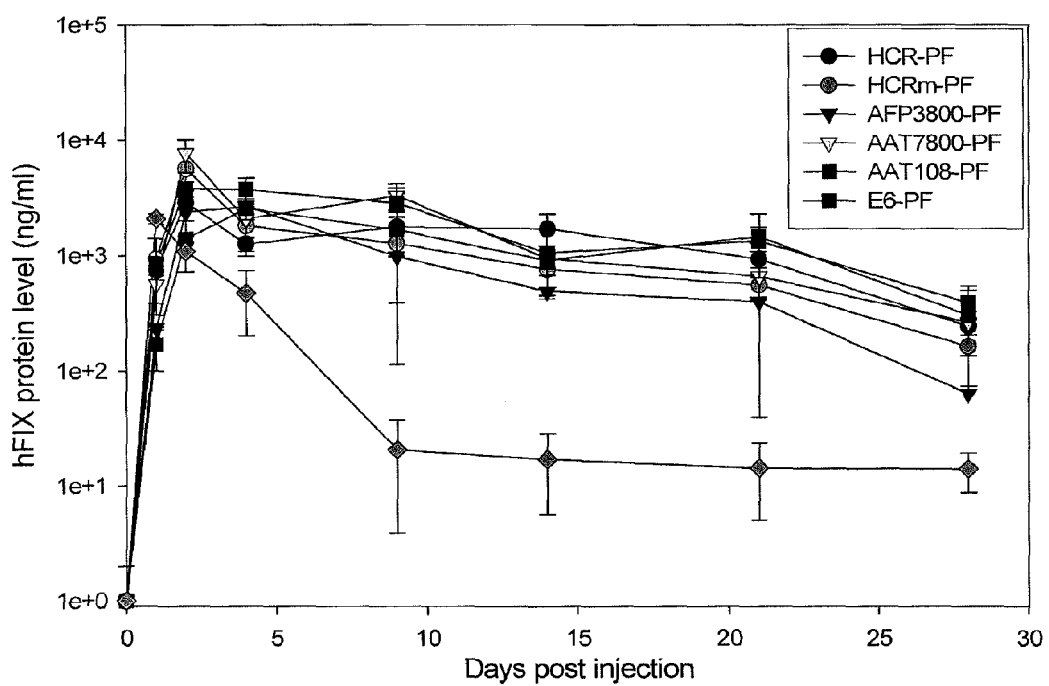
FIG. 12B: ELISA results showing the expression level of hFIX protein in the plasma samples obtained from the mice injected through tail vein with expression vectors carrying the expression cassettes of FIG. 12A and a CMV-hFIXUTR-Syn1PLA expression vector.

As shown in FIG. 12B, at two days after the injection, the LCR-containing expression vectors showed up to 7-fold higher hFIX expression level than CMV-hFIXUTR-Syn1PLA (AAT7800-PF-hFIXUTR-Syn1PLA 7,640 ng/ml versus CMV-hFIXUTR-Syn1PLA 1,090 ng/ml). Particularly, the AAT108-PF-hFIXUTR-Syn1PLA continuously expressed hFIX of 390 ng/ml or more until 4 weeks after the injection, and such a expression level was up to 1.6-fold higher than that (250 ng/ml) of the HCR-PF-FIX-Syn1PLA. This result shows that the AAT108 intron is very suitable for sustained expression of hFIX.

EXAMPLE 4

Evaluation of Therapeutic Efficacy of the Inventive Expression Vector for Hemophilia B An expression vector AAT108-PAF-hFIXUTR-Syn1PLA was constructed using pBS-PAF prepared in <step 2> of Example 1 according to the same method as in <step 2> of Example 3. Further, the pBS-CMV-hFIXUTR-ΔNAL constructed in <2-4> of Example 2 was digested with NotI and SalI, and inserted into NotI/SalI restriction sites of the AAT108-PF-hFIXUTR-Syn1PLA and AAT108-PAF-hFIXUTR-Syn1PLA constructed in <step 2> of Example 3 to obtain expression vectors AAT108-PF-hFIXUTR-ΔNAL and AAT108-PAF-hFIXUTR-ΔNAL.

Meanwhile, the pCR-AAT enh/pro of <step 1> of Example 1 was digested with SpeI (blunt-ended later)/NotI, and inserted into the EcoRV/NotI restriction sites of the pCR-HCRm of <step 2> of Example 3 to obtain a pCR-HCRm-AATenh/pro expression vector (HmA). The pCR-HCRm-AATenh/pro (HmA) expression vector was digested with KpnI and NotI, and inserted into KpnI and NotI restriction sites of CMV-hFIXUTR-ΔNAL constructed in <Step 5> of Example 2 to obtain a HmA-hFIXUTR-NAL expression vector.

The pCR-AAT enh/pro described in <step 1> of Example 1 was digested with BglII (blunt-ended later)/NotI, and inserted into the EcoRV/NotI restriction sites of pCR-HCR described in <step 2> of Example 3 to obtain a pBS-HCR-AATpro (HA) expression vector. The pBS-HCR-AATpro (HA) expression vector was digested with KpnI/NotI, and inserted into KpnI/NotI restriction sites of CMV-hFIXUTR-1.4kbFIXint described in <step 3> of Example 2 to obtain a HA-hFIXUTR-1.4kbFIXint expression vector.

Figure 13A:
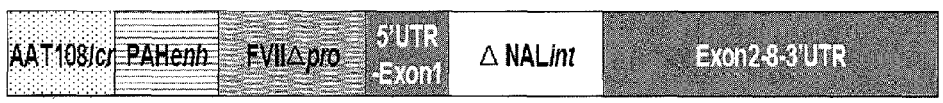
FIG. 13A: schematic diagrams showing expression cassettes containing a combination of PAH enhancer and FVIIΔ promoter (PF) or a combination of PAH enhancer, AMBP enhancer and FVIIΔ promoter (PAF), NAL intron, and AAT108 LCR; a HmA (HCRm-AAT enh/pro)-hFIXUTR-ΔNAL expression cassette; and a HA (HCR-AATpro)-hFIX-UTR-1.4kbFIXint expression cassette.
Figure 13A:
Figure 13A:
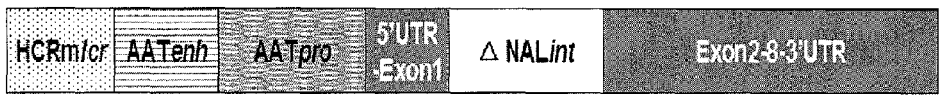
Figure 13A:
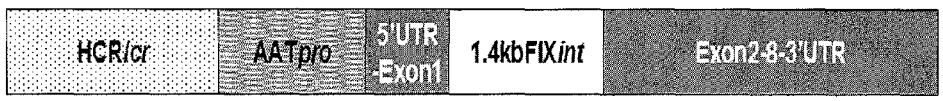

Schematic diagrams of the expression vectors are shown in FIG. 13A.

25 μg of each plasmid DNA of the AAT108-PF-hFIXUTR-ΔNAL, AAT108-PAF-hFIXUTR-ΔNAL, HmA-hFIXUTR-ΔNAL, and CMV-hFIXUTR-ΔNAL (prepared in <step 5> of Example 2) expression vectors was injected into a tail vein of hemophilia B mouse, and the hFIX protein concentration and the blood clotting activity were measured by ELISA.

Figure 13B:
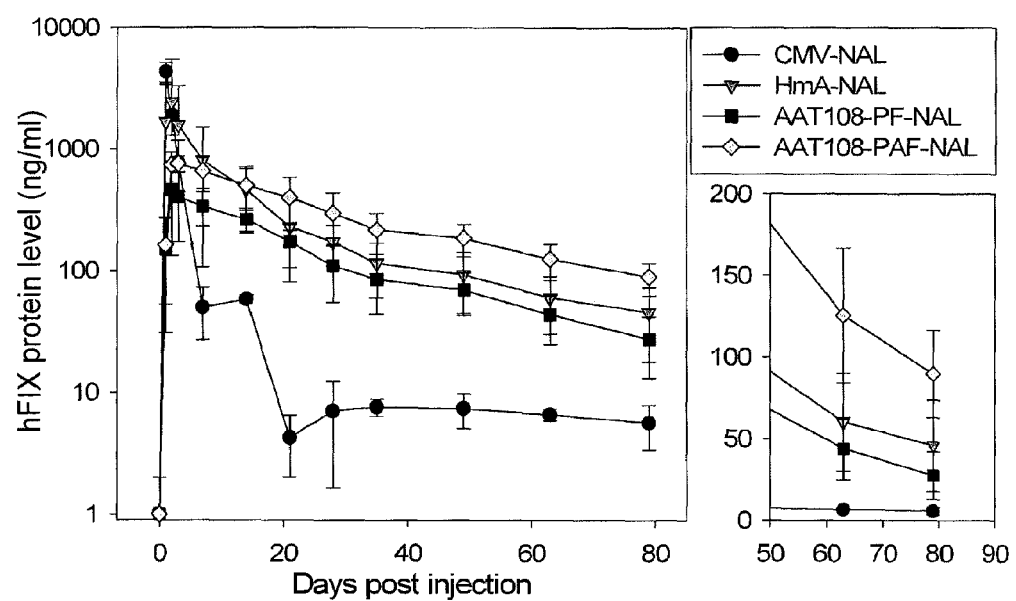
FIG. 13B: ELISA results showing the expression level of hFIX protein in the plasma samples obtained from the mice injected through tail vein with expression vectors carrying the expression cassettes of FIG. 13A, and a CMV-hFIXUTR-ΔNAL expression vector.

As shown in FIG. 13B, the hFIX expression level induced by the AAT108-PAF-hFIXUTR-ΔNAL expression vector was 9.8% at day 1 after the injection, 30.6% at day 2, 82% at day 7, 108% at week 2 and 208% at week 9, relative to that induced by the HmA-hFIXUTR-ΔNAL expression vector. Further, the hFIX expression level induced by the AAT108-PF-hFIXUTR-ΔNAL expression vector was 9.0% at day 1 after the injection, 19.2% at day 2, 41.9% at day 7, 56.9% at week 2 and 73.0% at week 9, relative to that induced by the HmA-hFIXUTR-ΔNAL expression vector.

Figure 13C:
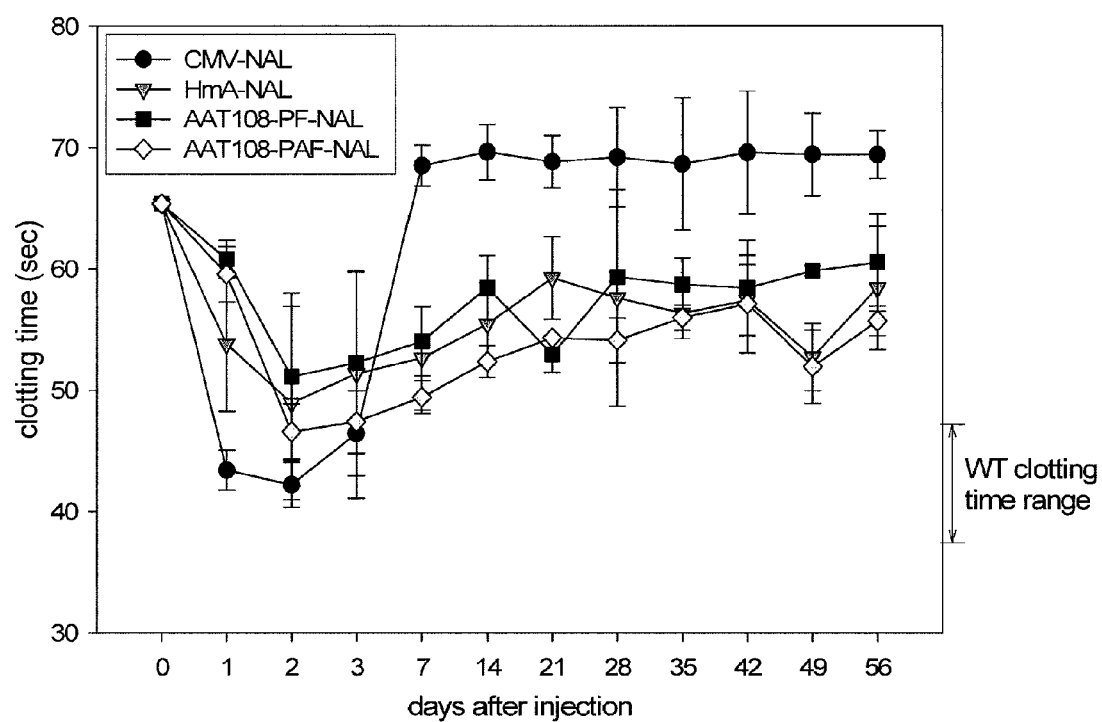
FIGS. 13C and 13D: the clotting time and activity measured by an activated partial thromboplastin time (APTT) method using the plasma samples obtained in FIG. 13B.

The blood clotting activities of normal mouse and hemophilia B mice injected with hFIX expression vectors were measured by an activated partial thromboplastin time (APTT) method as follows. FIX-deficient plasma, 10-fold diluted mouse-derived plasma and activated actin (each 50 μl) were mixed and incubated at 37° C. for three minutes. $CaCl_2$ was added thereto, and the time taken for sample clotting was measured with a blood clotting detector KC10A (Amelung). The blood clotting time of the normal mouse was about 44 seconds, and that of the hemophilia B mouse was about 65 seconds. As shown in FIG. 13C, the hemophilia B mice administrated with the hFIX expression vectors showed about 80% of the normal blood clotting time until 3 days after the injection. After 7 days, the blood clotting time of the CMV-hFIXUTR-ΔNAL-administrated mice was returned to the level before the injection, but the mice administrated with the AAT108-PF-hFIXUTR-ΔNAL and AAT108-PAF-hFIXUTR-ΔNAL exhibited an improved blood clotting time of 50 to 60 seconds.

Figure 13D:
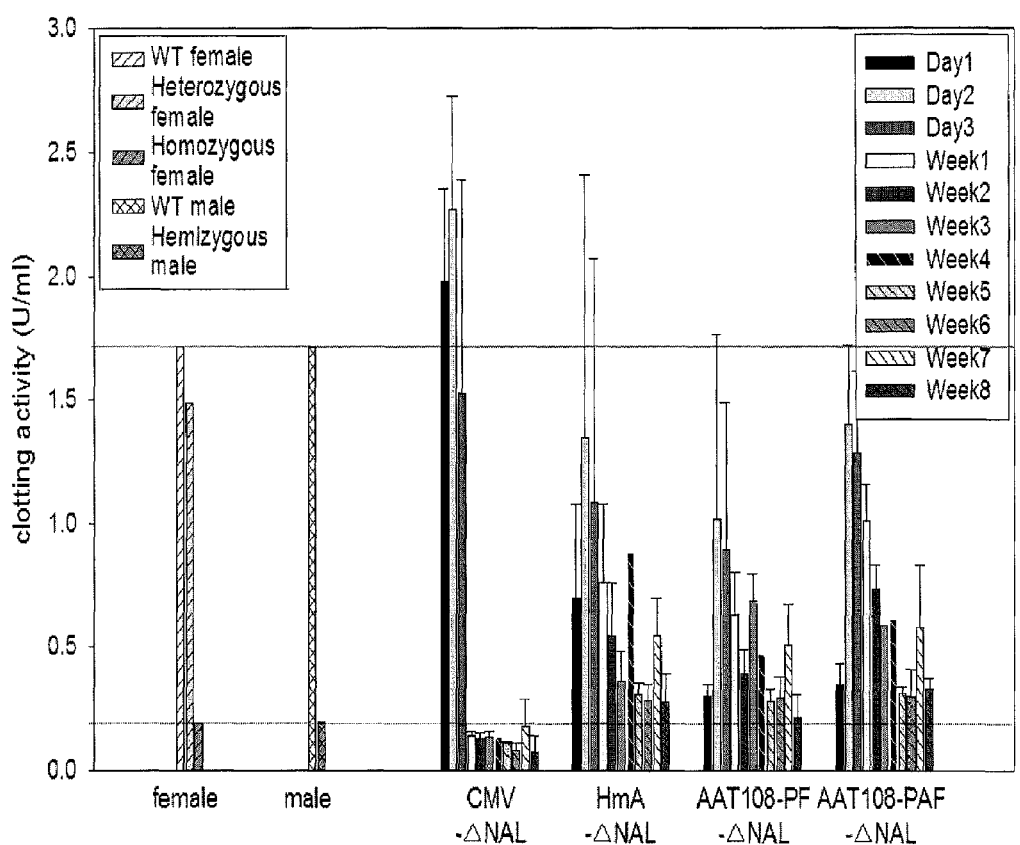

Further, the clotting activity of the samples was calculated according to a standard curve of standard activity versus standard clotting time. As shown in FIG. 13D, the blood clotting activities of the hemophilia B mice treated with the AAT108-PF-hFIXUTR-ΔNAL and AAT108-PAF-hFIXUTR-ΔNAL expression vectors were respectively 34.1% and 29.3% at week 8 after the injection, relative to that of normal mice. Particularly, the blood clotting activity of the mice treated with the AAT108-PAF-hFIXUTR-ΔNAL expression vector was 31.9% at week 8 after injection, relative to that of the normal mice.

Meanwhile, $2 \times 10^9$ IP of recombinant adeno-associated viruses using the HA-hFIXUTR-1.4kbFIXint, AAT108-PF-hFIXUTR-ΔNAL, AAT108-PAF-hFIXUTR-ΔNAL, and CMV-hFIXUTR-1.4kbFIXint expression vectors according to the same method as in <step 3> of Example 2 were injected into portal veins of hemophilia B mice, and the hFIX protein concentration and the blood clotting activity were measured by ELISA and APTT method as described above. The results are shown in FIGS. 14A and 14B.

Figure 14A:
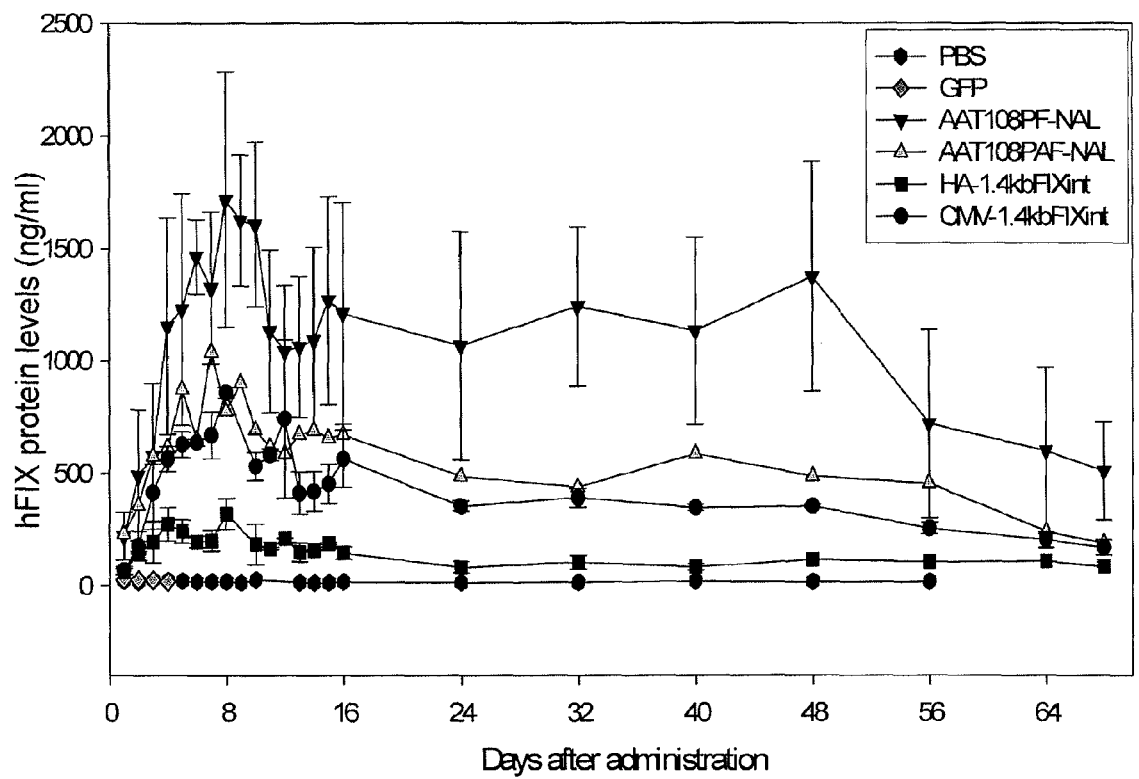
FIGS. 14A and 14B: the results showing the expression level of hFIX protein by ELISA and the clotting activity measured by APTT method, respectively, for plasma samples obtained from hemophilia B mice administered through portal vein with $2 \times 10^9$ IP of recombinant adeno-associated viruses carrying AAT108-PF-hFIXUTR-ΔNAL and AAT108-PAF-hFIXUTR-ΔNAL expression cassettes, and common HA-hFIXUTR-1.4kbFIXint and CMV-hFIXUTR-1.4kbFIXint expression cassettes as a control.

As shown in FIG. 14A, the AAT108-PF-hFIXUTR-ΔNAL-carrying viruses induced hFIX protein of up to 2,379 ng/ml, and the AAT108-PAF-hFIXUTR-ΔNAL-carrying viruses induced hFIX protein of up to 1,431 ng/ml. On the other hand, the hFIX expression levels induced by the control viruses, i.e., the CMV-hFIXUTR-1.4kbFIXint-carrying viruses and the HA-hFIXUTR-1.4kbFIXint-carrying viruses were up to 1,542 ng/ml and 380 ng/ml, respectively. Particularly, the AAT108-PF-hFIXUTR-ΔNAL-containing viruses induced hFIX expression of 500 ng/ml or more until 68 weeks after the injection. This result shows that LCR-containing expression vectors according to the present invention are suitable for gene therapy requiring long-term gene expression.

Figure 14B:
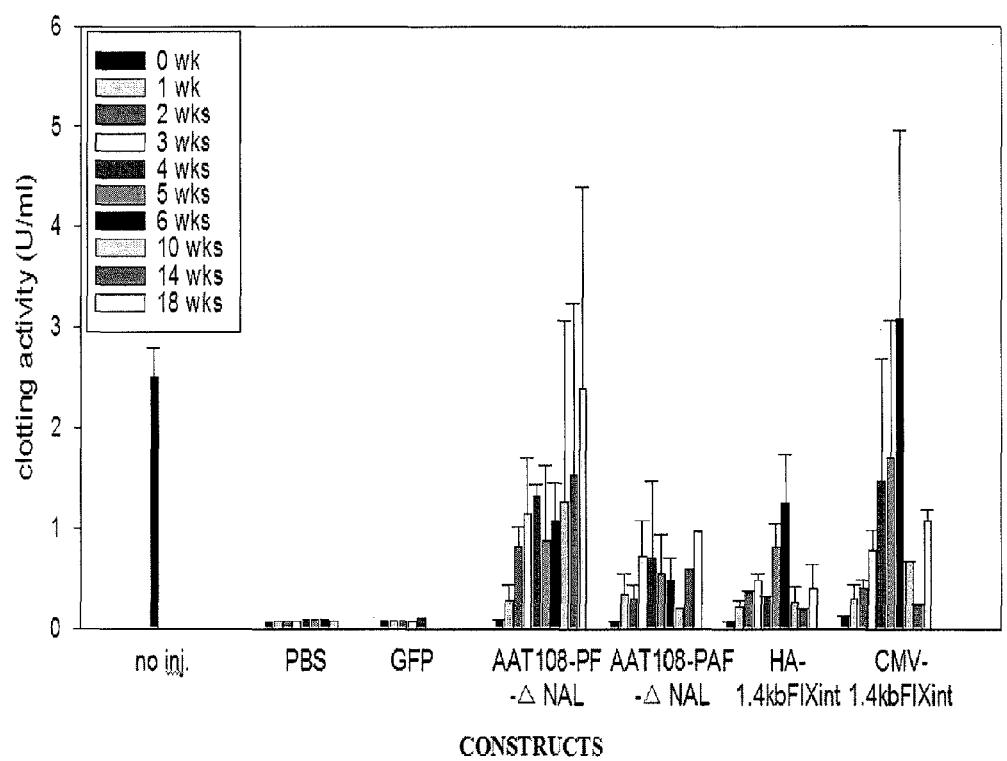

As shown in FIG. 14B, the mice administrated with rAAV carrying AAT108-PF-hFIXUTR-ΔNAL exhibited 59.1% or more of clotting activity of normal mice until 7 weeks after the injection.

The above results show that the inventive gene expression systems are effective for stable and sustained expression required for the treatment of hemophilia.

EXAMPLE 5

Figure 15A:
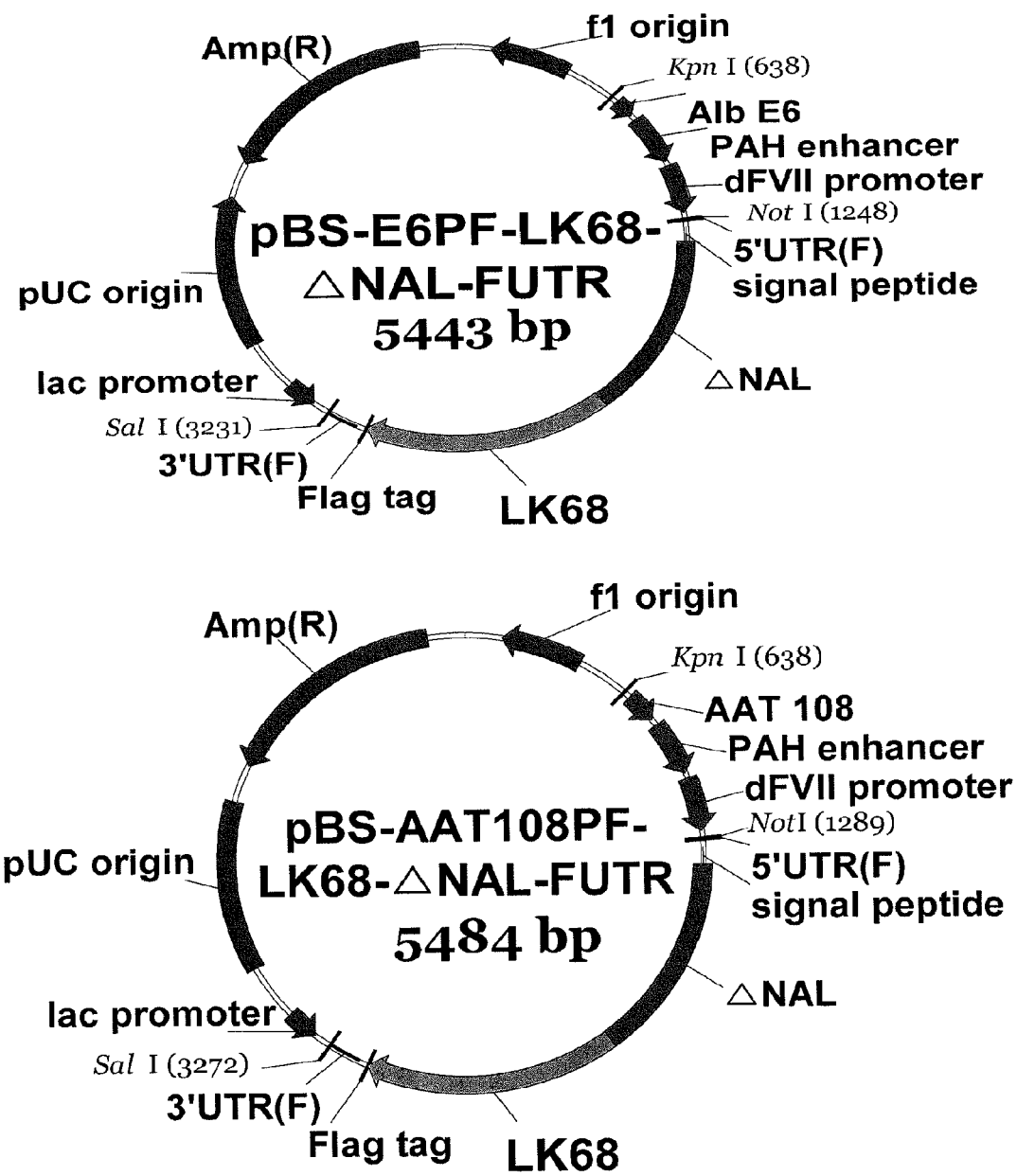
FIG. 15A: schematic diagrams of expression vectors constructed by introducing various LCRs (HCR, HCRm, AFP3800, AAT7800, AAT108 and E6) into PF-LK68-ΔNAL-UTR expression cassettes.
Figure 15A:
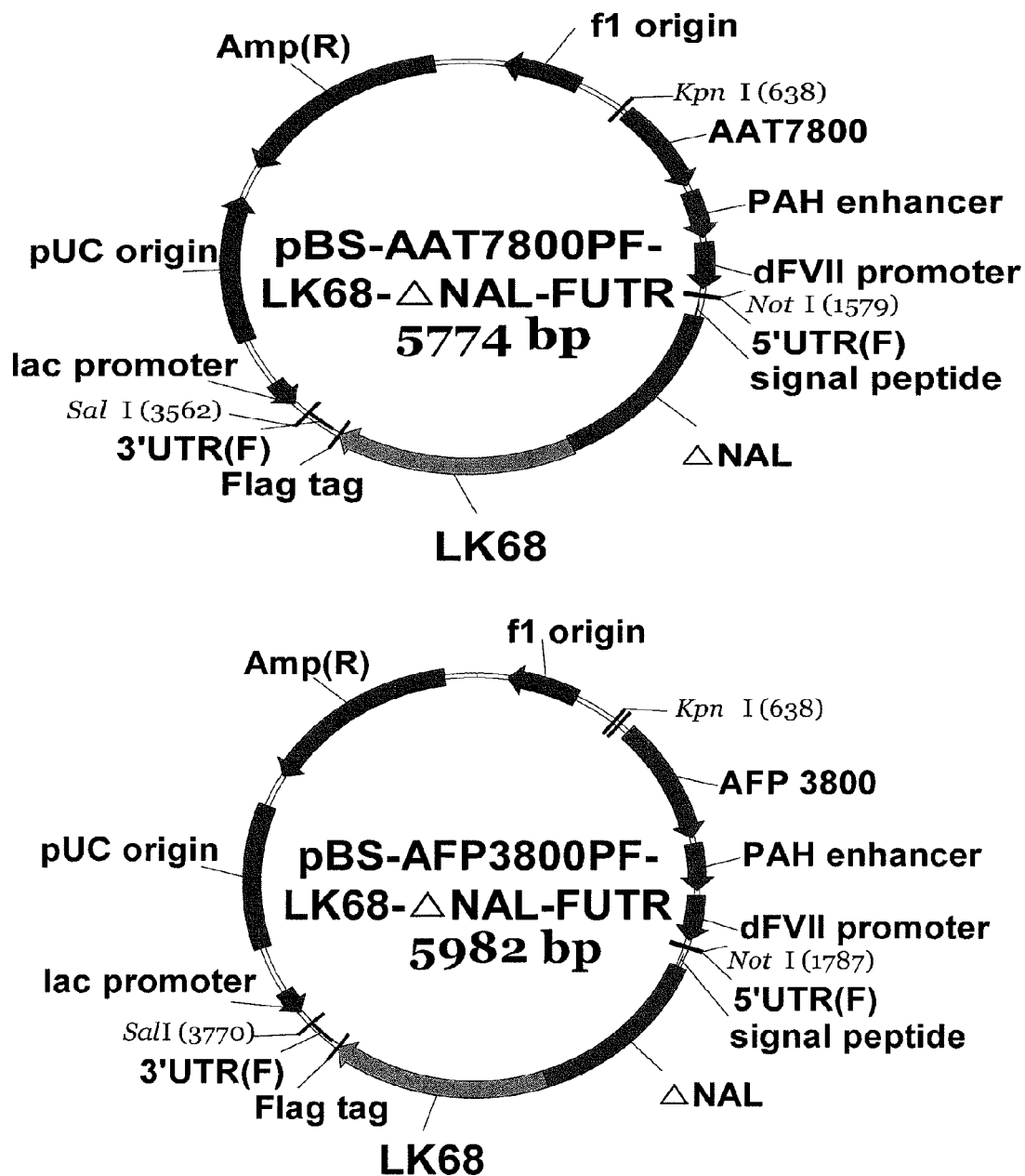
Figure 15A:
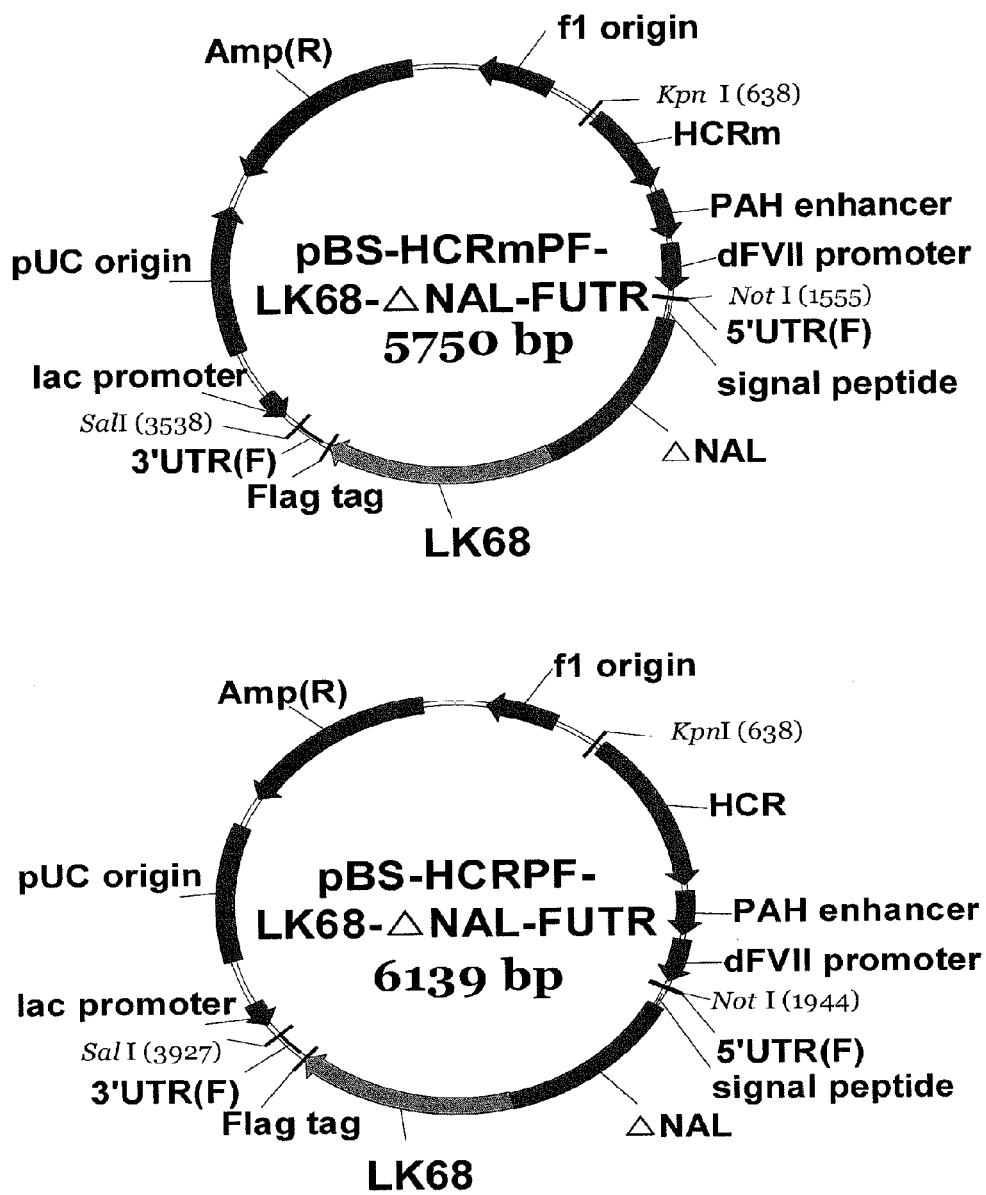

Construction of Liver-specific Expression Vectors Including Kringle Domain KIV9-KIV10-KV(LK68) Gene of Anti-angiogenesis Protein Apo (a) and Evaluation of LK68 Protein Expression Efficiency In order to introduce ΔNAL intron and FIX UTR into a LK68 expression vector, first, PCR was performed using pAAV-LK68 (Patent No. KR10-0681762) as a template, primer sets of SEQ ID NOS: 37 and 38 and SEQ ID NOS: 39 and 40, and Ex-Taq to obtain a FIX 5'UTR-signal sequence fragment and an LK68-FIX 3'UTR fragment. The PCR condition was as follows: initial denaturation at 94° C. for five minutes; 30 cycles of denaturation at 94° C. for one minute, annealing at 60° C. for one minute and extension at 72° C. for one minute; and final extension at 72° C. for three minutes. The 5'UTR-signal sequence fragment and the LK68-3'UTR fragment were respectively inserted into NotI/XhoI and AatII/SalI restriction sites of the pBS-hFIXUTR-ΔNAL vector prepared in <2-4> of Example 2. The desired DNA fragments were identified by a restriction enzyme cleavage map and sequence analysis, and the plasmid was designated "pBS-LK68-ΔNAL-FUTR." The LK68-ΔNAL-FUTR fragment obtained by treating the pBS-LK68-ΔNAL-FUTR plasmid with restriction enzymes NotI and SalI was inserted into NotI/SalI restriction sites of the AAT108-PF-hFIXUTR-NAL prepared in Example 4 to obtain an expression vector AAT108-PF-LK68-ΔNAL-FUTR. The above procedure was repeated in the presence of different LCRs or in the absence of LCR to obtain expression vectors E6-PF-LK68-ΔNAL-FUTR, AAT7800-PF-LK68-ΔNAL-FUTR, AFP3800-PF-LK68-ΔNAL-FUTR, HCRm-PF-LK68-ΔNAL-FUTR, HCR-PF-LK68-ΔNAL-FUTR and PF-LK68-ΔNAL-FUTR. The cleavage maps of the expression vectors are shown in FIG. 15A.

The expression vectors were inserted into mouse tail veins according to the same method as in <step 3> of Example 2. Blood samples were collected from the mice, and the expression level of LK68 protein was measured by ELISA.

Figure 16A:
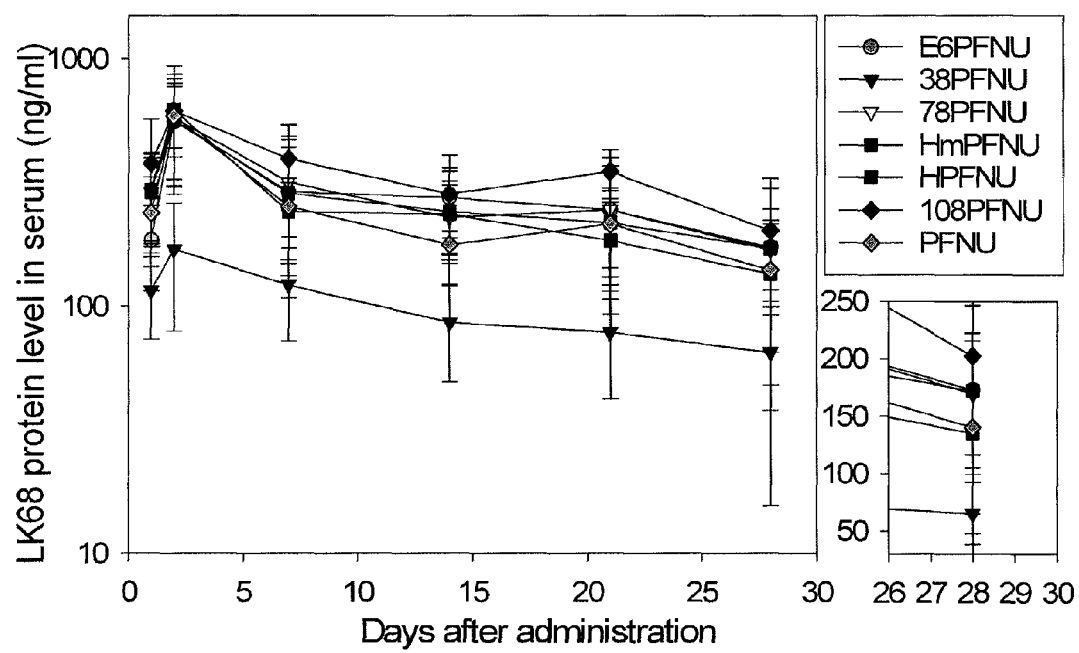
FIG. 16A: ELISA results showing the expression level of LK68 protein in the plasma samples obtained from the mice injected through tail vein with expression vectors carrying PF-LK68-ΔNAL-UTR expression cassettes introduced various LCRs (HCR, HCRm, AFP3800, AAT7800, AAT108 and E6)

As shown in FIG. 16A, among LCRs, AAT108 showed the highest gene expression efficiency. Particularly, the LK68 expression efficiency of the AAT108-PF-LK68-ΔNAL-FUTR expression vector was 158.4% at day 1 after the injection, 104.8% at day 2, 155.8% at day 7, 160.2% at week 2, 162.7% at week 3 and 144.1% at week 4, relative to that of the PF-LK68-ΔNAL-FUTR expression vector.

Figure 15B:
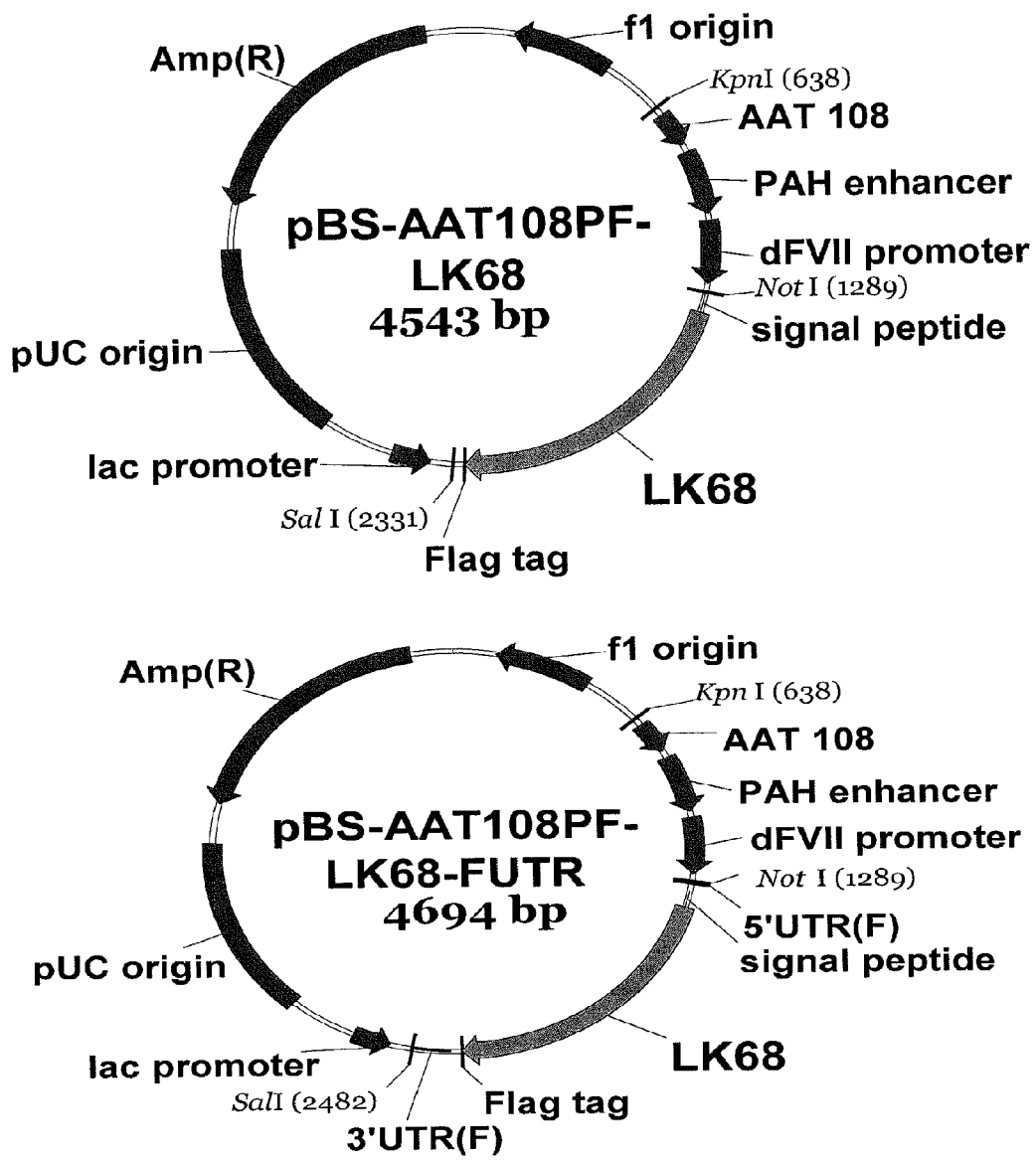
FIG. 15B: schematic diagrams of an AAT108-PF/PAF-LK68 expression vector, an AAT108-PF/PAF-LK68-UTR expression vector, and an AAT108-PF/PAF-LK68-ΔNAL-UTR expression vector.
Figure 15B:
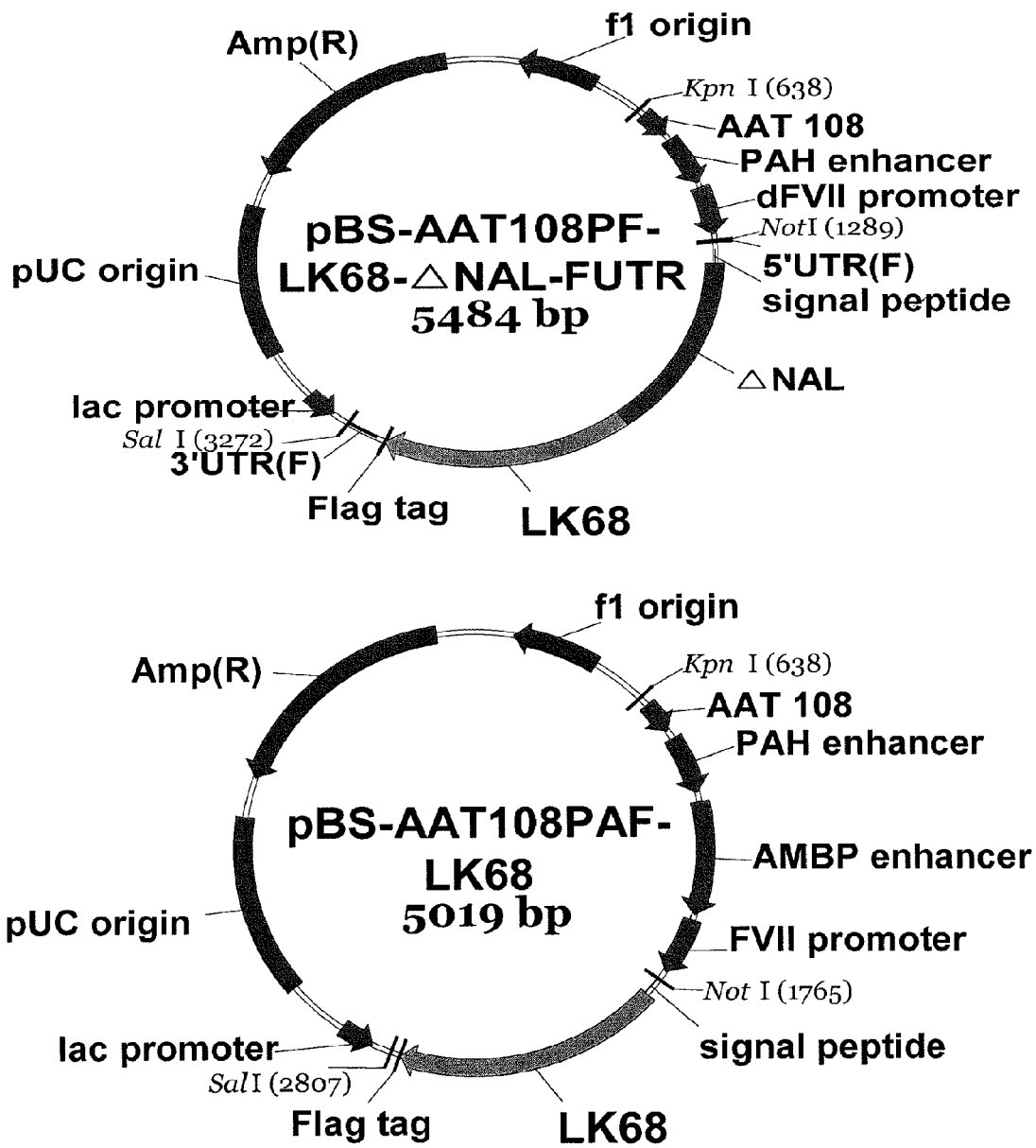
Figure 15B:
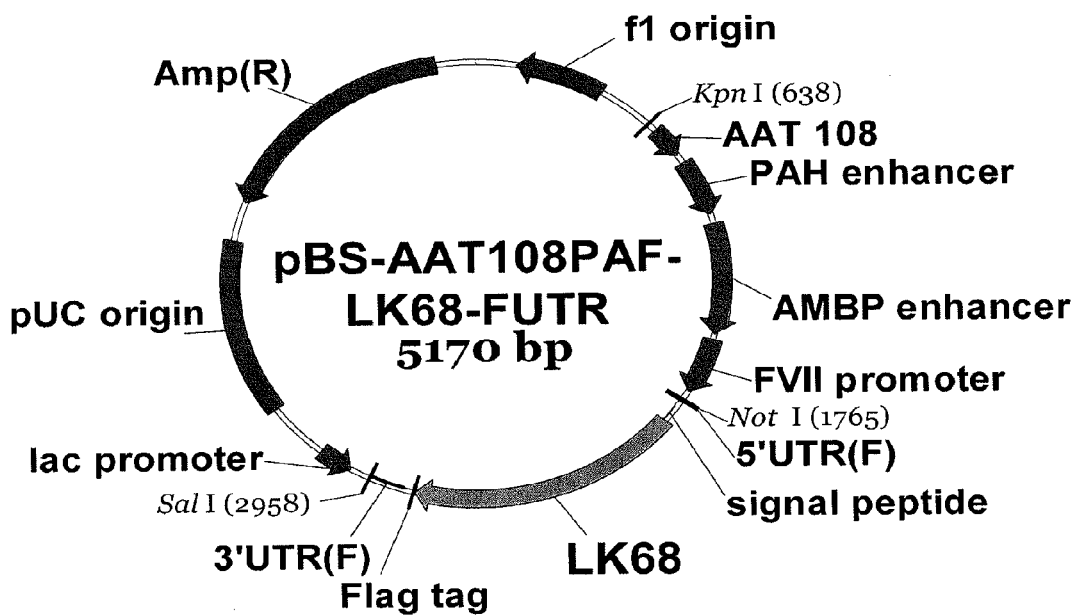
Figure 15B:
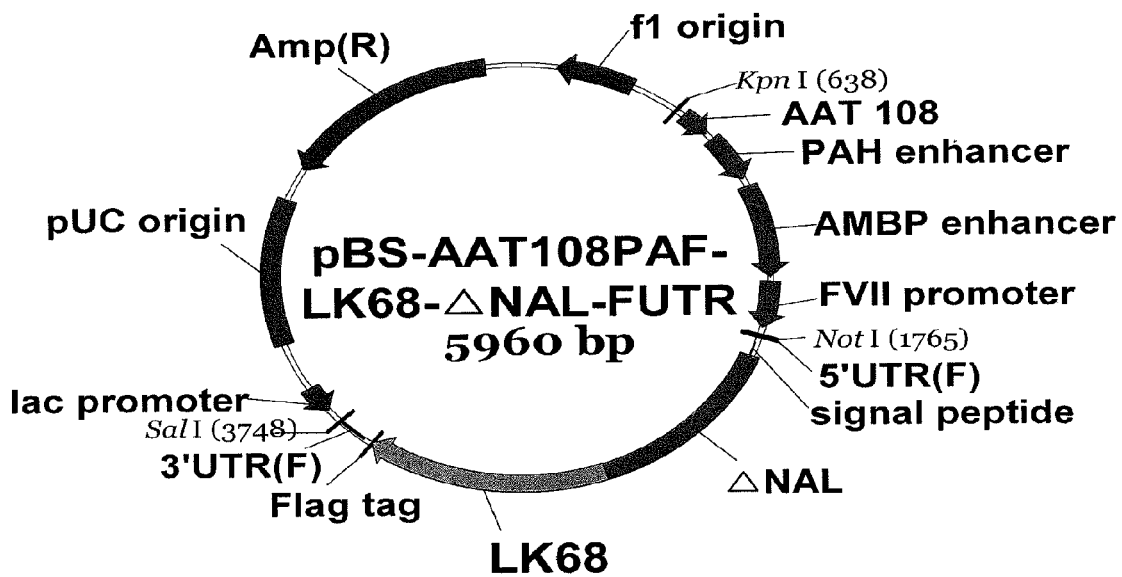

Further, the above procedure was repeated to obtain expression vectors including expression cassettes AAT108-PF-LK68, AAT108-PF-LK68-FUTR, AAT108-PF-LK68-ΔNAL-FUTR, AAT108-PAF-LK68, AAT108-PAF-LK68-FUTR and AAT108-PAF-LK68-ΔNAL-FUTR. Schematic diagrams of the expression vectors are shown in FIG. 15B.

The expression vectors were injected into mouse tail veins according to the same method as in <step 3> of Example 2. Blood samples were collected from the mice, and the expression level of LK68 protein was measured by ELISA.

Figure 16B:
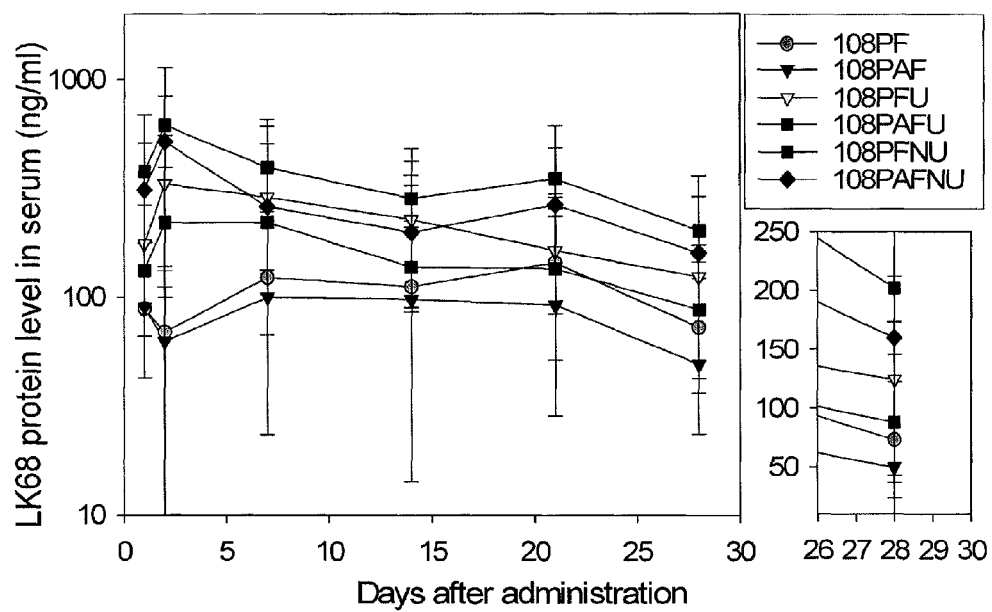
FIG. 16B: ELISA results showing the expression level of LK68 protein in the plasma samples obtained from the mice injected through tail vein with expression vectors carrying AAT108-PF/PAF-LK68 expression cassettes introduced UTR or UTR and intron ΔNAL.

As shown in FIG. 16B, the LK68 expression efficiencies of the AAT108-PF-LK68-FUTR and AAT108-PF-LK68-ΔNAL-FUTR expression vectors were respectively 197.7% and 425.4% at day 1 after the injection, 478.6% and 891.2% at day 2, 233.2% and 319.3% at day 7, 203.0% and 253.7% at week 2, 113.8% and 243.3% at week 3 and 170.4% and 277.6% at week 4, relative to that of the AAT108-PF-LK68 expression vector. The LK68 expression efficiencies of the AAT108-PAF-LK68-FUTR and AAT108-PAF-LK68-ΔNAL-FUTR expression vectors were respectively 147.0% and 344.6% at day 1 after the injection, 351.0% and 824.5% at day 2, 220.2% and 260.3% at day 7, 140.8% and 203.0% at week 2, 146.5% and 288.4% at week 3 and 177.8% and 323.8% at week 4, relative to that of the AAT108-PAF-LK68 expression vector.

These results show that gene expression in the presence of intron and/or UTR is sustained at a high level, as compared to that in the absence of intron and UTR.

EXAMPLE 6

Evaluation of Expression Efficiency of Kringle Domain KIV9-KIV10-KV (LK68) of Anti-Angiogenesis Protein Apo (a) by UTR and Intron in Cells LK68 and LK68-ΔNAL-FUTR fragments obtained by digesting the AAT108-PF-LK68 and AAT108-PF-LK68-ΔNAL-FUTR vectors described in Example 5 with NotI and SalI were inserted into adenovirus shuttle vectors pENTR2B (Invitrogen, Carlsbad, Calif.) to obtain pENTR-LK68 and pENTR-LK68-ΔNAL-FUTR vectors. These shuttle vectors and a target vector pAd/CMV/V5-DEST (Invitrogen, Carlsbad, Calif.) were subjected to in vitro homologous recombination with Clonase™ (Invitrogen, Carlsbad, Calif.) to obtain pAd-CMV-LK68 and pAd-CMV-LK68-ΔNAL-FUTR vectors. The pAd-CMV-LK68 and pAd-CMV-LK68-ΔNAL-FUTR vectors were linearized with a PacI restriction enzyme, and transfected into a HEK 293 kidney cell line to obtain replication-defective adenoviruses rAd-LK68 and rAd-LK68_UN carrying CMV-LK68 and CMV-LK68-ΔNAL-FUTR, respectively. The rAd-LK68 and rAd-LK68_UN were infected into HEK 293 kidney cell line, and the expression level of LK68 protein was measured.

The infection into the HEK 293 kidney cell lines was performed at different multiplicity of infection (MOI) of 0.1, 0.5, 2 and 10. The cells and media were collected at 2 days after adenovirus infection. The expression level of LK68 protein was measured by electrophoresis using anti-LK68 antibody. The results are shown in FIGS. 17A and 17B.

Figure 17A:
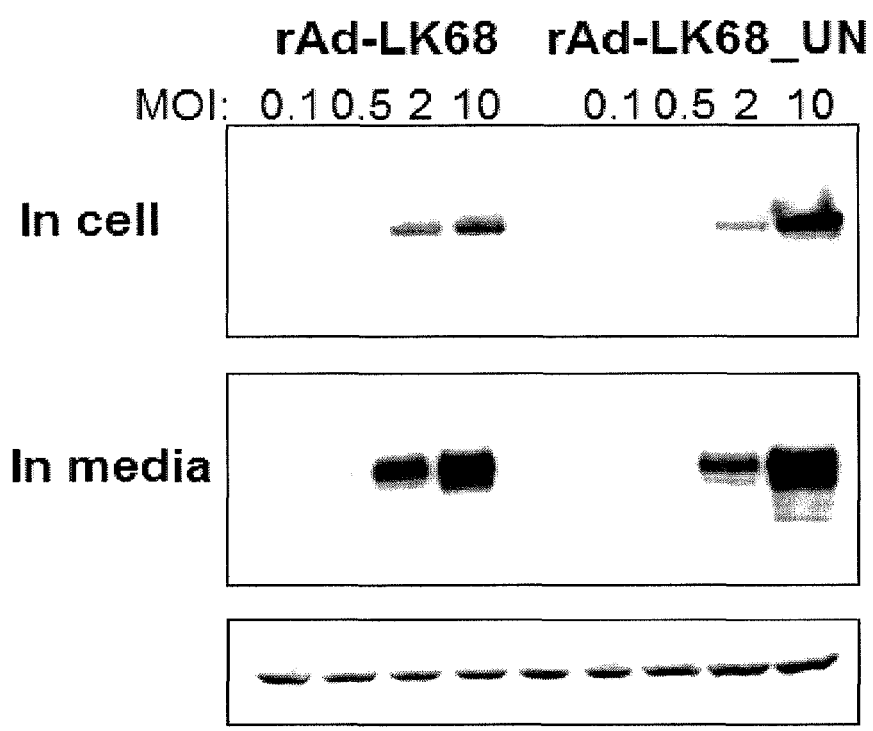
FIG. 17A: Western blot analysis results for LK68 protein expression levels in HEK293 cells infected with replication-defective adenoviruses carrying CMV-LK68 and CMV-LK68-ΔNAL-UTR expression cassettes at different multiplicity of infection ratios (MOI), and in theirs culture media.
Figure 17B:
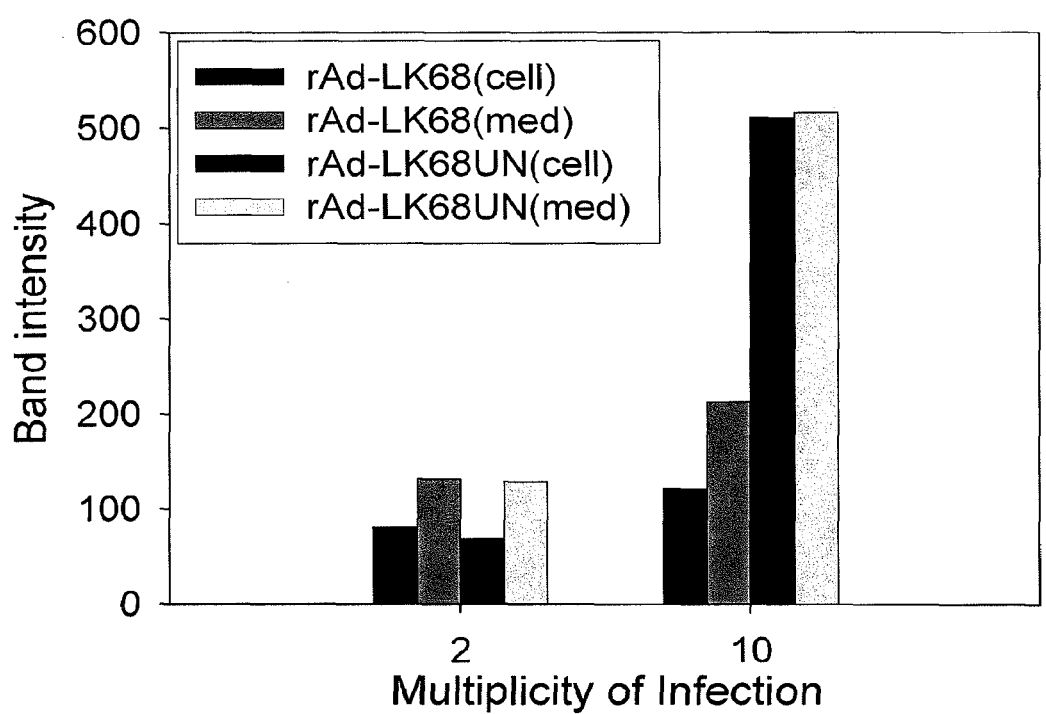
FIG. 17B: a histogram for band intensities obtained from the Western blot analysis results of FIG. 17A to show an effect of UTR and intron on gene expression.

As shown in FIGS. 17A and 17B, at MOI 0.1, 0.5 and 2, the expression levels of LK68 protein were low and equal, however at MOI 10, the expression level of LK68 protein induced by rAd-LK68_UN was increased 420% in cells and 242% in media, as compared with that induced by rAd-LK68.

These results show that gene expression efficiency in cells and media is higher in the presence of UTR and intron than in the absence of UTR and intron.

While the invention has been described with respect to the above specific embodiments, it should be recognized that various modifications and changes may be made and also fall within the scope of the invention as defined by the claims that follow.

What is claimed is:

1. An isolated polynucleotide consisting of the nucleotide sequence as set forth in SEQ ID NO: 49.

2. An expression cassette comprising:
   a promoter;
   a coding sequence operably linked to and under control of the promoter; and
   an intron consisting of the nucleotide sequence as set forth in SEQ ID NO: 49, said intron being operably linked to the coding sequence.

3. The expression cassette of claim 2, wherein the promoter is selected from the group consisting of polynucleotides having the nucleotide sequences as set forth in SEQ ID NOS: 41, 42 and 43.

4. The expression cassette of claim 2, further comprising at least one of enhancers having the nucleotide sequences as set forth in SEQ ID NOS: 44 or 45, wherein the at least one enhancers are operably linked to the coding sequence.

5. The expression cassette of claim 2, further comprising at least one of locus control regions having the nucleotide sequences selected from the group consisting of the nucleotide sequences as set forth in SEQ ID NOS: 58-60 and 61, wherein the at least one locus control regions are operably linked to the coding sequence.

6. The expression cassette of claim 2, further comprising untranslated regions having nucleotide the sequences of SEQ ID NOS: 62 and 63 at 5' and 3'-ends of the coding sequence, respectively, wherein the untranslated regions are operably linked to the coding sequence.

7. The expression cassette of claim 2, wherein the coding sequence is a nucleotide sequence encoding a liver-specific protein selected from the group consisting of albumin, α-fetoprotein, α-glucosidase, α1-antitrypsin, antithrombin, lipoproteins, ceruloplasmin, coagulation factor VII, coagulation factor VIII, coagulation factor IX, erythropoietin, fibrinogen, glucocerebrosidase, haptoglobin, IGF-1, insulin, plasminogen, prothrombin and transferrin.

8. An expression vector comprising the expression cassette of claim 2.

9. The expression cassette of claim 4, further comprising at least one of locus control regions having the nucleotide sequences selected from the group consisting of the nucleotide sequences as set forth in SEQ ID NOS: 58-60 and 61, wherein the at least one locus control regions are operably linked to the coding sequence.

10. The expression cassette of claim 9, further comprising untranslated regions, having the nucleotide sequences of SEQ ID NOS: 62 and 63 at 5' and 3'-ends of the coding sequence, respectively, wherein the untranslated regions are operably linked to the coding sequence.

11. The expression cassette of claim 4, further comprising untranslated regions having the nucleotide sequences of SEQ ID NOS: 62 and 63 at 5' and 3'-ends of the coding sequence, respectively, wherein the untranslated regions are operably linked to the coding sequence.

12. The expression cassette of claim 5, further comprising untranslated regions having the nucleotide sequences of SEQ ID NOS: 62 and 63 at 5' and 3'-ends of the coding sequence, respectively, wherein the untranslated regions are operably linked to the coding sequence.

13. An expression vector comprising the expression cassette of claim 4.

14. An expression vector comprising the expression cassette of claim 5.

15. An expression vector comprising the expression cassette of claim 6.

16. An expression vector comprising the expression cassette of claim 9.

17. An expression vector comprising the expression cassette of claim 10.

18. An expression vector comprising the expression cassette of claim 11.

19. An expression vector comprising the expression cassette of claim 12.

* * * * *